United States Patent
Moyron-Quiroz et al.

(10) Patent No.: US 12,006,363 B2
(45) Date of Patent: Jun. 11, 2024

(54) ANTI-TETRASPANIN 33 AGENTS AND COMPOSITIONS AND METHODS FOR MAKING AND USING THE SAME

(71) Applicant: BioLegend, Inc., San Diego, CA (US)

(72) Inventors: Juan E. Moyron-Quiroz, San Diego, CA (US); Takatoku Oida, Osaka (JP)

(73) Assignee: BioLegend, Inc., San Diego, CA (US)

( * ) Notice: Subject to any disclaimer, the term of this patent is extended or adjusted under 35 U.S.C. 154(b) by 916 days.

(21) Appl. No.: 17/028,202

(22) Filed: Sep. 22, 2020

(65) Prior Publication Data

US 2021/0095018 A1 Apr. 1, 2021

Related U.S. Application Data

(63) Continuation of application No. PCT/US2019/025807, filed on Apr. 4, 2019.

(60) Provisional application No. 62/653,898, filed on Apr. 6, 2018.

(51) Int. Cl.
*A61K 39/395* (2006.01)
*A61K 39/00* (2006.01)
*C07K 16/28* (2006.01)
*G01N 33/68* (2006.01)

(52) U.S. Cl.
CPC ......... *C07K 16/28* (2013.01); *G01N 33/6854* (2013.01); *C07K 2317/14* (2013.01); *C07K 2317/565* (2013.01); *C07K 2317/76* (2013.01)

(58) Field of Classification Search
None
See application file for complete search history.

(56) References Cited

FOREIGN PATENT DOCUMENTS

| CN | 101855241 A | 10/2010 |
|---|---|---|
| CN | 103237901 A | 8/2013 |
| CN | 105492023 A | 4/2016 |
| WO | 2008073300 | 6/2008 |
| WO | 2014100746 | 6/2014 |
| WO | 2016210241 | 12/2016 |
| WO | 2017196426 | 11/2017 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Rabia et al. Understanding and overcoming trade-offs between antibody affinity, specificity, stability and solubility. Biochem Eng J. Sep. 15, 2018; 137: 365-374 (Year: 2018).*
Beckwith et al., Tetraspanins as Therapeutic Targets in Hematological Malignancy: A Concise Review, Frontiers in Physiology, vol. 6, No. 91, Mar. 23, 2015, 13 pages.
Luu et al., TSPAN33 is a Novel Marker of Activated and Malignant B Cells, Clinical Immunology, vol. 149, No. 3, Aug. 15, 2013, 22 pages.
International Application No. PCT/US2019/025807, International Search Report and Written Opinion, Mailed on Oct. 25, 2019, 23 pages.
Rudikoff et al., Single Amino Acid Substitution Altering Antigen-Binding Specificity, Proceedings of the National Academy of Sciences, Immunology, vol. 79, No. 6, Mar. 1982, pp. 1979-1983.
European Application No. 19728753.5, Office Action mailed on Dec. 21, 2022, 6 pages.
International Application No. PCT/US2019/025807, International Preliminary Report on Patentability mailed on Oct. 15, 2020, 14 pages.
International Application No. PCT/US2019/025807, Invitation to Pay Addition Fees and Where Applicable, Protest Fee mailed on Aug. 28, 2019, 14 pages.

* cited by examiner

*Primary Examiner* — Maher M Haddad
(74) *Attorney, Agent, or Firm* — Kilpatrick Townsend & Stockton LLP

(57) ABSTRACT

Compositions and methods for making and using anti-TSPAN33 agents, for example, monoclonal antibodies, TSPAN33-binding antibody fragments, and derivatives, are described.

9 Claims, 15 Drawing Sheets

Specification includes a Sequence Listing.

VH and VL sequence analysis for TSPAN33 clones

Heavy chain variable region comparison:

```
                             -CDR1             ------CDR2---
AB1-H    EVKLVESGGGLVQPGGSLSLSCAASGFTFTDYYMTWVRQPPGKALEWLVFIRNKANGYTT
AB2-H    QVQLQQPGAELLKPGASVKLSCKASGYTFTSYWMHWVKQRPGRGLEWIGRIDPNSGG---T
AB3-H    EAQLQQSGPELVKPGASVKISCKASGYTFTNYYMNWMKQSHGKSLEWIGDIIPNNGG---T
AB4-H    EVQLQQSGPELVKPGASVKISCKASGYTFTNYYMNWMKQSHGKSLEWIGDIIPNNGG---T
AB5-H    QVQLQQPGAEFVKPGASVKLSCKASGYTFTSYWMHWVKQRPGQGLEWIGEINPNNGG---S
          . :*  :.*   ::.**.*:. :** ***:***.*:*  *:: *  *:.***:  *   .*   :

----CDR3----
AB1-H    EYSASVKGRFTISRDNSQSILYLQMNALRAEDSATYYCAR-YLQTGNFDYWGQGTTLTVSS (SEQ ID NO:4)
AB2-H    KYNEKFKSKATLTVDKPSSTAYIHLSSLTSEDSAVYYCAR-FIITGYFDYWGQGTTLIVSS (SEQ ID NO:12)
AB3-H    IYNQKFKGKATLTVDRSSSTAYMELRSLTSEDSAVYYCAR-RLWSWYFDVWGTGTTVTVSS (SEQ ID NO:20)
AB4-H    IYNQKFKGKATLTVDRSSSTAYMELRSLTSEDSAVYYCAR-RLWSWYFDVWGTGTTVTVSS (SEQ ID NO:28)
AB5-H    NYNEKFKNKATLTVDKSSSTAYMQLSGLTSEDSAVYYCTRSYYSYWYFDYWGQGTTLTVSS (SEQ ID NO:36)
          *.  ..*.: *::  *..* *:.: .* :****.***:*      ** ** ***: ***
```

Light chain variable region comparison:

```
                         -----CDR1------         -CDR2-
AB1-L    EIQMIQTTSSLTASLGDRVTISCRASQDISNFLNWYQQKPDGTIKLLIYFTSRLHSGVPS
AB2-L    DIVMTQSHKFMSTSVGDRVSITCKASQDVGAAVAWYQQKPGQSPKLLIYWASTRHTGVPD
AB3-L    QIVLTQSPALMSASPGEKVTMTCSASSSVS-YMYWYQQKPRSSPKPWIYLTSNLASGVPA
AB4-L    QIVLTQSPALMSASPGEKVTMTCSASSSVS-YMYWYQQKPRSSPKPWIYLTSNLASGVPA
AB5-L    QIVLTQSPAIMSASPGQKVTITCSASSSVN-YMHWYQQKLGSSPKLWIYDTSKLAPGVPA
          :* : *:    :::* *:::* **.:.   : *****  : * ** :*   .***

---CDR3----
AB1-L    RFSGSGSGTDYSLTISNLEQEDIATYFCQQGYTVPPTFGGGTKLEIK (SEQ ID NO:8)
AB2-L    RFTGSGSGTDFTLTISTVQSEDLADYFCHQYRTYPFTFGSGTKLGIK (SEQ ID NO:16)
AB3-L    RFSGSGSGTSYSLTISSMEAEDAATYYCQQWSSNPYTFGGGTKLEIK (SEQ ID NO:24)
AB4-L    RFSGSGSGTSYSLTISSMEAEDAATYYCQQWSSNPYTFGGGTKLEIK (SEQ ID NO:32)
AB5-L    RFSGSGSGTSYSLTISNMEAEDAASYFCHQWNNYPYTFGSGTKLEIK (SEQ ID NO:40)
          **:******.::****.::  ** * *:*   .  * ***.**** **
```

Fig. 3

Blocking of Abs anti-TSPAN33 on activated B cells

Blocking of Abs anti-TSPAN33 on monocytes
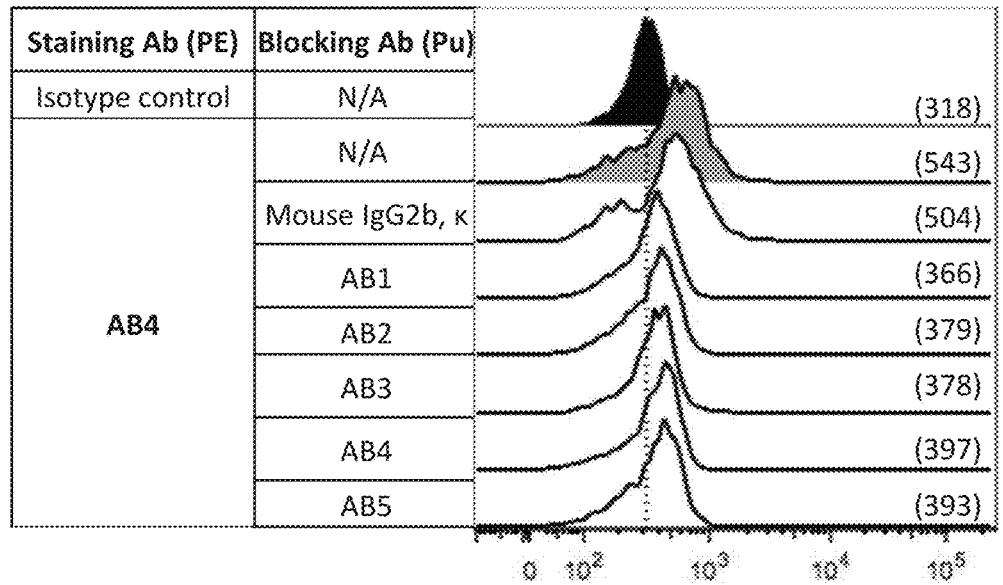
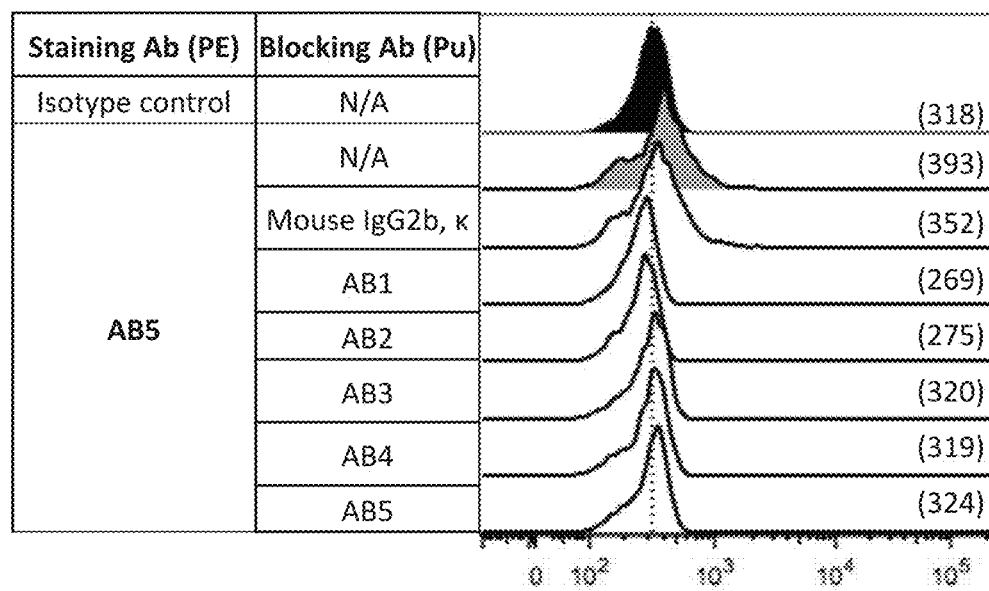
Fig. 8B

Summary of TSPAN33 blocking assays on B cells and monocytes

| Cell Subset | PE conjugate | Block | MFI | % Blocking | Cell Subset | PE conjugate | Block | MFI | % Blocking |
|---|---|---|---|---|---|---|---|---|---|
| B cells | | MouseIgG2b | N/A | 104 | N/A | Monocytes | | MouseIgG2b | N/A | 318 | N/A |
| | AB1 | N/A | 768 | N/A | | | N/A | 362 | N/A |
| | | Rat IgG2b | 808 | 0.0 | | | Rat IgG2b | 357 | 1.4 |
| | | AB1 | 86.2 | 88.8 | | AB1 | AB1 | 225 | 37.8 |
| | | AB2 | 87.5 | 88.6 | | | AB2 | 232 | 35.9 |
| | | AB3 | 124 | 83.9 | | | AB3 | 265 | 26.8 |
| | | AB4 | 135 | 82.4 | | | AB4 | 244 | 32.6 |
| | | AB5 | 112 | 85.4 | | | AB5 | 256 | 29.3 |
| | AB2 | N/A | 948 | N/A | | | N/A | 413 | N/A |
| | | Rat IgG2b | 1017 | 0.0 | | | Rat IgG2b | 412 | 0.2 |
| | | AB1 | 101 | 89.3 | | AB2 | AB1 | 253 | 38.7 |
| | | AB2 | 92.7 | 90.2 | | | AB2 | 250 | 39.5 |
| | | AB3 | 143 | 84.9 | | | AB3 | 252 | 39.0 |
| | | AB4 | 159 | 83.2 | | | AB4 | 246 | 40.4 |
| | | AB5 | 120 | 87.3 | | | AB5 | 256 | 38.0 |
| | AB3 | N/A | 510 | N/A | | | N/A | 510 | N/A |
| | | Rat IgG2b | 543 | 0.0 | | | Rat IgG2b | 610 | 0.0 |
| | | AB1 | 141 | 72.4 | | AB3 | AB1 | 424 | 16.9 |
| | | AB2 | 142 | 72.2 | | | AB2 | 410 | 19.6 |
| | | AB3 | 197 | 61.4 | | | AB3 | 411 | 19.4 |
| | | AB4 | 187 | 63.3 | | | AB4 | 363 | 28.8 |
| | | AB5 | 135 | 73.5 | | | AB5 | 451 | 11.6 |
| | AB4 | N/A | 497 | N/A | | | N/A | 543 | N/A |
| | | Rat IgG2b | 493 | 0.0 | | | Rat IgG2b | 504 | 7.2 |
| | | AB1 | 112 | 77.0 | | AB4 | AB1 | 366 | 32.6 |
| | | AB2 | 113 | 76.8 | | | AB2 | 379 | 30.2 |
| | | AB3 | 166 | 65.9 | | | AB3 | 378 | 30.4 |
| | | AB4 | 168 | 65.5 | | | AB4 | 397 | 26.9 |
| | | AB5 | 124 | 74.5 | | | AB5 | 393 | 27.6 |
| | AB5 | N/A | 941 | N/A | | | N/A | 393 | N/A |
| | | Rat IgG2b | 715 | 24.0 | | | Rat IgG2b | 352 | 10.4 |
| | | AB1 | 95.2 | 89.9 | | AB5 | AB1 | 269 | 31.6 |
| | | AB2 | 93.6 | 90.1 | | | AB2 | 275 | 30.0 |
| | | AB3 | 123 | 86.9 | | | AB3 | 320 | 18.6 |
| | | AB4 | 128 | 86.4 | | | AB4 | 319 | 18.8 |
| | | AB5 | 115 | 87.8 | | | AB5 | 324 | 17.6 |

Fig. 11

ANTI-TETRASPANIN 33 AGENTS AND COMPOSITIONS AND METHODS FOR MAKING AND USING THE SAME

RELATED PATENT APPLICATION(S)

The present application is a continuation of International Patent Application No. PCT/US2019/025807, filed on Apr. 4, 2019, which claims the benefit of U.S. provisional patent application No. 62/653,898 filed on Apr. 6, 2018, entitled ANTI-TETRASPANIN 33 AGENTS AND COMPOSITIONS AND METHODS FOR MAKING AND USING THE SAME, naming Juan E. MOYRON-QUIROZ et al. as inventors. The entire content of the foregoing application is incorporated herein by reference, including all text, tables and drawings.

REFERENCE TO AN ELECTRONIC SEQUENCE LISTING

The contents of the electronic sequence listing (Updated ST25.txt; Size: 26000 bytes; and Date of Creation: Feb. 29, 2024) is herein incorporated by reference in its entirety.

TECHNICAL FIELD

The present invention relates to agents that bind Tetraspanin 33 (TSPAN33) and its variants, particularly to monoclonal antibodies, antibody fragments, and antibody derivatives specifically reactive to TSPAN33 under physiological conditions. Such agents can be used in the treatment and/or prevention of various diseases or disorders through the delivery of pharmaceutical or other compositions that contain such agents.

BACKGROUND

The following description includes information that may be useful in understanding the present invention. It is not an admission that any of the information provided herein, or any publication specifically or implicitly referenced herein, is prior art, or even particularly relevant, to the presently claimed invention.

TSPAN33 is a member of the transmembrane 4 superfamily (TM4SF) of proteins that have four transmembrane domains with intracellular N and C termini. All members of the family also express two extracellular domain loops. One loop (EC1) is very short and the second (EC2) is relatively long. The EC2 domain is also characterized by four or more cysteine amino acid residues.

The tetraspanin family members will associate with other tetraspanins and also with a repertoire of other transmembrane and intracellular molecules that have multiple functions in cell biology, e.g., Charrin et al, J. Cell. Sci. 127: 3641-3648 (2014). These interactions can be both direct and indirect, and the tetraspanins can regulate the function of the partner proteins. And, tetraspanins are able to regulate intracellular signaling pathways by coordinating the proximity of signaling molecules. Thus, the term "tetraspanin web" has been used to reflect the complexity of protein-protein interactions that can be mediated by tetraspanin family members. Furthermore, tetraspanin molecules are known to occupy specific areas, or "islands," within the cell membrane giving rise to the term "tetraspanin enriched microdomains." By orchestrating the assembly and signaling of several proteins in specific manners, the tetraspanins are able to play critical roles in a number of cellular processes such as adhesion, activation, metastasis, proteolysis and viral infection.

The expression of TSPAN33 throughout the human body is highly restricted, e.g., Luu et al, Clin Immunol. 149:388-399 (2013) and Heikens and Tsai, Blood, 109:3244-3252 (2007). Within the B lymphocyte lineage TSPAN33 is expressed only on activated primary B lymphocytes. This is different from CD19 and CD20, two proteins that are phenotypic markers expressed on all human B cells. TSPAN33 is also highly expressed in Hodgkin's lymphoma and Diffuse Large B Cell lymphomas, and is upregulated in a human Burkitt's lymphoma cell line that is used as a model of B cell activation and differentiation. TSPAN33 expression is also upregulated in blood cells obtained from human rheumatoid arthritis and systemic lupus erythematosus patients, both diseases where activated B cells contribute to the pathology. These restricted expression profiles for TSPAN33 in these various disease states make TSPAN33 an attractive molecule for pharmaceutical targeting to specifically reduce the contribution of activated B cell to the pathology.

The other primary site of TSPAN33 expression in the human body is in the kidney. Specifically, TSPAN33 is expressed on the epithelial cells of the proximal and distal tubules but not in the glomeruli. This restricted kidney expression renders the TSPAN33 molecules within the kidney inaccessible to therapeutic antibodies that might react with TSPAN33 since blood born antibodies are too large to pass the glomerular barrier and access the tubules expressing TSPAN33. TSPAN33 is also expressed on a small erythrocyte progenitor population in the bone marrow. TSPAN33 knockout mice (Tspan33−/−) indicated that TSPAN33 plays a role in normal erythropoiesis, but the loss of TSPAN33 was not lethal in these animals, e.g., Heikens and Tsai, Blood, 109:3244-3252 (2007).

For the treatment of lymphoma there are several therapeutic antibodies now available. Rituximab (anti-CD20) was the first approved antibody therapeutic. The CD20 protein is expressed on all mature, peripheral B cells and elimination of that population incurs the risk of opportunistic infections in the patient. Second generation anti-CD20 antibodies carrying a cytotoxic payload are now available. Examples include ibritumomab, anti-CD20 with a radioactive yttrium (Y-90) conjugate, and tositumomab, anti-CD20 with a radioactive iodine (I-131) conjugate. Brentuximab recognizes the CD30 molecule, which is expressed on Hodgkin's lymphoma cells, but the expression of CD30 on T cells as well as B cells leads to increased serious infections when brentuximab is used therapeutically. For the treatment of rheumatoid arthritis, rituximab (anti-CD20) has been used successfully. For the treatment of systemic lupus erythematosus, therapies that target B cell function such as the BlyS (B lymphocyte stimulator) protein have successfully reduced symptoms. This suggests that an antibody that eliminates activated B cells, such as one that targets TSPAN33, could be a successful therapy.

The more restricted expression of TSPAN33 to activated B cells and certain lymphomas makes it an attractive alternative therapeutic target as compared to anti-CD20 and anti-CD30 antibodies due to its decreased potential for serious side effects such as increased risk of life-threatening infection due to elimination of all immunoglobulin producing cells.

Creation of the monoclonal antibody was difficult since there is greater than 97% sequence homology between human TSPAN33 and either mouse or rat TSPAN33. Since mice and rats are the most common source of monoclonal antibodies, this high degree of homology reduced the likelihood that the rodent species would mount an immune response to the human protein immunogen. Several attempts were made, and many clones were rejected due to their failure to react with activated but not resting B cells and with B cell lymphomas.

Described herein are particular monoclonal antibodies to TSPAN33, as well as antigen-binding fragments of such antibodies that also bind TSPAN33. These antibodies (and TSPAN33-binding fragments thereof) do not appreciably react with resting human B cells, but do react with activated human B cells, with human lymphoma cell lines, and with Hodgkin's lymphoma tissue samples, but not non-Hodgkin's lymphoma samples.

Definitions

An "acceptor human framework" refers to a framework comprising the amino acid sequence of a heavy chain variable domain (VH) framework or a light chain variable domain (VL) framework derived from a human immunoglobulin framework or a human consensus framework, as defined herein. An acceptor human framework "derived from" a human immunoglobulin framework or a human consensus framework may comprise the same amino acid sequence thereof, or it may contain amino acid sequence changes. In some embodiments, the number of framework amino acid changes are 10 or less, 9 or less, 8 or less, 7 or less, 6 or less, 5 or less, 4 or less, 3 or less, or 2 or less. In some embodiments, the VH and/or VL acceptor human framework(s) is(are) identical in sequence to the VH and/or VL human immunoglobulin framework amino acid sequence or human consensus framework amino acid sequence.

"Framework" or "FR" refers to variable domain residues other than hypervariable region (HVR) residues. The FR of a variable domain generally consists of four FR domains: FR1; FR2; FR3; and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, et al., Sequences of Proteins of Immunological Interest, Fifth Edition, NIH Publication 91-3242, Bethesda Md. (1991), vols. 1-3. In some embodiments, for the VL, the subgroup is subgroup kappa I as in Kabat, et al., supra. In some embodiments, for the VH, the subgroup is subgroup III as in Kabat, et al., supra.

The term "hypervariable region" or "HVR", as used herein, refers to each of the regions of an antibody variable domain that are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Example hypervariable loops occur at amino acid residues 26-32 (L1), 50-52 (L2), 91-96 (L3), 26-32 (H1), 53-55 (H2), and 96-101 (H3). See Chothia and Lesk, J. Mol. Biol. 196:901-917 (1987). In contrast, example CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 as described by Kabat, et al., Sequences of Proteins of Immunological Interest, 5th Ed. Public Health Service, National Institutes of Health, Bethesda, Md. (1991). With the exception of CDR1 in VH, CDRs generally comprise the amino acid residues that form the hypervariable loops. CDRs also comprise "specificity determining residues," or "SDRs," which are residues that contact a particular antigen. Unless otherwise indicated, HVR residues and other residues in the variable domain (e.g., FR residues) are numbered herein according to Kabat, et al., supra.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt, et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, et al., J. Immunol. 150:880-887 (1993); Clarkson, et al., Nature 352:624-628 (1991).

"Affinity" refers to the strength of the sum total of noncovalent interactions between a single binding site of a molecule (e.g., an antibody) and its binding partner (e.g., an antigen). Unless indicated otherwise, "binding affinity" refers to intrinsic binding affinity, which reflects a 1:1 interaction between members of a binding pair (e.g., antibody and antigen). The affinity of a molecule X for its partner Y can generally be represented by a dissociation constant (Kd). Affinity can be measured by common methods known in the art, including those described herein. Specific illustrative and example embodiments for measuring binding affinity are described elsewhere herein. In some instances, antibodies herein bind to a target (e.g., TSPAN33) with a high affinity, e.g., a $K_d$ value of no more than about $1 \times 10^{-7}$ M; preferably no more than about $1 \times 10^{-8}$ M; and preferably no more than about $5 \times 10^{-9}$ M.

An "affinity matured" antibody refers to an antibody with one or more alterations in one or more hypervariable regions (HVRs), compared to a parent antibody that does not possess such alterations. Preferably, such alterations result in improved affinity of the antibody for its target antigen.

The term "anti-TSPAN33 agent" refers to a molecule that is, or comprises, one or more anti-TSPAN33 antibodies, TSPAN33-binding antibody fragments, or TSPAN33-binding antibody derivatives.

The terms "anti-TSPAN33 antibody" and "an antibody that binds to TSPAN33" refer to an antibody that is capable of binding TSPAN33 with sufficient affinity such that the antibody is useful as a diagnostic and/or therapeutic agent in targeting TSPAN33. In some embodiments, the extent of binding of an anti-TSPAN33 antibody (or antigen-binding fragment thereof) to an unrelated, non-TSPAN33 protein is less than about 10% of the binding of the antibody to TSPAN33 as measured, e.g., by a radioimmunoassay (RIA) or by Scatchard analysis or by surface plasmon resonance, such as, for example, Biacore. In certain embodiments, an antibody that binds to TSPAN33 has a dissociation constant (Kd) of 0.1 μM, 100 nM, 10 nM, 1 nM, 0.1 nM, 0.01 nM, or 0.001 nM (e.g., $10^{-7}$ M or less, e.g., from $10^{-7}$ M to $10^{-13}$ M. In certain embodiments, an anti-TSPAN33 antibody binds to an epitope of TSPAN33 that is conserved among TSPAN33 from different species.

The term "antibody" herein is used in the broadest sense and encompasses various antibody structures, including, but not limited to, monoclonal antibodies, polyclonal antibodies, multispecific antibodies (e.g., bispecific antibodies), and antibody fragments so long as they exhibit the desired antigen-binding activity.

An "antibody derivative" refers to a molecule other than an intact antibody that comprises a portion derived from an intact antibody (or antigen-binding fragment thereof) and that binds the antigen to which the intact antibody (or antigen-binding fragment thereof) binds. Examples of antibody derivatives include but are not limited to single chain variable fragments (scFv), diabodies, triabodies, etc., aptamers comprising multiple antigen-binding antibody fragments, single chain variable fragments, diabodies, triabodies, etc.

An "antibody fragment" or "antigen-binding antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2 and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, Md., 1991.

An "antibody that binds to the same epitope" as a reference antibody (e.g., an antibody that binds TSPAN33) refers to an antibody that blocks binding of the reference antibody to its antigen in a competition assay by 50% or more, and conversely, the reference antibody blocks binding of the antibody to its antigen in a competition assay by 50% or more.

The term "chimeric" antibody refers to an antibody in which a portion of the heavy and/or light chain is derived from a particular source or species, while the remainder of the heavy and/or light chain is derived from a different source or species.

A "human antibody" is one that possesses an amino acid sequence corresponding to that of an antibody produced by a human or a human cell or derived from a non-human source that utilizes human antibody repertoires or other human antibody-encoding sequences. This definition of a human antibody specifically excludes a "humanized" antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. In some embodiments, a humanized antibody (or antigen-binding fragment or derivative thereof), when aligned with the antibody from which the acceptor framework regions were derived, includes one or more amino acid substitutions (or deletions or insertions) at desired locations. In such embodiments, the amino acid residue(s) substituted (or inserted or deleted) at a particular position in the human (or other) or other FR corresponds to the amino acid residue(s) at the corresponding location(s) in the parent antibody (i.e., the non-human antibody from which the CDRs or HVRs were derived). A "humanized form" of an antibody, e.g., a non-human antibody, refers to an antibody that has undergone humanization.

The term "antibody drug conjugate" (ADC) as used herein is equivalent to the term "immunoconjugate", and represents a preferred class of agent-drug conjugates. Here, "agent-drug conjugate" is an anti-TSPAN33 agent (e.g., an anti-TSPAN33 antibody or TSPAN33-binding fragment or derivative thereof) conjugated to one or more heterologous molecule(s), including, but not limited to, a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "diagnostic reagent" refers to a compound, e.g., a target-specific antibody (or antigen-binding thereof) used to perform a diagnostic assay.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "rabbit antibody" is one that possesses an amino acid sequence that corresponds to that of an antibody produced by a rabbit or a rabbit cell or derived from a non-rabbit source that utilizes rabbit antibody repertoires or other rabbit antibody-encoding sequences.

An "immunoconjugate" is an antibody (or antigen-binding fragment or derivative thereof) conjugated to one or more heterologous molecule(s), including, but not limited to, a cytotoxic agent. An immunoconjugate is equivalent to the term "antibody drug conjugate" (ADC).

An "individual" or "patient" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" molecule is one that has been separated from a component of its natural environment. In some embodiments, for example, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In some instances, an "isolated" molecule (e.g., nucleic acid, antibody) refers to one that has been separated from a component of its original environment (e.g., the natural environment if it is naturally occurring, or a host cell if expressed exogenously), and thus is altered by human intervention (e.g., "by the hand of man") from its original environment. In some embodiments, for example, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). An isolated nucleic acid may refer to a nucleic acid molecule contained in cells that ordinarily contain the nucleic acid molecule, but the nucleic acid molecule is present extrachromosomally or at a chromosomal location that is different from its natural chromosomal location. In some embodiments, an isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components.

"Isolated nucleic acid encoding an anti-TSPAN33 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a recombinant host cell.

The term "TSPAN33," as used herein, refers to any native, mature TSPAN33 that results from processing of a TSPAN33 precursor protein in a cell. The term includes TSPAN33 from any vertebrate source, including mammals such as primates (e.g. humans and cynomolgus or rhesus monkeys) and rodents (e.g., mice and rats), unless otherwise indicated. The term also includes naturally occurring variants of TSPAN33, e.g., splice variants or allelic variants. The amino acid sequence of an example human TSPAN33 precursor protein is described in PCT/US2013/077273 (WO 2014/100746) and its corresponding U.S. national-stage filing, U.S. patent application Ser. No. 14/653,572 (publication no. US2016/0237152).

An example amino acid sequence for human precursor TSPAN33 is identified by GENBANK accession no. NP_848657.1 and is provided below:

```
                                           (SEQ ID NO: 47)
MARRPRAPAASGEEFSFVSPLVKYLLFFFNMLFWVISMVMVAVGVYARLM

KHAEAALACLAVDPAILLIVVGVLMFLLTFCGCIGSLRENICLLQTFSLC

LTAVFLLQLAAGILGFVFSDKARGKVSEIINNAIVHYRDDLDLQNLIDFG

QKKFSCCGGISYKDWSQNMYFNCSEDNPSRERCSVPYSCCLPTPDQAVIN

TMCGQGMQAFDYLEASKVIYTNGCIDKLVNWIHSNLFLLGGVALGLAIPQ

LVGILLSQILVNQIKDQIKLQLYNQQHRADPWY.
```

The term "TSPAN33-positive cell" refers any cell that expresses TSPAN33 on its surface. Some cells, including those associated with some cancer types and tumors, exhibit up-regulation of TSPAN33 expression.

The term "monoclonal antibody" refers to an antibody obtained from a population of substantially homogeneous antibodies, i.e., the individual antibodies comprising the population are identical (as assessed at the level of Ig heavy and/or light chain amino acid sequence) and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and should not be construed as requiring production of the antibody by any particular method. For example, the monoclonal antibodies for use in accordance with the present invention may be made by a variety of techniques, including, but not limited to, the hybridoma method, recombinant DNA methods, phage-display methods, and methods utilizing transgenic animals containing all or part of the human immunoglobulin loci, such methods and other example methods for making monoclonal antibodies being described herein.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical composition" refers to a preparation that is in such form as to permit the effective biological activity of an active ingredient contained therein, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

SUMMARY

This invention provides anti-TSPAN33 agents, including anti-TSPAN33 antibodies, TSPAN33-binding antibody fragments, derivatives, and variants of such antibodies and antibody fragments (including immunoconjugates, labeled antibodies and antigen-binding antibody fragments, etc.), and methods of making and using the same.

Provided herein, in certain aspects, is an anti-TSPAN33 agent that binds Tetraspanin 33 (TSPAN33) under laboratory or physiological conditions, where the agent comprises at least one immunoglobulin heavy chain variable domain and at least one immunoglobulin light chain variable domain, where a) each immunoglobulin heavy chain variable domain of the anti-TSPAN33 agent comprises first, second, and third heavy chain complementarity determining regions (CDRs), where the first heavy chain CDR (CDRH1) comprises a polypeptide that is at least 75 percent identical to the amino acid sequence $X_1YX_2MX_3$ (SEQ ID NO: 41), where $X_1$ is D, S or N, $X_2$ is Y or W, and $X_3$ is N, H or T; the second heavy chain CDR (CDRH2) comprises a polypeptide that is at least 75 percent identical to the amino acid sequence $X_1IX_2X_3X_4X_5X_6GX_7X_8X_9X_{10}YX_{11}X_{12}X_{13}X_{14}KX_{15}$ (SEQ ID NO: 42), where $X_1$ is F, R, D or E, $X_2$ is R, D, I or N, $X_3$ is N or P, $X_4$ is N or K, $X_5$ is A, S or N, $X_6$ is N or G, $X_7$ is Y or no amino acid, $X_8$ is T or no amino acid, $X_9$ is T or S, $X_{10}$ is E, K, I or N, $X_{11}$ is S or N, $X_{12}$ is A, E or Q, $X_{13}$ is S or K, $X_{14}$ is V or F, and $X_{15}$ is G, S or N; and the third heavy chain CDR (CDRH3) comprises a polypeptide that is at least 75 percent identical to the amino acid sequence $X_1X_2X_3X_4X_5X_6X_7FDX_8$ (SEQ ID NO: 43), where $X_1$ is no amino acid or S, $X_2$ is Y, F or R, $X_3$ is L, I or Y, $X_4$ is Q, I, W or S, $X_5$ is T, S or Y, $X_6$ is G or W, $X_7$ is N or Y, and $X_8$ is Y or V; and b) each immunoglobulin light chain variable domain of the anti-TSPAN33 agent comprises first, second, and third light chain CDRs, where the first light chain CDR (CDRL1) comprises a polypeptide that is at least 75 percent identical to the amino acid sequence $X_1ASX_2X_3X_4X_5X_6X_7X_8X_9$ (SEQ ID NO: 44), where $X_1$ is R, K or S, $X_2$ is Q or S, $X_3$ is D or S, $X_4$ is I or V, $X_5$ is S, G or N, $X_6$ is N, A or no amino acid, $X_7$ is F, A or Y, $X_8$ is L, V or M, and $X_9$ is N, A, Y or H; the second light chain CDR (CDRL2) comprises a polypeptide that is at least 75 percent identical to the amino acid sequence $X_1X_2SX_3X_4X_5X_6$ (SEQ ID NO: 45), where $X_1$ is F, W, L or D, $X_2$ is T or A, $X_3$ is R, T, N or K, $X_4$ is L or R, $X_5$ is H or A, and $X_6$ is S, T or P; and the third light chain CDR (CDRL3) comprises a polypeptide that is at least 75 percent identical to the amino acid sequence $X_1QX_2X_3X_4X_5PX_6T$ (SEQ ID NO: 46), where $X_1$ is Q or H, $X_2$ is G, Y or W, $X_3$ is Y, R, S or N, $X_4$ is T, S or N, $X_5$ is V, Y or N, and $X_6$ is P, F or Y.

Also provided in certain aspects is a first anti-TSPAN33 agent that binds Tetraspanin 33 (TSPAN33) under laboratory or physiological conditions, where the first agent competitively binds, or is capable of competitively binding, with a second anti-TSPAN33 agent, which second agent is an anti-TSPAN33 agent described herein.

Also provided in certain aspects is a first anti-TSPAN33 agent that binds Tetraspanin 33 (TSPAN33) under laboratory or physiological conditions, where the first agent binds to, or is capable of binding to, the same epitope as a second anti-TSPAN33 agent, which second agent is an anti-TSPAN33 agent described herein.

In one aspect, the invention provides isolated, non-naturally occurring anti-TSPAN33 agents, particularly antibodies, or antigen-binding fragments or derivatives thereof, that bind Tetraspanin 33 (TSPAN33) under physiological conditions. In the context of anti-TSPAN33 antibodies or antigen-binding fragments, such molecules generally comprise two immunoglobulin heavy chain variable domains and two immunoglobulin light chain variable domains. In such molecules, each of the immunoglobulin heavy and light chain variable domains comprise first, second, and third chain complementarity determining regions (CDRs) arrayed as follows: FR1-CDR1-FR2-CDR2-FR3-CDR3-FR4.

In the heavy chain variable domain portions, the first heavy chain CDR includes an amino acid sequence that has a sequence identity of at least 65 percent, optionally a sequence identity of at least 80 percent, at least 90 percent, at least 95 percent, and 100 percent identity with the amino acid sequence DYYMT (SEQ ID NO:1), the second heavy chain CDR includes an amino acid sequence that has a sequence identity of at least 65 percent, optionally a sequence identity of at least 80 percent, at least 90 percent, at least 95 percent, and 100 percent identity with the amino acid sequence FIRNKANGYTTEYSASVKG (SEQ ID NO:2), and the third heavy chain CDR includes an amino acid sequence that has a sequence identity of at least 65 percent, optionally a sequence identity of at least 80 percent, at least 90 percent, at least 95 percent, and 100 percent identity with the amino acid sequence YLQTGNFDY (SEQ ID NO:3).

In the light chain variable domain portions, the first light chain CDR includes an amino acid sequence that has a sequence identity of at least 65 percent, optionally a sequence identity of at least 80 percent, at least 90 percent, at least 95 percent, and 100 percent identity with the amino acid sequence RASQDISNFLN (SEQ ID NO:5), the second light chain CDR includes an amino acid sequence that has a sequence identity of at least 65 percent, optionally a sequence identity of 100 percent identity with the amino acid sequence FTSRLHS (SEQ ID NO:6), and the third light chain CDR includes an amino acid sequence that has a sequence identity of at least 65 percent, optionally a sequence identity of at least 80 percent, at least 90 percent, at least 95 percent, and 100 percent identity with the amino acid sequence QQGYTVPPT (SEQ ID NO:7).

In some preferred embodiments, the isolated, non-naturally occurring anti-TSPAN33 antibodies, or TSPAN33-binding fragments thereof, include a first heavy chain CDR having the amino acid sequence DYYMT (SEQ ID NO:1), the second heavy chain CDR has the amino acid sequence FIRNKANGYTTEYSASVKG (SEQ ID NO:2), the third heavy chain CDR has the amino acid sequence YLQTGNFDY (SEQ ID NO:3), the first light chain CDR has the amino acid sequence RASQDISNFLN (SEQ ID NO:5), the second light chain CDR has the amino acid sequence FTSRLHS (SEQ ID NO:6), and the third light chain CDR has the amino acid sequence (SEQ ID NO: 7)
QQGYTVPPT.

In some preferred embodiments, the isolated, non-naturally occurring anti-TSPAN33 antibodies, or TSPAN33-binding fragments thereof, include those where the immunoglobulin heavy chain variable domains have an amino acid sequence that has a sequence identity of at least 65 percent, optionally a sequence identity of at least 80 percent, at least 90 percent, at least 95 percent, and 100 percent identity with the amino acid sequence (SEQ ID NO: 4)
EVKLVESGGGLVQPGGSLSLSCAASGFTFTDYYMTWVRQPPGKALEWLVF
IRNKANGYTTEYSASVKGRFTISRDNSQSILYLQMNALRAEDSATYYCAR
YLQTGNFDYWGQGTTLTVSS, and the immunoglobulin light chain variable domains include an amino acid sequence that has a sequence identity of at least 65 percent, optionally a sequence identity of at least 80 percent, at least 90 percent, at least 95 percent, and 100 percent identity with the amino acid sequence (SEQ ID NO: 8)
EIQMIQTTSSLTASLGDRVTISCRASQDISNFLNWYQQKPDGTIKLLIYF
TSRLHSGVPSRFSGSGSGTDYSLTISNLEQEDIATYFCQQGYTVPPTFGG
GTKLEIK.

In some embodiments, the antibodies, or antigen-binding antibody fragments thereof, are monoclonal antibodies, and may be camel, human, humanized, mouse, rabbit, or other mammalian antibodies or antigen-binding antibody fragments. In some embodiments, the antibody (or antigen-binding antibody fragment) is an IgG. In other embodiments, the IgG is an IgG1, IgG2a or IgG2b, or IgG3, or IgG4.

In certain preferred embodiments of anti-TSPAN33 antibodies and antigen-binding antibody fragments that are other than fully human antibodies (i.e., antibodies produced or derived from a mammal capable of producing all or a portion of the human antibody repertoire), the molecules are chimer or humanized anti-TSPAN33 antibodies and antigen-binding antibody fragments.

In some preferred embodiments, the anti-TSPAN33 antibody, antigen-binding antibody fragment, or derivative or variant thereof includes a detectable label.

In some preferred embodiments, the anti-TSPAN33 antibody, antigen-binding antibody fragment, or derivative or variant thereof is part of an immunoconjugate that further includes a cytotoxic agent, for example, a nucleic acid, a peptide, a polypeptide, a small molecule, or an aptamer.

A related aspect of the invention concerns compositions that include an isolated, non-naturally occurring anti-TSPAN33 antibody or and antigen-binding antibody fragment according to the invention. In addition to containing an anti-TSPAN33 antibody or and antigen-binding antibody fragment of the invention, such compositions typically also include a carrier, preferably a pharmaceutically acceptable carrier. A pharmaceutically acceptable carrier may include solvents, dispersion media, coatings, antibacterial and antifungal agents, isotonic and absorption delaying agents, and the like. The phrase "pharmaceutically or pharmacologically acceptable" generally refers to molecular entities and compositions that do not produce adverse, allergic, or other untoward reactions when administered to an animal or a human. Supplementary active ingredients also may be incorporated into the compositions.

Such compositions are preferably packaged in containers, which in many preferred embodiments are further packaged into kits that also include instructions for use. In the context of pharmaceutical compositions, such kits instructions are a package insert containing not only instructions for use but also information about the pharmaceutically active ingredient (e.g., the anti-TSPAN33 antibody, antigen-binding antibody fragment, or derivative or variant thereof).

Another related aspect concerns diagnostics configured to detect TSPAN33 in a biological sample, often a biological sample taken from a subject. Such kits include an anti-TSPAN33 antibody, antigen-binding antibody fragment, or derivative or variant thereof according to the invention conjugated with detectable reagents such as fluorophores or enzyme substrates and/or immobilized on a solid support.

Still other aspects of the invention concern the manufacture of the anti-TSPAN33 antibody, antigen-binding antibody fragment, or derivative or variant thereof according to the invention. One such aspect concerns isolated nucleic acid molecules that encode the polypeptides of the invention. In some embodiments, such nucleic acids encode an immunoglobulin heavy chain variable domain having a first heavy chain CDR that includes an amino acid sequence that has a sequence identity of at least 65 percent, optionally a sequence identity of at least 80 percent, at least 90 percent, at least 95 percent, and 100 percent identity with the amino acid sequence DYYMT (SEQ ID NO:1), a second heavy chain CDR includes an amino acid sequence that has a sequence identity of at least 65 percent, optionally a sequence identity of at least 80 percent, at least 90 percent, at least 95 percent, and 100 percent identity with the amino acid sequence FIRNKANGYTTEYSASVKG (SEQ ID NO:2), and a third heavy chain CDR includes an amino acid sequence that has a sequence identity of at least 65 percent, optionally a sequence identity of at least 80 percent, at least 90 percent, at least 95 percent, and 100 percent identity with the amino acid sequence YLQTGNFDY (SEQ ID NO:3). Such nucleic acids also preferably encode an immunoglobulin light chain variable domain where the first light chain CDR includes an amino acid sequence that has a sequence identity of at least 65 percent, optionally a sequence identity of at least 80 percent, at least 90 percent, at least 95 percent, and 100 percent identity with the amino acid sequence RASQDISNFLN (SEQ ID NO:5), the second light chain CDR includes an amino acid sequence that has a sequence identity of at least 65 percent, optionally a sequence identity of 100 percent identity with the amino acid sequence FTSRLHS (SEQ ID NO:6), and the third light chain CDR includes an amino acid sequence that has a sequence identity of at least 65 percent, optionally a sequence identity of at least 80 percent, at least 90 percent, at least 95 percent, and 100 percent identity with the amino acid sequence QQGYTVPPT (SEQ ID NO:7).

In certain preferred embodiments, the nucleic acid molecules of the invention encode an immunoglobulin heavy chain variable domain having an amino acid sequence that has a sequence identity of at least 65 percent, optionally a sequence identity of at least 80 percent, at least 90 percent, at least 95 percent, and 100 percent identity with the amino acid sequence (SEQ ID NO: 4)
EVKLVESGGGLVQPGGSLSLSCAASGFTFTDYYMTWVRQPPGKALEWLVF

IRNKANGYTTEYSASVKGRFTISRDNSQSILYLQMNALRAEDSATYYCAR

YLQTGNFDYWGQGTTLTVSS, as well as an immunoglobulin light chain variable domain having an amino acid sequence that has a sequence identity of at least 65 percent, optionally a sequence identity of at least 80 percent, at least 90 percent, at least 95 percent, and 100 percent identity with the amino acid sequence (SEQ ID NO: 8)
EIQMIQTTSSLTASLGDRVTISCRASQDISNFLNWYQQKPDGTIKLLIYF

TSRLHSGVPSRFSGSGSGTDYSLTISNLEQEDIATYFCQQGYTVPPTFGG

GTKLEIK.

Related aspects concern plasmids, and expression cassettes and vectors, that carry the nucleic acids of the invention, as well as recombinant host cells transfected with such nucleic acid molecules.

Still other aspects of the invention concern methods of treating or preventing a disease or disorder associated with aberrant levels of Tetraspanin 33 (TSPAN33). Such methods include administering to a subject in need of such treatment an anti-TSPAN33 antibody, antigen-binding antibody fragment, or derivative or variant thereof in an amount sufficient to effect treatment, thereby treating or preventing the disease or disorder. Such diseases and disorders that can be so treated include leukemia; lymphoma, optionally, Hodgkin's disease, non-Hodgkin's lymphoma, diffuse large B cell lymphoma, and Burkitt's lymphoma; and an autoimmune disease, optionally, rheumatoid arthritis.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to limit the technology.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

A brief summary of each of the figures and tables described in this specification are provided below, as is a list of various nucleotide and amino acid sequences described herein.

FIG. 3 shows variable heavy chain (VH) and variable light chain (VL) sequence analysis for TSPAN33 clones. Clustal X was used for this analysis. According to Clustal X: three characters ("*", ":" and ".") are used in this analysis: "*" indicates positions which have a single, fully conserved residue. ":" indicates that one of the following 'strong' groups is fully conserved: STA, NEQK (SEQ ID NO:48). NHQK (SEQ ID NO:49), NDEQ (SEQ ID NO:50), QHRK (SEQ ID NO:51), MILV (SEQ ID NO:52), MILF (SEQ ID NO:53), HY, or FYW; "." indicates that one of the following 'weaker' groups is fully conserved: CSA, ATV, SAG, STNK (SEQ ID NO:54), STPA (SEQ ID NO:55), SGND (SEQ ID NO:56), SNDEQK (SEQ ID NO:57), NDEQHK (SEQ ID NO:58), NEQHRK (SEQ ID NO:59), FVLIM (SEQ ID NO:60), or HFY. These are all the positively scoring groups that occur in the Gonnet Pam250 matrix. The strong and weak groups are defined as strong score >0.5 and weak score=<0.5 respectively. Blank are those not matching any of the above three situations.

Histograms represent monocytes, which were identified by $FSC^{int}SSC^{int}$. Histogram gates are based on isotype staining (Mouse IgG2b, κ).

Figure 7A:
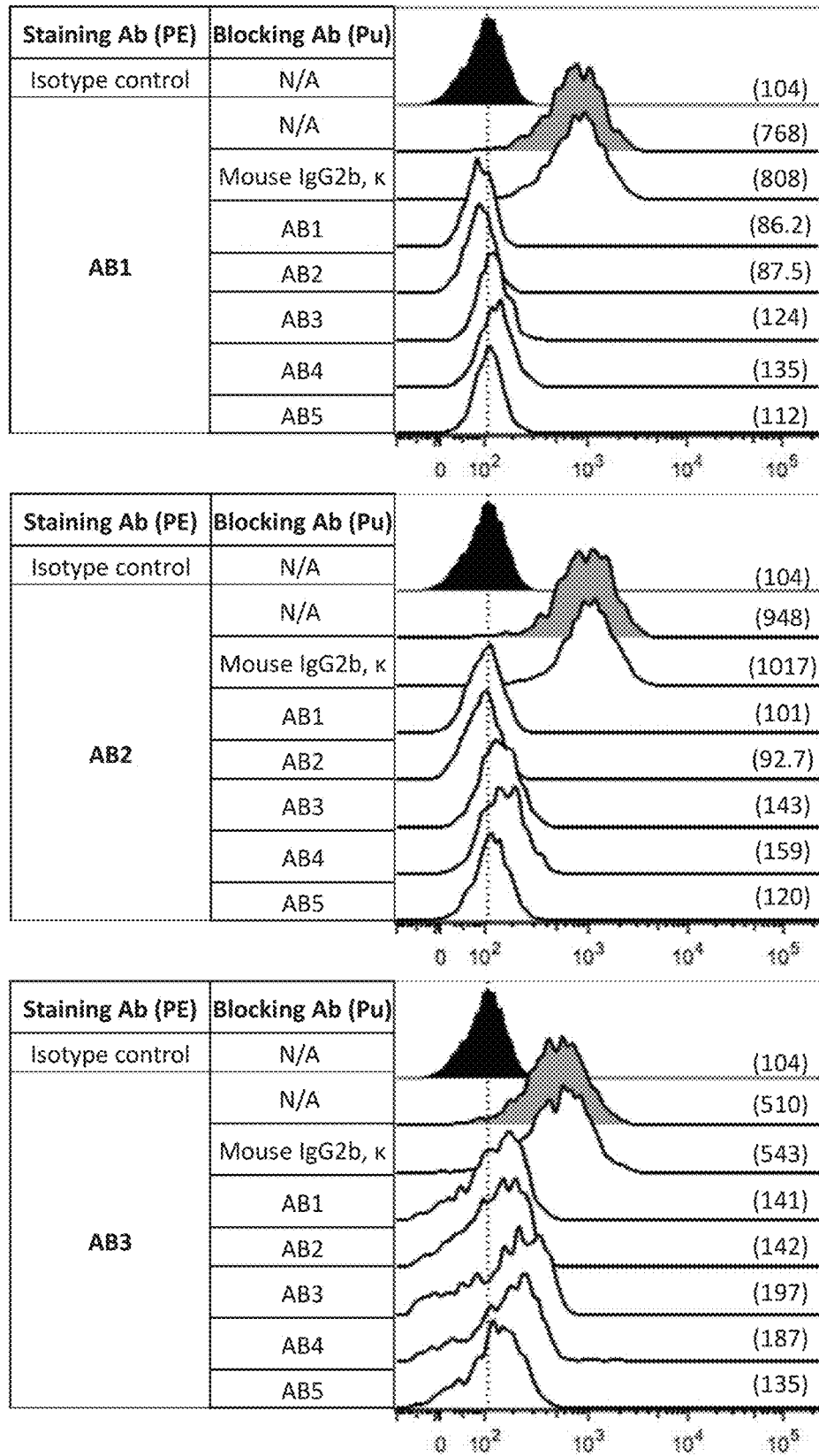
Figure 7B:
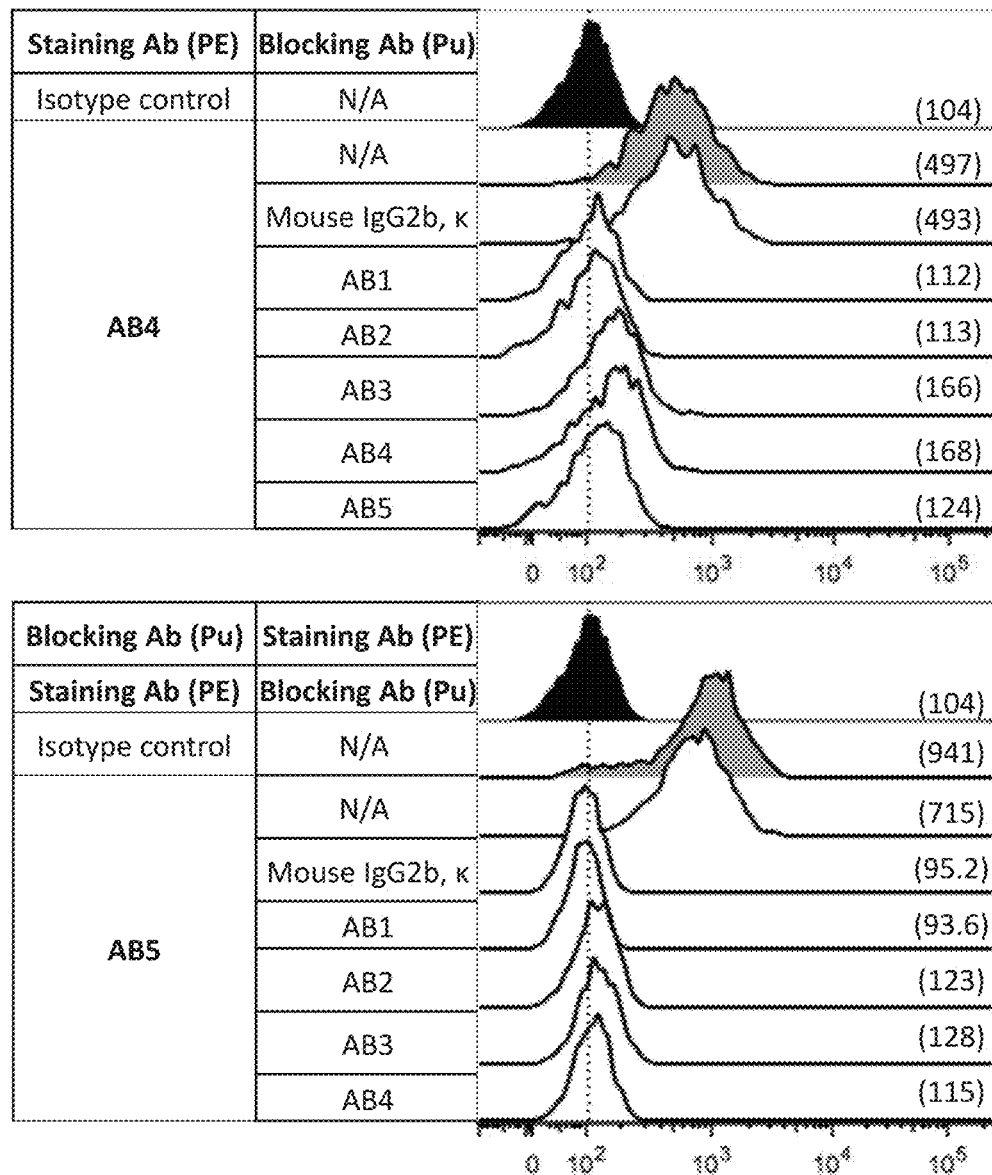

FIG. 7A and FIG. 7B show blocking the staining of TSPAN33 on PBMCs activated with CD40L (TNFSF5) plus IL-4, with different anti-TSPAN33 antibodies. The first column indicates the antibody used to stain the cells, the second column indicates the antibody used to block the staining; the numbers in parenthesis indicate the median fluorescence intensity of the B cells after blocking and staining with the indicated antibodies. The black histogram correspond to B cells stained with an isotype control antibody only, the dotted line marks the median fluorescence of these cells; the gray histogram shows the staining of the tested antibody without any blocking. Data is gated on lymphocytes ($FSC^{lo}SSC^{lo}$) and $CD20^+$ cells to identify B cells.

Figure 8A:
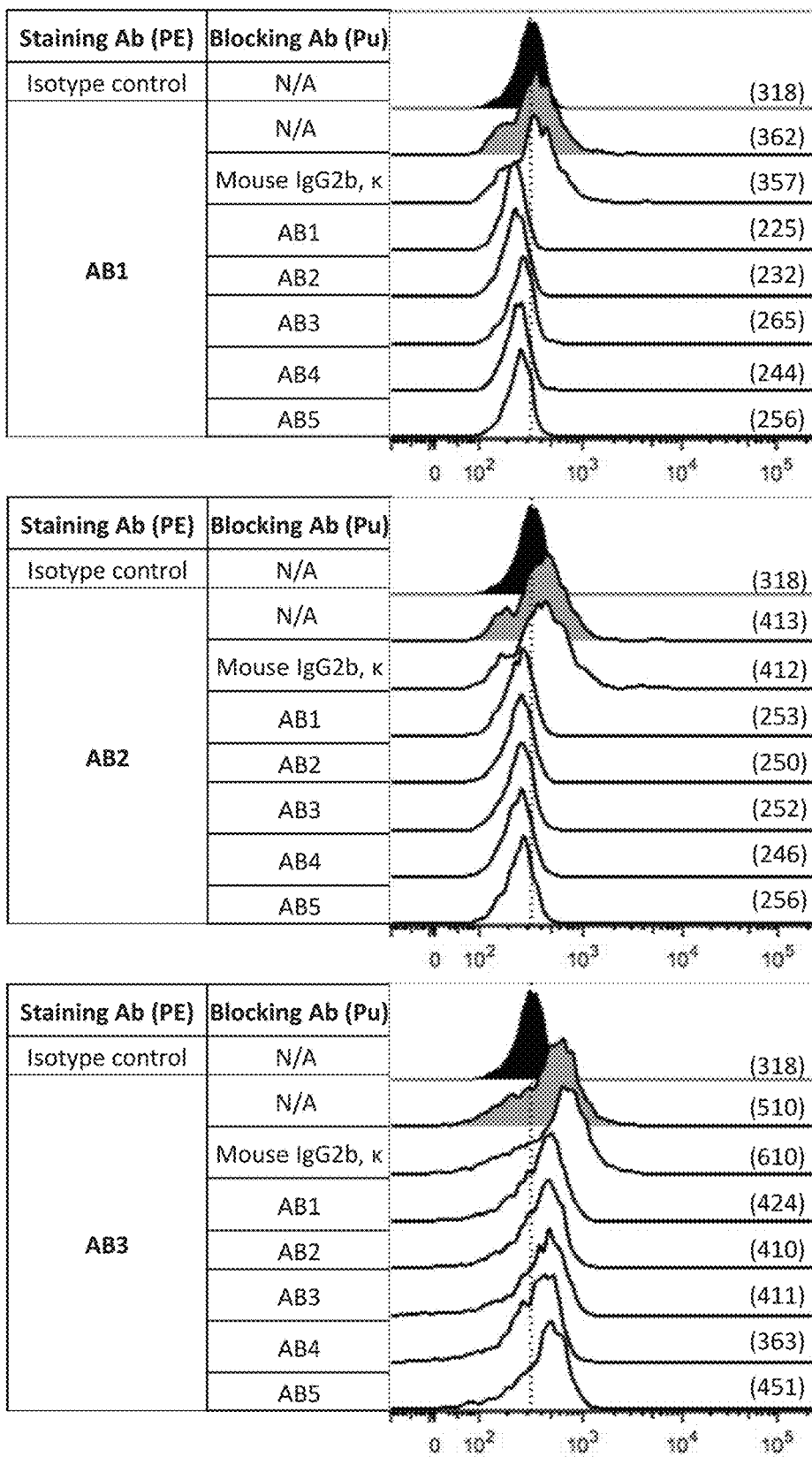

FIG. 8A and FIG. 8B show blocking the staining of TSPAN33 on PBMCs activated with CD40L (TNFSF5) plus IL-4, with different anti-TSPAN33 antibodies. The first column indicates the antibody used to stain the cells, the second column indicates the antibody used to block the staining; the numbers in parenthesis indicate the median fluorescence intensity of the monocytes after blocking and staining with the indicated antibodies. The black histogram correspond to monocytes stained with an isotype control antibody only, the dotted line marks the median fluorescence of monocytes stained with isotype control only; the gray histogram shows the staining of the tested antibody without any blocking. Data is gated on monocytes ($FSC^{int}SSC^{int}$).

Figure 9:
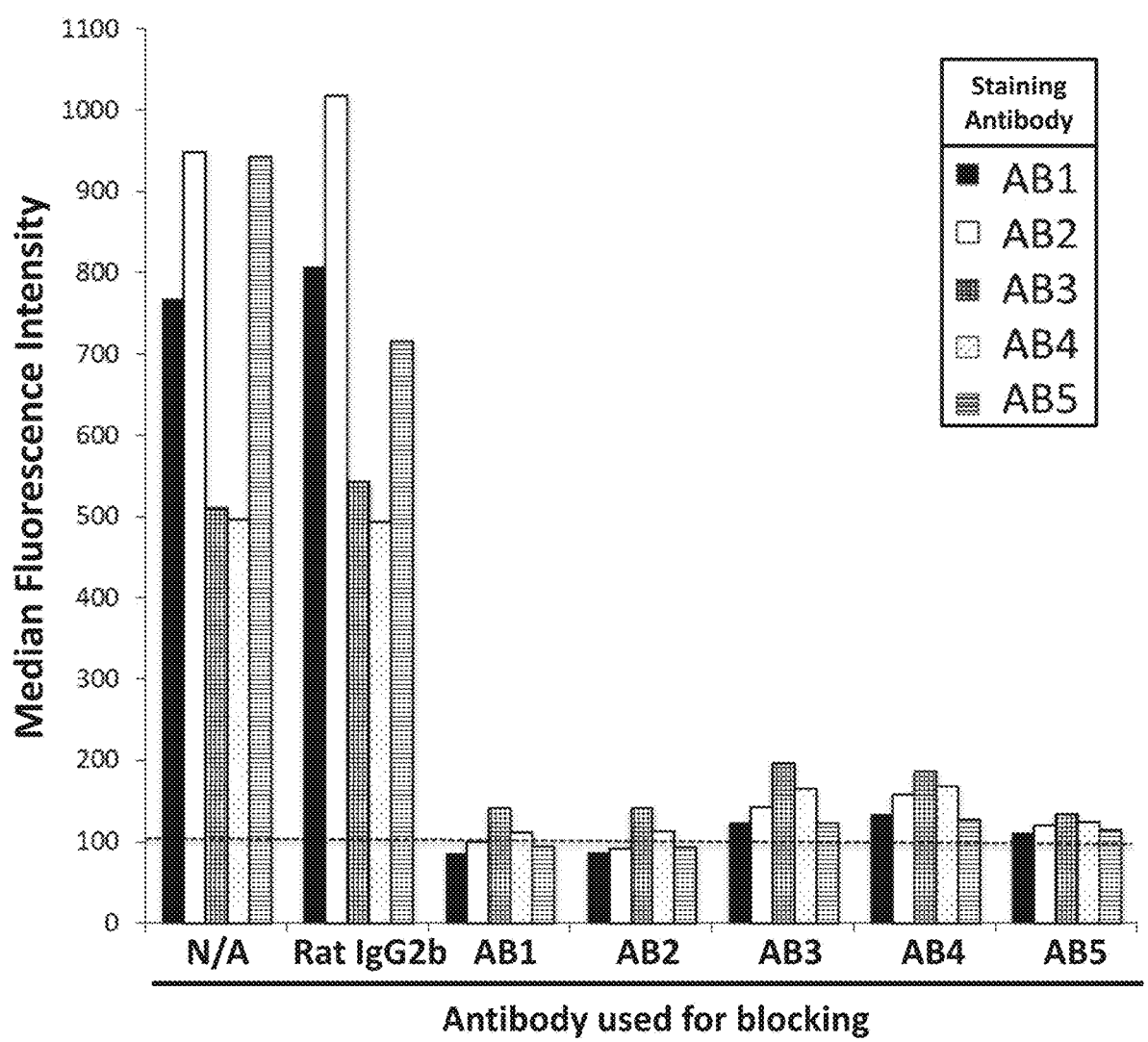

FIG. 9 shows a summary of anti-TSPAN33 blocking assays on B cells cultured overnight with CD40L (TNFSF5) plus IL-4. The x-axis indicates the antibody used to block the staining, and the bars indicate the antibody used to stain the cells; the dotted line indicates the median fluorescence of activated B cells stained with an isotype control (Mouse IgG2b, κ).

Figure 10:
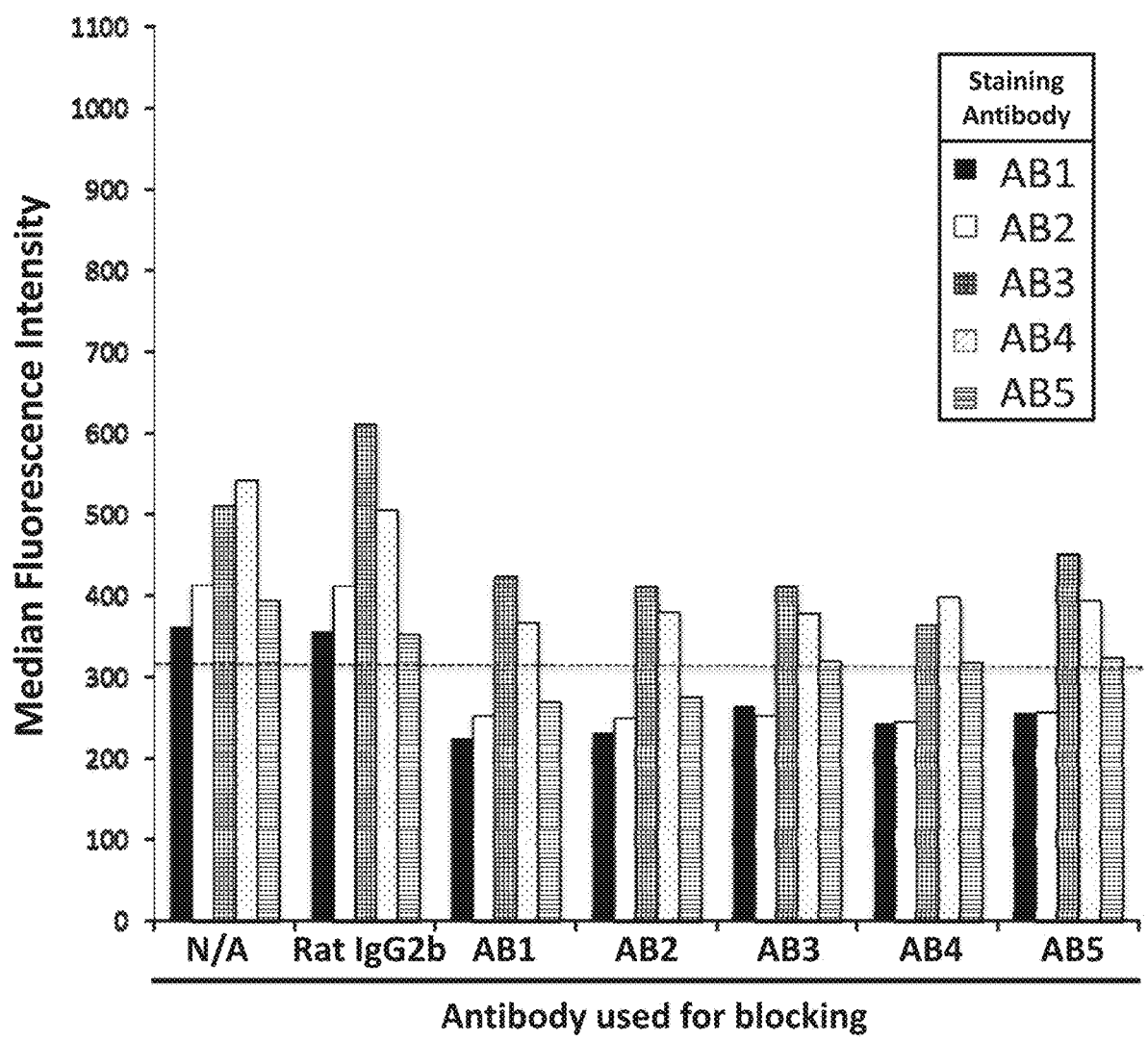

FIG. 10 shows summary of anti-TSPAN33 blocking assays on monocytes cultured overnight with CD40L (TNFSF5) plus IL-4. The x-axis indicate the antibody used to block the staining, and the bars indicates the antibody stain the monocytes; the dotted line indicates the mean fluorescence of monocytes stained with an isotype control (Mouse IgG2b, κ).

FIG. 11 shows tables presenting summaries of anti-TSPAN33 blocking assays on PBMCs activated with CD40L (TNFSF5) plus IL-4.

DETAILED DESCRIPTION

Antibody Generation and Characterization

The examples herein below describe the production of anti-TSPAN33 agents, particularly anti-TSPAN33 antibodies, with desirable properties from a therapeutic perspective including binding affinity for TSPAN33 and/or its variants. Antibody affinities may be determined as described in the examples herein below. Preferably antibodies bind TSPAN33 with a high affinity, e.g., a Kd value of no more than about $1 \times 10^{-7}$ M; preferably no more than about $1 \times 10^{-8}$ M; and preferably no more than about $5 \times 10^{-9}$ M.

Aside from antibodies with strong binding affinity for TSPAN33, it is also desirable to select chimeric, humanized or variant antibodies that have other beneficial properties from a therapeutic perspective. For example, the antibody may be one that alters tumor progression or reduces autoimmune disease severity. Assays for determining the activity of the anti-TSPAN33 antibodies of the invention are cell-based ELISA, to measure relative avidity of the antibody for the target on cells, flow cytometry, to measure cell specificity of the antibody, and cytotoxicity, to measure potential to mediate direct or indirect killing of TSPAN33-expressing target cells such as lymphoma lines or autoreactive B cells. Preferably the humanized or variant antibody fails to elicit an immunogenic response upon administration of a therapeutically effective amount of the antibody to a human patient. If an immunogenic response is elicited, preferably the response will be such that the antibody still provides a therapeutic benefit to the patient treated therewith.

In some embodiments, anti-TSPAN33 agents (e.g., anti-TSPAN33 antibodies, humanized anti-TSPAN33 antibodies) herein bind the same epitope. According to one embodiment of the invention, humanized anti-TSPAN33 antibodies bind the epitope as herein defined. To screen for antibodies that bind to the epitope on TSPAN33 bound by an antibody of interest (e.g., those that block binding of the antibody to TSPAN33), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al., J. Biol. Chem. 270:1388-1394 (1995), in Cunningham and Wells, Science 244:1081-1085 (1989) or in Davidson and Doranz, Immunology 143: 13-20 (2014), can be performed to determine whether the antibody binds an epitope of interest.

Antibodies herein generally have a heavy chain variable domain comprising an amino acid sequence represented by the formula: FRH1-CDRH1-FRH2-CDRH2-FRH3-CDRH3-FRH4, where "FRH1-4" represents the four heavy chain framework regions and "CDRH1-3" represents the three hypervariable regions of an anti-TSPAN33 antibody variable heavy domain. The antibodies of the invention have a heavy chain variable domain comprising an amino acid sequence represented by the formula: FRH1-CDRH1-FRH2-CDRH2-FRH3-CDRH3-FRH4, where "FRH1-4" represents the four heavy chain framework regions and "CDRH1-3" represents the three hypervariable regions of an anti-TSPAN33 antibody variable heavy domain. FRH1-4 may be derived from a consensus sequence (for example the most common amino acids of a class, subclass or subgroup of heavy or light chains of human immunoglobulins) or may be derived from an individual human antibody framework region or from a combination of different framework region sequences. Many human antibody framework region sequences are compiled in Kabat et al., supra, for example. In one embodiment, the variable heavy FR is provided by a consensus sequence of a human immunoglobulin subgroup as compiled by Kabat et al., supra.

The human variable heavy FR sequence may have substitutions therein, e.g. where the human FR residue is replaced by a corresponding nonhuman residue (by "corresponding nonhuman residue" is meant the nonhuman residue with the same Kabat positional numbering as the human residue of interest when the human and nonhuman sequences are aligned), but replacement with the nonhuman residue is not necessary. For example, a replacement FR residue other than the corresponding nonhuman residue may be selected by phage display.

Antibodies herein may have a light chain variable domain comprising an amino acid sequence represented by the formula: FRL1-CDRL1-FRL2-CDRL2-FRL3-CDRL3-FRL4, where "FRL1-4" represents the four framework regions and "CDRL1-3" represents the three hypervariable regions of an anti-TSPAN33 antibody variable light domain. The antibodies of the preferred embodiment herein have a light chain variable domain comprising an amino acid sequence represented by the formula: FRL1-CDRL1-FRL2-CDRL2-FRL3-CDRL3-FRL4, where "FRL1-4" represents the four framework regions and "CDRL1-3" represents the three hypervariable regions of an anti-TSPAN33 antibody variable light domain. FRL1-4 may be derived from a consensus sequence (for example the most common amino acids of a class, subclass or subgroup of heavy or light chains of human immunoglobulins) or may be derived from an individual human antibody framework region or from a combination of different framework region sequences. In one preferred embodiment, the variable light FR is provided by a consensus sequence of a human immunoglobulin subgroup as compiled by Kabat et al., supra.

The human variable light FR sequence may have substitutions therein, e.g. where the human FR residue is replaced by a corresponding mouse residue, but replacement with the nonhuman residue is not necessary. For example, a replacement residue other than the corresponding nonhuman residue may be selected by phage display. Methods for generating humanized anti-TSPAN33 antibodies of interest herein are elaborated in more detail below.

Anti-TSPAN33 Agents

Provided herein are agents that bind Tetraspanin 33 (TSPAN33). Such agents may be referred to as anti-TSPAN33 agents and may include anti-TSPAN33 antibodies, anti-TSPAN33 antibody fragments (e.g., antigen binding fragments), and anti-TSPAN33 antibody derivatives. Reference to anti-TSPAN33 antibodies herein may include anti-TSPAN33 agents, anti-TSPAN33 antibody fragments (e.g., antigen binding fragments), and anti-TSPAN33 antibody derivatives. The terms agent and antibody may be used interchangeably herein.

In some embodiments, the agent is isolated (e.g., separated from a component of its natural environment (e.g. an animal, a biological sample)). In some embodiments, the agent is non-naturally occurring (e.g., produced by human intervention). In some embodiments, the agent is a humanized antibody, or an antigen binding fragment thereof. In some embodiments, the agent is a derivative of a humanized antibody that binds TSPAN33. In some embodiments, the agent binds TSPAN33 under laboratory conditions (e.g., binds TSPAN33 in vitro, binds TSPAN33 in a flow cytometry assay, binds TSPAN33 in an ELISA, binds TSPAN33 on an isolated cell in vitro, binds TSPAN33 on an isolated cell in a flow cytometry assay, binds TSPAN33 on an isolated cell in an ELISA). In some embodiments, the agent binds TSPAN33 under physiological conditions (e.g., binds TSPAN33 on a cell in a subject).

Generally, the anti-TSPAN33 agent provided herein comprises at least one immunoglobulin heavy chain variable domain and at least one immunoglobulin light chain variable domain. In some embodiments, an anti-TSPAN33 agent herein comprises two immunoglobulin heavy chain variable domains and two immunoglobulin light chain variable domains. Typically, each immunoglobulin heavy chain variable domain of the anti-TSPAN33 agent comprises first, second, and third heavy chain complementarity determining regions (CDRs; CDRH1, CDRH2, CDRH3), and each immunoglobulin light chain variable domain of the anti-TSPAN33 agent comprises first, second, and third light chain CDRs (DCRL1, CDRL2, CDRL3).

CDRH1

In some embodiments, the first heavy chain CDR (CDRH1) of an anti-TSPAN33 agent provided herein comprises a polypeptide that is at least 75 percent identical to the amino acid sequence $X_1YX_2MX_3$ (SEQ ID NO: 41), where $X_1$ is D, S or N; $X_2$ is Y or W; and $X_3$ is N, H or T. In some embodiments, the CDRH1 comprises a polypeptide that is at least 80 percent identical to the amino acid sequence of SEQ ID NO: 41. In some embodiments, the CDRH1 comprises a polypeptide that is at least 85 percent identical to the amino acid sequence of SEQ ID NO: 41. In some embodiments, the CDRH1 comprises a polypeptide that is at least 90 percent identical to the amino acid sequence of SEQ ID NO: 41. In some embodiments, the CDRH1 comprises a polypeptide that is at least 95 percent identical to the amino acid sequence of SEQ ID NO: 41. In some embodiments, the CDRH1 comprises a polypeptide that is 100 percent identical to the amino acid sequence of SEQ ID NO: 41.

The amino acid $X_1$ of SEQ ID NO: 41 may be substituted with any amino acid. In some embodiments, the amino acid $X_1$ of SEQ ID NO: 41 is substituted with a conservative amino acid (e.g., conservative to D, S, and/or N). In some embodiments, the amino acid $X_1$ of SEQ ID NO: 41 is substituted with a polar amino acid.

The amino acid $X_2$ of SEQ ID NO: 41 may be substituted with any amino acid. In some embodiments, the amino acid $X_2$ of SEQ ID NO: 41 is substituted with a conservative amino acid (e.g., conservative to Y and/or W). In some embodiments, the amino acid $X_2$ of SEQ ID NO: 41 is substituted with an aromatic amino acid. In some embodiments, the amino acid $X_2$ of SEQ ID NO: 41 is substituted with a neutral amino acid.

The amino acid $X_3$ of SEQ ID NO: 41 may be substituted with any amino acid. In some embodiments, the amino acid $X_3$ of SEQ ID NO: 41 is substituted with a conservative amino acid (e.g., conservative to T, H and/or N). In some embodiments, the amino acid $X_3$ of SEQ ID NO: 41 is substituted with a polar amino acid. In some embodiments, the amino acid $X_3$ of SEQ ID NO: 41 is substituted with a neutral amino acid.

In some embodiments, the CDRH1 of an anti-TSPAN33 agent provided herein comprises a polypeptide that is at least 75% identical to an amino acid sequence chosen from DYYMT (SEQ ID NO: 1), SYWMH (SEQ ID NO: 9), NYYMN (SEQ ID NO: 17), NYYMN (SEQ ID NO: 25), and SYWMH (SEQ ID NO: 33). In some embodiments, the CDRH1 of an anti-TSPAN33 agent provided herein comprises a polypeptide that is at least 80% identical to an amino acid sequence chosen from DYYMT (SEQ ID NO: 1), SYWMH (SEQ ID NO: 9), NYYMN (SEQ ID NO: 17), NYYMN (SEQ ID NO: 25), and SYWMH (SEQ ID NO: 33). In some embodiments, the CDRH1 of an anti-TSPAN33 agent provided herein comprises a polypeptide that is at least 85% identical to an amino acid sequence chosen from DYYMT (SEQ ID NO: 1), SYWMH (SEQ ID NO: 9), NYYMN (SEQ ID NO: 17), NYYMN (SEQ ID NO: 25), and SYWMH (SEQ ID NO: 33). In some embodiments, the CDRH1 of an anti-TSPAN33 agent provided herein comprises a polypeptide that is at least 90% identical to an amino acid sequence chosen from DYYMT (SEQ ID NO: 1), SYWMH (SEQ ID NO: 9), NYYMN (SEQ ID NO: 17), NYYMN (SEQ ID NO: 25), and SYWMH (SEQ ID NO: 33). In some embodiments, the CDRH1 of an anti-TSPAN33 agent provided herein comprises a polypeptide that is at least 95% identical to an amino acid sequence chosen from DYYMT (SEQ ID NO: 1), SYWMH (SEQ ID NO: 9), NYYMN (SEQ ID NO: 17), NYYMN (SEQ ID NO: 25), and SYWMH (SEQ ID NO: 33). In some embodiments, the CDRH1 of an anti-TSPAN33 agent provided herein comprises an amino acid sequence chosen from DYYMT (SEQ ID NO: 1), SYWMH (SEQ ID NO: 9), NYYMN (SEQ ID NO: 17), NYYMN (SEQ ID NO: 25), and SYWMH (SEQ ID NO: 33).

CDRH2

In some embodiments, the second heavy chain CDR (CDRH2) of an anti-TSPAN33 agent provided herein comprises a polypeptide that is at least 75 percent identical to the amino acid sequence $X_1IX_2X_3X_4X_5X_6GX_7X_8X_9X_{10}YX_{11}X_{12}X_{13}X_{14}KX_{15}$ (SEQ ID NO: 42), where $X_1$ is F, R, D or E; $X_2$ is R, D, I or N; $X_3$ is N or P; $X_4$ is N or K; $X_5$ is A, S or N; $X_6$ is N or G; $X_7$ is Y or no amino acid; $X_8$ is T or no amino acid; $X_9$ is T or S; $X_{10}$ is E, K, I or N; $X_{11}$ is S or N; $X_{12}$ is A, E or Q; $X_{13}$ is S or K; $X_{14}$ is V or F; and $X_{15}$ is G, S or N. In some embodiments, the CDRH2 comprises a polypeptide that is at least 80 percent identical to the amino acid sequence of SEQ ID NO: 42. In some embodiments, the CDRH2 comprises a polypeptide that is at least 85 percent identical to the amino acid sequence of SEQ ID NO: 42. In some embodiments, the CDRH2 comprises a polypeptide that is at least 90 percent identical to the amino acid sequence of SEQ ID NO: 42. In some embodiments, the CDRH2 comprises a polypeptide that is at least 95 percent identical to the amino acid sequence of SEQ ID NO: 42. In some embodiments, the CDRH2 comprises a polypeptide that is 100 percent identical to the amino acid sequence of SEQ ID NO: 42.

The amino acid $X_1$ of SEQ ID NO: 42 may be substituted with any amino acid. In some embodiments, the amino acid $X_1$ of SEQ ID NO: 42 is substituted with a conservative amino acid (e.g., conservative to F, R, D and/or E).

The amino acid $X_2$ of SEQ ID NO: 42 may be substituted with any amino acid. In some embodiments, the amino acid $X_2$ of SEQ ID NO: 42 is substituted with a conservative amino acid (e.g., conservative to R, D, I and/or N).

The amino acid $X_3$ of SEQ ID NO: 42 may be substituted with any amino acid. In some embodiments, the amino acid $X_3$ of SEQ ID NO: 42 is substituted with a conservative amino acid (e.g., conservative to N and/or P). In some embodiments, the amino acid $X_3$ of SEQ ID NO: 42 is substituted with a neutral amino acid.

The amino acid $X_4$ of SEQ ID NO: 42 may be substituted with any amino acid. In some embodiments, the amino acid $X_4$ of SEQ ID NO: 42 is substituted with a conservative amino acid (e.g., conservative to N and/or K). In some embodiments, the amino acid $X_4$ of SEQ ID NO: 42 is substituted with a polar amino acid.

The amino acid $X_5$ of SEQ ID NO: 42 may be substituted with any amino acid. In some embodiments, the amino acid $X_5$ of SEQ ID NO: 42 is substituted with a conservative amino acid (e.g., conservative to A, S and/or N). In some embodiments, the amino acid $X_5$ of SEQ ID NO: 42 is substituted with a neutral amino acid.

The amino acid $X_6$ of SEQ ID NO: 42 may be substituted with any amino acid. In some embodiments, the amino acid $X_6$ of SEQ ID NO: 42 is substituted with a conservative amino acid (e.g., conservative to N and/or G). In some embodiments, the amino acid $X_6$ of SEQ ID NO: 42 is substituted with a neutral amino acid.

The amino acid $X_7$ of SEQ ID NO: 42 may be substituted with any amino acid. In some embodiments, the amino acid $X_7$ of SEQ ID NO: 42 is substituted with a conservative amino acid (e.g., conservative to Y). In some embodiments, the amino acid $X_7$ of SEQ ID NO: 42 is substituted with a neutral amino acid. In some embodiments, the amino acid $X_7$ of SEQ ID NO: 42 is substituted with a polar amino acid. In some embodiments, the amino acid $X_7$ of SEQ ID NO: 42 is substituted with an aromatic amino acid.

The amino acid $X_8$ of SEQ ID NO: 42 may be substituted with any amino acid. In some embodiments, the amino acid $X_8$ of SEQ ID NO: 42 is substituted with a conservative amino acid (e.g., conservative to T). In some embodiments, the amino acid $X_8$ of SEQ ID NO: 42 is substituted with a neutral amino acid. In some embodiments, the amino acid $X_8$ of SEQ ID NO: 42 is substituted with a polar amino acid. In some embodiments, the amino acid $X_8$ of SEQ ID NO: 42 is substituted with a hydroxyl-containing amino acid.

The amino acid $X_9$ of SEQ ID NO: 42 may be substituted with any amino acid. In some embodiments, the amino acid $X_9$ of SEQ ID NO: 42 is substituted with a conservative amino acid (e.g., conservative to T and/or S). In some embodiments, the amino acid $X_9$ of SEQ ID NO: 42 is substituted with a neutral amino acid. In some embodiments, the amino acid $X_9$ of SEQ ID NO: 42 is substituted with a polar amino acid. In some embodiments, the amino acid $X_9$ of SEQ ID NO: 42 is substituted with a hydroxyl-containing amino acid.

The amino acid $X_{10}$ of SEQ ID NO: 42 may be substituted with any amino acid. In some embodiments, the amino acid $X_{10}$ of SEQ ID NO: 42 is substituted with a conservative amino acid (e.g., conservative to E, K, I and/or N).

The amino acid $X_{11}$ of SEQ ID NO: 42 may be substituted with any amino acid. In some embodiments, the amino acid $X_{11}$ of SEQ ID NO: 42 is substituted with a conservative amino acid (e.g., conservative to S and/or N). In some embodiments, the amino acid $X_{11}$ of SEQ ID NO: 42 is substituted with a neutral amino acid. In some embodiments, the amino acid $X_{11}$ of SEQ ID NO: 42 is substituted with a polar amino acid.

The amino acid $X_{12}$ of SEQ ID NO: 42 may be substituted with any amino acid. In some embodiments, the amino acid $X_{12}$ of SEQ ID NO: 42 is substituted with a conservative amino acid (e.g., conservative to A, E and/or Q).

The amino acid $X_{13}$ of SEQ ID NO: 42 may be substituted with any amino acid. In some embodiments, the amino acid $X_{13}$ of SEQ ID NO: 42 is substituted with a conservative amino acid (e.g., conservative to S and/or K). In some embodiments, the amino acid $X_{13}$ of SEQ ID NO: 42 is substituted with a polar amino acid.

The amino acid $X_{14}$ of SEQ ID NO: 42 may be substituted with any amino acid. In some embodiments, the amino acid $X_{14}$ of SEQ ID NO: 42 is substituted with a conservative amino acid (e.g., conservative to V and/or F). In some embodiments, the amino acid $X_{14}$ of SEQ ID NO: 42 is substituted with a neutral amino acid. In some embodiments, the amino acid $X_{14}$ of SEQ ID NO: 42 is substituted with a nonpolar amino acid.

The amino acid $X_{15}$ of SEQ ID NO: 42 may be substituted with any amino acid. In some embodiments, the amino acid $X_{15}$ of SEQ ID NO: 42 is substituted with a conservative amino acid (e.g., conservative to G, S and/or N). In some embodiments, the amino acid $X_{15}$ of SEQ ID NO: 42 is substituted with a neutral amino acid.

In some embodiments, the CDRH2 of an anti-TSPAN33 agent provided herein comprises a polypeptide that is at least 75% identical to an amino acid sequence chosen from FIRNKANGYTTEYSASVKG (SEQ ID NO: 2), RIDPNSGGTKYNEKFKS (SEQ ID NO: 10), DIIPNNGGTIYNQKFKG (SEQ ID NO: 18), DIIPNNGGTIYNQKFKG (SEQ ID NO: 26), and EINPNNGGSNYNEKFKN (SEQ ID NO: 34). In some embodiments, the CDRH2 of an anti-TSPAN33 agent provided herein comprises a polypeptide that is at least 80% identical to an amino acid sequence chosen from FIRNK-ANGYTTEYSASVKG (SEQ ID NO: 2), RIDPNSGGT- KYNEKFKS (SEQ ID NO: 10), DIIPNNGGTIYNQKFKG (SEQ ID NO: 18), DIIPNNGGTIYNQKFKG (SEQ ID NO: 26), and EINPNNGGSNYNEKFKN (SEQ ID NO: 34). In some embodiments, the CDRH2 of an anti-TSPAN33 agent provided herein comprises a polypeptide that is at least 85% identical to an amino acid sequence chosen from FIRNKANGYTTEYSASVKG (SEQ ID NO: 2), RIDPNSGGTKYNEKFKS (SEQ ID NO: 10), DIIPNNGGTIYNQKFKG (SEQ ID NO: 18), DIIPNNGGTIYNQKFKG (SEQ ID NO: 26), and EINPNNGGSNYNEKFKN (SEQ ID NO: 34). In some embodiments, the CDRH2 of an anti-TSPAN33 agent provided herein comprises a polypeptide that is at least 90% identical to an amino acid sequence chosen from FIRNKANGYTTEYSASVKG (SEQ ID NO: 2), RIDPNSGGTKYNEKFKS (SEQ ID NO: 10), DIIPNNGGTIYNQKFKG (SEQ ID NO: 18), DIIPNNGGTIYNQKFKG (SEQ ID NO: 26), and EINPNNGGSNYNEKFKN (SEQ ID NO: 34). In some embodiments, the CDRH2 of an anti-TSPAN33 agent provided herein comprises a polypeptide that is at least 95% identical to an amino acid sequence chosen from FIRNKANGYTTEYSASVKG (SEQ ID NO: 2), RIDPNSGGTKYNEKFKS (SEQ ID NO: 10), DIIPNNGGTIYNQKFKG (SEQ ID NO: 18), DIIPNNGGTIYNQKFKG (SEQ ID NO: 26), and EINPNNGGSNYNEKFKN (SEQ ID NO: 34). In some embodiments, the CDRH2 of an anti-TSPAN33 agent provided herein comprises an amino acid sequence chosen from FIRNKANGYTTEYSASVKG (SEQ ID NO: 2), RIDPNSGGTKYNEKFKS (SEQ ID NO: 10), DIIPNNGGTIYNQKFKG (SEQ ID NO: 18), DIIPNNGGTIYNQKFKG (SEQ ID NO: 26), and EINPNNGGSNYNEKFKN (SEQ ID NO: 34).

CDRH3

In some embodiments, the third heavy chain CDR (CDRH3) of an anti-TSPAN33 agent provided herein comprises a polypeptide that is at least 75 percent identical to the amino acid sequence $X_1X_2X_3X_4X_5X_6X_7FDX_8$ (SEQ ID NO: 43), where $X_1$ is no amino acid or 5; $X_2$ is Y, F or R; $X_3$ is L, I or Y; $X_4$ is Q, I, W or S; $X_5$ is T, S or Y; $X_6$ is G or W; $X_7$ is N or Y; and $X_8$ is Y or V. In some embodiments, the CDRH3 comprises a polypeptide that is at least 80 percent identical to the amino acid sequence of SEQ ID NO: 43. In some embodiments, the CDRH3 comprises a polypeptide that is at least 85 percent identical to the amino acid sequence of SEQ ID NO: 43. In some embodiments, the CDRH3 comprises a polypeptide that is at least 90 percent identical to the amino acid sequence of SEQ ID NO: 43. In some embodiments, the CDRH3 comprises a polypeptide that is at least 95 percent identical to the amino acid sequence of SEQ ID NO: 43. In some embodiments, the CDRH3 comprises a polypeptide that is 100 percent identical to the amino acid sequence of SEQ ID NO: 43.

The amino acid $X_1$ of SEQ ID NO: 43 may be substituted with any amino acid. In some embodiments, the amino acid $X_1$ of SEQ ID NO: 43 is substituted with a conservative amino acid (e.g., conservative to S). In some embodiments, the amino acid $X_1$ of SEQ ID NO: 43 is substituted with a neutral amino acid. In some embodiments, the amino acid $X_1$ of SEQ ID NO: 43 is substituted with a polar amino acid. In some embodiments, the amino acid $X_1$ of SEQ ID NO: 43 is substituted with a hydroxyl-containing amino acid.

The amino acid $X_2$ of SEQ ID NO: 43 may be substituted with any amino acid. In some embodiments, the amino acid $X_2$ of SEQ ID NO: 43 is substituted with a conservative amino acid (e.g., conservative to Y, F and/or R).

The amino acid $X_3$ of SEQ ID NO: 43 may be substituted with any amino acid. In some embodiments, the amino acid $X_3$ of SEQ ID NO: 43 is substituted with a conservative amino acid (e.g., conservative to L, I and/or Y). In some embodiments, the amino acid $X_3$ of SEQ ID NO: 43 is substituted with a neutral amino acid.

The amino acid $X_4$ of SEQ ID NO: 43 may be substituted with any amino acid. In some embodiments, the amino acid $X_4$ of SEQ ID NO: 43 is substituted with a conservative amino acid (e.g., conservative to Q, I, W and/or S). In some embodiments, the amino acid $X_4$ of SEQ ID NO: 43 is substituted with a neutral amino acid.

The amino acid $X_5$ of SEQ ID NO: 43 may be substituted with any amino acid. In some embodiments, the amino acid $X_5$ of SEQ ID NO: 43 is substituted with a conservative amino acid (e.g., conservative to T, S and/or Y). In some embodiments, the amino acid $X_5$ of SEQ ID NO: 43 is substituted with a neutral amino acid. In some embodiments, the amino acid $X_5$ of SEQ ID NO: 43 is substituted with a polar amino acid.

The amino acid $X_6$ of SEQ ID NO: 43 may be substituted with any amino acid. In some embodiments, the amino acid $X_6$ of SEQ ID NO: 43 is substituted with a conservative amino acid (e.g., conservative to G and/or W). In some embodiments, the amino acid $X_6$ of SEQ ID NO: 43 is substituted with a neutral amino acid. In some embodiments, the amino acid $X_6$ of SEQ ID NO: 43 is substituted with a nonpolar amino acid.

The amino acid $X_7$ of SEQ ID NO: 43 may be substituted with any amino acid. In some embodiments, the amino acid $X_7$ of SEQ ID NO: 43 is substituted with a conservative amino acid (e.g., conservative to N and/or Y). In some embodiments, the amino acid $X_7$ of SEQ ID NO: 43 is substituted with a polar amino acid. In some embodiments, the amino acid $X_7$ of SEQ ID NO: 43 is substituted with a neutral amino acid.

The amino acid $X_8$ of SEQ ID NO: 43 may be substituted with any amino acid. In some embodiments, the amino acid $X_8$ of SEQ ID NO: 43 is substituted with a conservative amino acid (e.g., conservative to Y and/or V). In some embodiments, the amino acid $X_8$ of SEQ ID NO: 43 is substituted with a neutral amino acid.

In some embodiments, the CDRH3 of an anti-TSPAN33 agent provided herein comprises a polypeptide that is at least 75% identical to an amino acid sequence chosen from YLQTGNFDY (SEQ ID NO: 3), FIITGYFDY (SEQ ID NO: 11), RLWSWYFDV (SEQ ID NO: 19), RLWSWYFDV (SEQ ID NO: 22), and SYYSYWYFDY (SEQ ID NO: 35). In some embodiments, the CDRH3 of an anti-TSPAN33 agent provided herein comprises a polypeptide that is at least 80% identical to an amino acid sequence chosen from YLQTGNFDY (SEQ ID NO: 3), FIITGYFDY (SEQ ID NO: 11), RLWSWYFDV (SEQ ID NO: 19), RLWSWYFDV (SEQ ID NO: 22), and SYYSYWYFDY (SEQ ID NO: 35). In some embodiments, the CDRH3 of an anti-TSPAN33 agent provided herein comprises a polypeptide that is at least 85% identical to an amino acid sequence chosen from YLQTGNFDY (SEQ ID NO: 3), FIITGYFDY (SEQ ID NO: 11), RLWSWYFDV (SEQ ID NO: 19), RLWSWYFDV (SEQ ID NO: 22), and SYYSYWYFDY (SEQ ID NO: 35). In some embodiments, the CDRH3 of an anti-TSPAN33 agent provided herein comprises a polypeptide that is at least 90% identical to an amino acid sequence chosen from YLQTGNFDY (SEQ ID NO: 3), FIITGYFDY (SEQ ID NO: 11), RLWSWYFDV (SEQ ID NO: 19), RLWSWYFDV (SEQ ID NO: 22), and SYYSYWYFDY (SEQ ID NO: 35). In some embodiments, the CDRH3 of an anti-TSPAN33 agent provided herein comprises a polypeptide that is at least 95% identical to an amino acid sequence chosen from YLQTGNFDY (SEQ ID NO: 3), FIITGYFDY (SEQ ID NO:

11), RLWSWYFDV (SEQ ID NO: 19), RLWSWYFDV (SEQ ID NO: 22), and SYYSYWYFDY (SEQ ID NO: 35). In some embodiments, the CDRH3 of an anti-TSPAN33 agent provided herein comprises an amino acid sequence chosen from YLQTGNFDY (SEQ ID NO: 3), FIITGYFDY (SEQ ID NO: 11), RLWSWYFDV (SEQ ID NO: 19), RLWSWYFDV (SEQ ID NO: 22), and SYYSYWYFDY (SEQ ID NO: 35).

CDRL1

In some embodiments, the first light chain CDR (CDRL1) of an anti-TSPAN33 agent provided herein comprises a polypeptide that is at least 75 percent identical to the amino acid sequence $X_1ASX_2X_3X_4X_5X_6X_7X_8X_9$ (SEQ ID NO: 44), where $X_1$ is R, K or S; $X_2$ is Q or S; $X_3$ is D or S; $X_4$ is I or V; $X_5$ is S, G or N; $X_6$ is N, A or no amino acid; $X_7$ is F, A or Y; $X_8$ is L, V or M; and $X_9$ is N, A, Y or H. In some embodiments, the CDRL1 comprises a polypeptide that is at least 80 percent identical to the amino acid sequence of SEQ ID NO: 44. In some embodiments, the CDRL1 comprises a polypeptide that is at least 85 percent identical to the amino acid sequence of SEQ ID NO: 44. In some embodiments, the CDRL1 comprises a polypeptide that is at least 90 percent identical to the amino acid sequence of SEQ ID NO: 44. In some embodiments, the CDRL1 comprises a polypeptide that is at least 95 percent identical to the amino acid sequence of SEQ ID NO: 44. In some embodiments, the CDRL1 comprises a polypeptide that is 100 percent identical to the amino acid sequence of SEQ ID NO: 44.

The amino acid $X_1$ of SEQ ID NO: 44 may be substituted with any amino acid. In some embodiments, the amino acid $X_1$ of SEQ ID NO: 44 is substituted with a conservative amino acid (e.g., conservative to R, K and/or S). In some embodiments, the amino acid $X_1$ of SEQ ID NO: 44 is substituted with a polar amino acid.

The amino acid $X_2$ of SEQ ID NO: 44 may be substituted with any amino acid. In some embodiments, the amino acid $X_2$ of SEQ ID NO: 44 is substituted with a conservative amino acid (e.g., conservative to Q and/or S). In some embodiments, the amino acid $X_2$ of SEQ ID NO: 44 is substituted with a neutral amino acid. In some embodiments, the amino acid $X_2$ of SEQ ID NO: 44 is substituted with a polar amino acid.

The amino acid $X_3$ of SEQ ID NO: 44 may be substituted with any amino acid. In some embodiments, the amino acid $X_3$ of SEQ ID NO: 44 is substituted with a conservative amino acid (e.g., conservative to D and/or S). In some embodiments, the amino acid $X_3$ of SEQ ID NO: 44 is substituted with a polar amino acid.

The amino acid $X_4$ of SEQ ID NO: 44 may be substituted with any amino acid. In some embodiments, the amino acid $X_4$ of SEQ ID NO: 44 is substituted with a conservative amino acid (e.g., conservative to I and/or V). In some embodiments, the amino acid $X_4$ of SEQ ID NO: 44 is substituted with a neutral amino acid. In some embodiments, the amino acid $X_4$ of SEQ ID NO: 44 is substituted with a polar amino acid. In some embodiments, the amino acid $X_4$ of SEQ ID NO: 44 is substituted with an aliphatic amino acid.

The amino acid $X_5$ of SEQ ID NO: 44 may be substituted with any amino acid. In some embodiments, the amino acid $X_5$ of SEQ ID NO: 44 is substituted with a conservative amino acid (e.g., conservative to S, G and/or N). In some embodiments, the amino acid $X_5$ of SEQ ID NO: 44 is substituted with a neutral amino acid.

The amino acid $X_6$ of SEQ ID NO: 44 may be substituted with any amino acid. In some embodiments, the amino acid $X_6$ of SEQ ID NO: 44 is substituted with a conservative amino acid (e.g., conservative to N and/or A). In some embodiments, the amino acid $X_6$ of SEQ ID NO: 44 is substituted with a neutral amino acid.

The amino acid $X_7$ of SEQ ID NO: 44 may be substituted with any amino acid. In some embodiments, the amino acid $X_7$ of SEQ ID NO: 44 is substituted with a conservative amino acid (e.g., conservative to F, A and/or Y). In some embodiments, the amino acid $X_7$ of SEQ ID NO: 44 is substituted with a neutral amino acid.

The amino acid $X_8$ of SEQ ID NO: 44 may be substituted with any amino acid. In some embodiments, the amino acid $X_8$ of SEQ ID NO: 44 is substituted with a conservative amino acid (e.g., conservative to L, V and/or M). In some embodiments, the amino acid $X_8$ of SEQ ID NO: 44 is substituted with a neutral amino acid. In some embodiments, the amino acid $X_8$ of SEQ ID NO: 44 is substituted with a nonpolar amino acid.

The amino acid $X_9$ of SEQ ID NO: 44 may be substituted with any amino acid. In some embodiments, the amino acid $X_9$ of SEQ ID NO: 44 is substituted with a conservative amino acid (e.g., conservative to N, A, Y and/or H). In some embodiments, the amino acid $X_9$ of SEQ ID NO: 44 is substituted with a neutral amino acid.

In some embodiments, the CDRL1 of an anti-TSPAN33 agent provided herein comprises a polypeptide that is at least 75% identical to an amino acid sequence chosen from RASQDISNFLN (SEQ ID NO: 5), KASQDVGAAVA (SEQ ID NO: 13), SASSSVSYMY (SEQ ID NO: 21), SASSSVSYMY (SEQ ID NO: 29), and SASSSVNYMH (SEQ ID NO: 37). In some embodiments, the CDRL1 of an anti-TSPAN33 agent provided herein comprises a polypeptide that is at least 80% identical to an amino acid sequence chosen from RASQDISNFLN (SEQ ID NO: 5), KASQDVGAAVA (SEQ ID NO: 13), SASSSVSYMY (SEQ ID NO: 21), SASSSVSYMY (SEQ ID NO: 29), and SASSSVNYMH (SEQ ID NO: 37). In some embodiments, the CDRL1 of an anti-TSPAN33 agent provided herein comprises a polypeptide that is at least 85% identical to an amino acid sequence chosen from RASQDISNFLN (SEQ ID NO: 5), KASQDVGAAVA (SEQ ID NO: 13), SASSSVSYMY (SEQ ID NO: 21), SASSSVSYMY (SEQ ID NO: 29), and SASSSVNYMH (SEQ ID NO: 37). In some embodiments, the CDRL1 of an anti-TSPAN33 agent provided herein comprises a polypeptide that is at least 90% identical to an amino acid sequence chosen from RASQDISNFLN (SEQ ID NO: 5), KASQDVGAAVA (SEQ ID NO: 13), SASSSVSYMY (SEQ ID NO: 21), SASSSVSYMY (SEQ ID NO: 29), and SASSSVNYMH (SEQ ID NO: 37). In some embodiments, the CDRL1 of an anti-TSPAN33 agent provided herein comprises a polypeptide that is at least 95% identical to an amino acid sequence chosen from RASQDISNFLN (SEQ ID NO: 5), KASQDVGAAVA (SEQ ID NO: 13), SASSSVSYMY (SEQ ID NO: 21), SASSSVSYMY (SEQ ID NO: 29), and SASSSVNYMH (SEQ ID NO: 37). In some embodiments, the CDRL1 of an anti-TSPAN33 agent provided herein comprises an amino acid sequence chosen from RASQDISNFLN (SEQ ID NO: 5), KASQDVGAAVA (SEQ ID NO: 13), SASSSVSYMY (SEQ ID NO: 21), SASSSVSYMY (SEQ ID NO: 29), and SASSSVNYMH (SEQ ID NO: 37).

CDRL2

In some embodiments, the second light chain CDR (CDRL2) of an anti-TSPAN33 agent provided herein comprises a polypeptide that is at least 80 percent identical to the amino acid sequence $X_1X_2SX_3X_4X_5X_6$ (SEQ ID NO: 45), where $X_1$ is F, W, L or D; $X_2$ is T or A; $X_3$ is R, T, N or K; $X_4$ is L or R; $X_5$ is H or A; and $X_6$ is S, T or P. In some embodiments, the CDRL2 comprises a polypeptide that is at least 80 percent identical to the amino acid sequence of SEQ ID NO: 45. In some embodiments, the CDRL2 comprises a polypeptide that is at least 85 percent identical to the amino acid sequence of SEQ ID NO: 45. In some embodiments, the CDRL2 comprises a polypeptide that is at least 90 percent identical to the amino acid sequence of SEQ ID NO: 45. In some embodiments, the CDRL2 comprises a polypeptide that is at least 95 percent identical to the amino acid sequence of SEQ ID NO: 45. In some embodiments, the CDRL2 comprises a polypeptide that is 100 percent identical to the amino acid sequence of SEQ ID NO: 45.

The amino acid $X_1$ of SEQ ID NO: 45 may be substituted with any amino acid. In some embodiments, the amino acid $X_1$ of SEQ ID NO: 45 is substituted with a conservative amino acid (e.g., conservative to F, W, L and/or D).

The amino acid $X_2$ of SEQ ID NO: 45 may be substituted with any amino acid. In some embodiments, the amino acid $X_2$ of SEQ ID NO: 45 is substituted with a conservative amino acid (e.g., conservative to A and/or T). In some embodiments, the amino acid $X_2$ of SEQ ID NO: 45 is substituted with a neutral amino acid.

The amino acid $X_3$ of SEQ ID NO: 45 may be substituted with any amino acid. In some embodiments, the amino acid $X_3$ of SEQ ID NO: 45 is substituted with a conservative amino acid (e.g., conservative to R, T, N and/or K). In some embodiments, the amino acid $X_3$ of SEQ ID NO: 45 is substituted with a polar amino acid.

The amino acid $X_4$ of SEQ ID NO: 45 may be substituted with any amino acid. In some embodiments, the amino acid $X_4$ of SEQ ID NO: 45 is substituted with a conservative amino acid (e.g., conservative to L and/or R).

The amino acid $X_5$ of SEQ ID NO: 45 may be substituted with any amino acid. In some embodiments, the amino acid $X_5$ of SEQ ID NO: 45 is substituted with a conservative amino acid (e.g., conservative to H and/or A). In some embodiments, the amino acid $X_5$ of SEQ ID NO: 45 is substituted with a neutral amino acid.

The amino acid $X_6$ of SEQ ID NO: 45 may be substituted with any amino acid. In some embodiments, the amino acid $X_6$ of SEQ ID NO: 45 is substituted with a conservative amino acid (e.g., conservative to S, T and/or P). In some embodiments, the amino acid $X_6$ of SEQ ID NO: 45 is substituted with a neutral amino acid.

In some embodiments, the CDRL2 of an anti-TSPAN33 agent provided herein comprises a polypeptide that is at least 75% identical to an amino acid sequence chosen from FTSRLHS (SEQ ID NO: 6), WASTRHT (SEQ ID NO: 14), LTSNLAS (SEQ ID NO: 22), LTSNLAS (SEQ ID NO: 30), and DTSKLAP (SEQ ID NO: 38). In some embodiments, the CDRL2 of an anti-TSPAN33 agent provided herein comprises a polypeptide that is at least 80% identical to an amino acid sequence chosen from FTSRLHS (SEQ ID NO: 6), WASTRHT (SEQ ID NO: 14), LTSNLAS (SEQ ID NO: 22), LTSNLAS (SEQ ID NO: 30), and DTSKLAP (SEQ ID NO: 38). In some embodiments, the CDRL2 of an anti-TSPAN33 agent provided herein comprises a polypeptide that is at least 85% identical to an amino acid sequence chosen from FTSRLHS (SEQ ID NO: 6), WASTRHT (SEQ ID NO: 14), LTSNLAS (SEQ ID NO: 22), LTSNLAS (SEQ ID NO: 30), and DTSKLAP (SEQ ID NO: 38). In some embodiments, the CDRL2 of an anti-TSPAN33 agent provided herein comprises a polypeptide that is at least 90% identical to an amino acid sequence chosen from FTSRLHS (SEQ ID NO: 6), WASTRHT (SEQ ID NO: 14), LTSNLAS (SEQ ID NO: 22), LTSNLAS (SEQ ID NO: 30), and DTSKLAP (SEQ ID NO: 38). In some embodiments, the CDRL2 of an anti-TSPAN33 agent provided herein comprises a polypeptide that is at least 95% identical to an amino acid sequence chosen from FTSRLHS (SEQ ID NO: 6), WASTRHT (SEQ ID NO: 14), LTSNLAS (SEQ ID NO: 22), LTSNLAS (SEQ ID NO: 30), and DTSKLAP (SEQ ID NO: 38). In some embodiments, the CDRL2 of an anti-TSPAN33 agent provided herein comprises an amino acid sequence chosen from FTSRLHS (SEQ ID NO: 6), WASTRHT (SEQ ID NO: 14), LTSNLAS (SEQ ID NO: 22), LTSNLAS (SEQ ID NO: 30), and DTSKLAP (SEQ ID NO: 38).

CDRL3

In some embodiments, the third light chain CDR (CDRL3) of an anti-TSPAN33 agent provided herein comprises a polypeptide that is at least 80 percent identical to the amino acid sequence $X_1QX_2X_3X_4X_5PX_6T$ (SEQ ID NO: 46), where $X_1$ is Q or H; $X_2$ is G, Y or W; $X_3$ is Y, R, S or N; $X_4$ is T, S or N; $X_5$ is V, Y or N; and $X_6$ is P, F or Y. In some embodiments, the CDRL3 comprises a polypeptide that is at least 80 percent identical to the amino acid sequence of SEQ ID NO: 46. In some embodiments, the CDRL3 comprises a polypeptide that is at least 85 percent identical to the amino acid sequence of SEQ ID NO: 46. In some embodiments, the CDRL3 comprises a polypeptide that is at least 90 percent identical to the amino acid sequence of SEQ ID NO: 46. In some embodiments, the CDRL3 comprises a polypeptide that is at least 95 percent identical to the amino acid sequence of SEQ ID NO: 46. In some embodiments, the CDRL3 comprises a polypeptide that is 100 percent identical to the amino acid sequence of SEQ ID NO: 46.

The amino acid $X_1$ of SEQ ID NO: 46 may be substituted with any amino acid. In some embodiments, the amino acid $X_1$ of SEQ ID NO: 46 is substituted with a conservative amino acid (e.g., conservative to Q and/or H). In some embodiments, the amino acid $X_1$ of SEQ ID NO: 46 is substituted with a neutral amino acid. In some embodiments, the amino acid $X_1$ of SEQ ID NO: 46 is substituted with a polar amino acid.

The amino acid $X_2$ of SEQ ID NO: 46 may be substituted with any amino acid. In some embodiments, the amino acid $X_2$ of SEQ ID NO: 46 is substituted with a conservative amino acid (e.g., conservative to G, Y and/or W). In some embodiments, the amino acid $X_2$ of SEQ ID NO: 46 is substituted with a neutral amino acid.

The amino acid $X_3$ of SEQ ID NO: 46 may be substituted with any amino acid. In some embodiments, the amino acid $X_3$ of SEQ ID NO: 46 is substituted with a conservative amino acid (e.g., conservative to Y, R, S and/or N). In some embodiments, the amino acid $X_3$ of SEQ ID NO: 46 is substituted with a polar amino acid.

The amino acid $X_4$ of SEQ ID NO: 46 may be substituted with any amino acid. In some embodiments, the amino acid $X_4$ of SEQ ID NO: 46 is substituted with a conservative amino acid (e.g., conservative to T, S and/or N). In some embodiments, the amino acid $X_4$ of SEQ ID NO: 46 is substituted with a neutral amino acid. In some embodiments, the amino acid $X_4$ of SEQ ID NO: 46 is substituted with a polar amino acid.

The amino acid $X_5$ of SEQ ID NO: 46 may be substituted with any amino acid. In some embodiments, the amino acid $X_5$ of SEQ ID NO: 46 is substituted with a conservative amino acid (e.g., conservative to V, Y and/or N). In some embodiments, the amino acid $X_5$ of SEQ ID NO: 46 is substituted with a neutral amino acid.

The amino acid $X_6$ of SEQ ID NO: 46 may be substituted with any amino acid. In some embodiments, the amino acid $X_6$ of SEQ ID NO: 46 is substituted with a conservative amino acid (e.g., conservative to P, F and/or Y). In some embodiments, the amino acid $X_6$ of SEQ ID NO: 46 is substituted with a neutral amino acid.

In some embodiments, the CDRL3 of an anti-TSPAN33 agent provided herein comprises a polypeptide that is at least 75% identical to an amino acid sequence chosen from QQGYTVPPT (SEQ ID NO: 7), HQYRTYPFT (SEQ ID NO: 15), QQWSSNPYT (SEQ ID NO: 23), QQWSSNPYT (SEQ ID NO: 31), and HQWNNYPYT (SEQ ID NO: 39). In some embodiments, the CDRL3 of an anti-TSPAN33 agent provided herein comprises a polypeptide that is at least 80% identical to an amino acid sequence chosen from QQGYTVPPT (SEQ ID NO: 7), HQYRTYPFT (SEQ ID NO: 15), QQWSSNPYT (SEQ ID NO: 23), QQWSSNPYT (SEQ ID NO: 31), and HQWNNYPYT (SEQ ID NO: 39). In some embodiments, the CDRL3 of an anti-TSPAN33 agent provided herein comprises a polypeptide that is at least 85% identical to an amino acid sequence chosen from QQGYTVPPT (SEQ ID NO: 7), HQYRTYPFT (SEQ ID NO: 15), QQWSSNPYT (SEQ ID NO: 23), QQWSSNPYT (SEQ ID NO: 31), and HQWNNYPYT (SEQ ID NO: 39). In some embodiments, the CDRL3 of an anti-TSPAN33 agent provided herein comprises a polypeptide that is at least 90% identical to an amino acid sequence chosen from QQGYTVPPT (SEQ ID NO: 7), HQYRTYPFT (SEQ ID NO: 15), QQWSSNPYT (SEQ ID NO: 23), QQWSSNPYT (SEQ ID NO: 31), and HQWNNYPYT (SEQ ID NO: 39). In some embodiments, the CDRL3 of an anti-TSPAN33 agent provided herein comprises a polypeptide that is at least 95% identical to an amino acid sequence chosen from QQGYTVPPT (SEQ ID NO: 7), HQYRTYPFT (SEQ ID NO: 15), QQWSSNPYT (SEQ ID NO: 23), QQWSSNPYT (SEQ ID NO: 31), and HQWNNYPYT (SEQ ID NO: 39). In some embodiments, the CDRL3 of an anti-TSPAN33 agent provided herein comprises an amino acid sequence chosen from QQGYTVPPT (SEQ ID NO: 7), HQYRTYPFT (SEQ ID NO: 15), QQWSSNPYT (SEQ ID NO: 23), QQWSSNPYT (SEQ ID NO: 31), and HQWNNYPYT (SEQ ID NO: 39).

CDR Sets

In some embodiments, an anti-TSPAN33 agent comprises an immunoglobulin heavy chain variable domain comprising a set of CDRs (i.e., CDRH1, CDRH2, CDRH3); and an immunoglobulin light chain variable domain comprising a set of CDRs (i.e., CDRL1, CDRL2, CDRL3). In some embodiments, an anti-TSPAN33 agent herein comprises two immunoglobulin heavy chain variable domains each comprising a set of CDRs (i.e., CDRH1, CDRH2, CDRH3); and two immunoglobulin light chain variable domains each comprising a set of CDRs (i.e., CDRL1, CDRL2, CDRL3). Sets of CDRs may comprise any combination of CDR amino acid sequences (i.e., CDRH1, CDRH2, CDRH3; and CDRL1, CDRL2, CDRL3) provided herein. In some embodiments, an immunoglobulin heavy chain variable domain comprises a set of CDRH1, CDRH2 and CDRH3 amino acid sequences, and an immunoglobulin light chain variable domain comprises a set of CDRL1, CDRL2 and CDRL3 amino acid sequences chosen from sets 1-4 provided in the table below. For an anti-TSPAN33 agent comprising two immunoglobulin heavy chain variable domains and two immunoglobulin light chain variable domains, each immunoglobulin heavy chain variable domain may comprise a set of CDRH1, CDRH2 and CDRH3 amino acid sequences, and each immunoglobulin light chain variable domain may comprise a set of CDRL1, CDRL2 and CDRL3 amino acid sequences chosen from sets 1-4 provided in the following table.

| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| 1 | DYYMT (1) | FIRNKANGYTTEYSASVKG (2) | YLQTGNFDY (3) | RASQDISNFLN (5) | FTSRLHS (6) | QQGYTVPPT (7) |
| 2 | SYVVMH (9) | RIDPNSGGTKYNEKFKS (10) | FIITGYFDY (11) | KASQDVGAAVA (13) | WASTRHT (14) | HQYRTYPFT (15) |
| 3 | NYYMN (17 and 25) | DIIPNNGGTIYNQKFKG (18 and 26) | RLWSVVYFDV (19 and 27) | SASSSVSYMY (21 and 29) | LTSNLAS (22 and 30) | QQWSSNPYT (23 and 31) |
| 4 | SYVVMH (33) | EINPNNGGSNYNEKFKN (34) | SYYSYVVYFDY (35) | SASSSVNYMH (37) | DTSKLAP (38) | HQWNNYPYT (39) |

In some embodiments, all CDRs are from the same set. For example, for an anti-TSPAN33 agent comprising two immunoglobulin heavy chain variable domains and two immunoglobulin light chain variable domains, each immunoglobulin heavy chain variable domain may comprise a set of CDRH1, CDRH2 and CDRH3 amino acid sequences from set 1, and each immunoglobulin light chain variable domain may comprise a set of CDRL1, CDRL2 and CDRL3 amino acid sequences from set 1.

In some embodiments, CDRs are from the different sets. For example, for an anti-TSPAN33 agent comprising two immunoglobulin heavy chain variable domains and two immunoglobulin light chain variable domains, each immunoglobulin heavy chain variable domain may comprise a set of CDRH1, CDRH2 and CDRH3 amino acid sequences from set 1, and each immunoglobulin light chain variable domain may comprise a set of CDRL1, CDRL2 and CDRL3 amino acid sequences from set 2. In another example, for an anti-TSPAN33 agent comprising two immunoglobulin heavy chain variable domains and two immunoglobulin light chain variable domains, one immunoglobulin heavy chain variable domain may comprise a set of CDRH1, CDRH2 and CDRH3 amino acid sequences from set 1 and the other immunoglobulin heavy chain variable domain may comprise a set of CDRH1, CDRH2 and CDRH3 amino acid sequences from set 2; and one immunoglobulin light chain variable domain may comprise a set of CDRL1, CDRL2 and CDRL3 amino acid sequences from set 1 and the other immunoglobulin light chain variable domain may comprise a set of CDRL1, CDRL2 and CDRL3 amino acid sequences from set 2.

Variable Heavy Chain

In some embodiments, the variable heavy chain of an anti-TSPAN33 agent provided herein comprises a polypeptide that is at least 75% identical to the amino acid sequence of SEQ ID NO: 4. In some embodiments, the variable heavy chain of an anti-TSPAN33 agent provided herein comprises a polypeptide that is at least 80% identical to the amino acid sequence of SEQ ID NO: 4. In some embodiments, the variable heavy chain of an anti-TSPAN33 agent provided herein comprises a polypeptide that is at least 85% identical to the amino acid sequence of SEQ ID NO: 4. In some embodiments, the variable heavy chain of an anti-TSPAN33 agent provided herein comprises a polypeptide that is at least 90% identical to the amino acid sequence of SEQ ID NO: 4. In some embodiments, the variable heavy chain of an anti-TSPAN33 agent provided herein comprises a polypeptide that is at least 95% identical to the amino acid sequence of SEQ ID NO: 4. In some embodiments, the variable heavy chain of an anti-TSPAN33 agent provided herein comprises a polypeptide that is 100% identical to the amino acid sequence of SEQ ID NO: 4.

In some embodiments, the variable heavy chain of an anti-TSPAN33 agent provided herein comprises a polypeptide that is at least 75% identical to the amino acid sequence of SEQ ID NO: 12. In some embodiments, the variable heavy chain of an anti-TSPAN33 agent provided herein comprises a polypeptide that is at least 80% identical to the amino acid sequence of SEQ ID NO: 12. In some embodiments, the variable heavy chain of an anti-TSPAN33 agent provided herein comprises a polypeptide that is at least 85% identical to the amino acid sequence of SEQ ID NO: 12. In some embodiments, the variable heavy chain of an anti-TSPAN33 agent provided herein comprises a polypeptide that is at least 90% identical to the amino acid sequence of SEQ ID NO: 12. In some embodiments, the variable heavy chain of an anti-TSPAN33 agent provided herein comprises a polypeptide that is at least 95% identical to the amino acid sequence of SEQ ID NO: 12. In some embodiments, the variable heavy chain of an anti-TSPAN33 agent provided herein comprises a polypeptide that is 100% identical to the amino acid sequence of SEQ ID NO: 12.

In some embodiments, the variable heavy chain of an anti-TSPAN33 agent provided herein comprises a polypeptide that is at least 75% identical to the amino acid sequence of SEQ ID NO: 20. In some embodiments, the variable heavy chain of an anti-TSPAN33 agent provided herein comprises a polypeptide that is at least 80% identical to the amino acid sequence of SEQ ID NO: 20. In some embodiments, the variable heavy chain of an anti-TSPAN33 agent provided herein comprises a polypeptide that is at least 85% identical to the amino acid sequence of SEQ ID NO: 20. In some embodiments, the variable heavy chain of an anti-TSPAN33 agent provided herein comprises a polypeptide that is at least 90% identical to the amino acid sequence of SEQ ID NO: 20. In some embodiments, the variable heavy chain of an anti-TSPAN33 agent provided herein comprises a polypeptide that is at least 95% identical to the amino acid sequence of SEQ ID NO: 20. In some embodiments, the variable heavy chain of an anti-TSPAN33 agent provided herein comprises a polypeptide that is 100% identical to the amino acid sequence of SEQ ID NO: 20.

In some embodiments, the variable heavy chain of an anti-TSPAN33 agent provided herein comprises a polypeptide that is at least 75% identical to the amino acid sequence of SEQ ID NO: 28. In some embodiments, the variable heavy chain of an anti-TSPAN33 agent provided herein comprises a polypeptide that is at least 80% identical to the amino acid sequence of SEQ ID NO: 28. In some embodiments, the variable heavy chain of an anti-TSPAN33 agent provided herein comprises a polypeptide that is at least 85% identical to the amino acid sequence of SEQ ID NO: 28. In some embodiments, the variable heavy chain of an anti-TSPAN33 agent provided herein comprises a polypeptide that is at least 90% identical to the amino acid sequence of SEQ ID NO: 28. In some embodiments, the variable heavy chain of an anti-TSPAN33 agent provided herein comprises a polypeptide that is at least 95% identical to the amino acid sequence of SEQ ID NO: 28. In some embodiments, the variable heavy chain of an anti-TSPAN33 agent provided herein comprises a polypeptide that is 100% identical to the amino acid sequence of SEQ ID NO: 28.

In some embodiments, the variable heavy chain of an anti-TSPAN33 agent provided herein comprises a polypeptide that is at least 75% identical to the amino acid sequence of SEQ ID NO: 36. In some embodiments, the variable heavy chain of an anti-TSPAN33 agent provided herein comprises a polypeptide that is at least 80% identical to the amino acid sequence of SEQ ID NO: 36. In some embodiments, the variable heavy chain of an anti-TSPAN33 agent provided herein comprises a polypeptide that is at least 85% identical to the amino acid sequence of SEQ ID NO: 36. In some embodiments, the variable heavy chain of an anti-TSPAN33 agent provided herein comprises a polypeptide that is at least 90% identical to the amino acid sequence of SEQ ID NO: 36. In some embodiments, the variable heavy chain of an anti-TSPAN33 agent provided herein comprises a polypeptide that is at least 95% identical to the amino acid sequence of SEQ ID NO: 36. In some embodiments, the variable heavy chain of an anti-TSPAN33 agent provided herein comprises a polypeptide that is 100% identical to the amino acid sequence of SEQ ID NO: 36.

Variable Light Chain

In some embodiments, the variable light chain of an anti-TSPAN33 agent provided herein comprises a polypeptide that is at least 75% identical to the amino acid sequence of SEQ ID NO: 8. In some embodiments, the variable light chain of an anti-TSPAN33 agent provided herein comprises a polypeptide that is at least 80% identical to the amino acid sequence of SEQ ID NO: 8. In some embodiments, the variable light chain of an anti-TSPAN33 agent provided herein comprises a polypeptide that is at least 85% identical to the amino acid sequence of SEQ ID NO: 8. In some embodiments, the variable light chain of an anti-TSPAN33 agent provided herein comprises a polypeptide that is at least 90% identical to the amino acid sequence of SEQ ID NO: 8. In some embodiments, the variable light chain of an anti-TSPAN33 agent provided herein comprises a polypeptide that is at least 95% identical to the amino acid sequence of SEQ ID NO: 8. In some embodiments, the variable light chain of an anti-TSPAN33 agent provided herein comprises a polypeptide that is 100% identical to the amino acid sequence of SEQ ID NO: 8.

In some embodiments, the variable light chain of an anti-TSPAN33 agent provided herein comprises a polypeptide that is at least 75% identical to the amino acid sequence of SEQ ID NO: 16. In some embodiments, the variable light chain of an anti-TSPAN33 agent provided herein comprises a polypeptide that is at least 80% identical to the amino acid sequence of SEQ ID NO: 16. In some embodiments, the variable light chain of an anti-TSPAN33 agent provided herein comprises a polypeptide that is at least 85% identical to the amino acid sequence of SEQ ID NO: 16. In some embodiments, the variable light chain of an anti-TSPAN33 agent provided herein comprises a polypeptide that is at least 90% identical to the amino acid sequence of SEQ ID NO: 16. In some embodiments, the variable light chain of an anti-TSPAN33 agent provided herein comprises a polypeptide that is at least 95% identical to the amino acid sequence of SEQ ID NO: 16. In some embodiments, the variable light chain of an anti-TSPAN33 agent provided herein comprises a polypeptide that is 100% identical to the amino acid sequence of SEQ ID NO: 16.

In some embodiments, the variable light chain of an anti-TSPAN33 agent provided herein comprises a polypeptide that is at least 75% identical to the amino acid sequence of SEQ ID NO: 24. In some embodiments, the variable light chain of an anti-TSPAN33 agent provided herein comprises a polypeptide that is at least 80% identical to the amino acid sequence of SEQ ID NO: 24. In some embodiments, the variable light chain of an anti-TSPAN33 agent provided herein comprises a polypeptide that is at least 85% identical to the amino acid sequence of SEQ ID NO: 24. In some embodiments, the variable light chain of an anti-TSPAN33 agent provided herein comprises a polypeptide that is at least 90% identical to the amino acid sequence of SEQ ID NO: 24. In some embodiments, the variable light chain of an anti-TSPAN33 agent provided herein comprises a polypeptide that is at least 95% identical to the amino acid sequence of SEQ ID NO: 24. In some embodiments, the variable light chain of an anti-TSPAN33 agent provided herein comprises a polypeptide that is 100% identical to the amino acid sequence of SEQ ID NO: 24.

In some embodiments, the variable light chain of an anti-TSPAN33 agent provided herein comprises a polypeptide that is at least 75% identical to the amino acid sequence of SEQ ID NO: 32. In some embodiments, the variable light chain of an anti-TSPAN33 agent provided herein comprises a polypeptide that is at least 80% identical to the amino acid sequence of SEQ ID NO: 32. In some embodiments, the variable light chain of an anti-TSPAN33 agent provided herein comprises a polypeptide that is at least 85% identical to the amino acid sequence of SEQ ID NO: 32. In some embodiments, the variable light chain of an anti-TSPAN33 agent provided herein comprises a polypeptide that is at least 90% identical to the amino acid sequence of SEQ ID NO: 32. In some embodiments, the variable light chain of an anti-TSPAN33 agent provided herein comprises a polypeptide that is at least 95% identical to the amino acid sequence of SEQ ID NO: 32. In some embodiments, the variable light chain of an anti-TSPAN33 agent provided herein comprises a polypeptide that is 100% identical to the amino acid sequence of SEQ ID NO: 32.

In some embodiments, the variable light chain of an anti-TSPAN33 agent provided herein comprises a polypeptide that is at least 75% identical to the amino acid sequence of SEQ ID NO: 40. In some embodiments, the variable light chain of an anti-TSPAN33 agent provided herein comprises a polypeptide that is at least 80% identical to the amino acid sequence of SEQ ID NO: 40. In some embodiments, the variable light chain of an anti-TSPAN33 agent provided herein comprises a polypeptide that is at least 85% identical to the amino acid sequence of SEQ ID NO: 40. In some embodiments, the variable light chain of an anti-TSPAN33 agent provided herein comprises a polypeptide that is at least 90% identical to the amino acid sequence of SEQ ID NO: 40. In some embodiments, the variable light chain of an anti-TSPAN33 agent provided herein comprises a polypeptide that is at least 95% identical to the amino acid sequence of SEQ ID NO: 40. In some embodiments, the variable light chain of an anti-TSPAN33 agent provided herein comprises a polypeptide that is 100% identical to the amino acid sequence of SEQ ID NO: 40.

Agents that Competitively Bind with an Anti-TSPAN33 Agent

Provided herein are anti-TSPAN33 agents that competitively bind, or are capable of competitively binding, with one or more anti-TSPAN33 agents described herein. In particular, provided herein are anti-TSPAN33 agents that compete, or are capable of competing, with one or more anti-TSPAN33 agents described herein for binding to TSPAN33. Such agents that compete, or are capable of competing, with anti-TSPAN33 agents described herein may be referred to as competitor agents. In certain instances, an agent (i.e., competitor agent) may be considered to compete for binding to TSPAN33 when the competitor binds to the same general region of TSPAN33 as an anti-TSPAN33 agent described herein (e.g., an extracellular domain). In certain instances, an agent (i.e., competitor agent) may be considered to compete for binding to TSPAN33 when the competitor binds to the exact same region of TSPAN33 as an anti-TSPAN33 agent described herein (e.g., exact same peptide (linear epitope) or exact same surface amino acids (conformational epitope)). In certain instances, an agent (i.e., competitor agent) may be considered capable of competing for binding to TSPAN33 when the competitor binds to the same general region of TSPAN33 as an anti-TSPAN33 agent described herein (e.g., an extracellular domain) under suitable assay conditions. In certain instances, an agent (i.e., competitor agent) may be considered capable of competing for binding to TSPAN33 when the competitor binds to the exact same region of TSPAN33 as an anti-TSPAN33 agent described herein (e.g., exact same peptide (linear epitope) or exact same surface amino acids (conformational epitope)) under suitable assay conditions.

In certain instances, an agent (i.e., competitor agent) may be considered to compete for binding to TSPAN33 when the competitor blocks the binding of one or more anti-TSPAN33 agents described herein to TSPAN33. In certain instances, an agent (i.e., competitor agent) may be considered capable of competing for binding to TSPAN33 when the competitor blocks the binding of one or more anti-TSPAN33 agents described herein to TSPAN33 under suitable assay conditions. Whether a competitor blocks the binding of one or more anti-TSPAN33 agents described herein to TSPAN33 may be determined using a suitable competition assay or blocking assay, such as, for example, a blocking assay as described in Example 5 herein. A competitor agent may block binding of one or more anti-TSPAN33 agents described herein to TSPAN33 in a competition or blocking assay by 50% or more, and conversely, one or more anti-TSPAN33 agents described herein may block binding of the competitor agent to TSPAN33 in a competition or blocking assay by about 50% or more. For example, an agent (i.e., competitor agent) may block binding of one or more anti-TSPAN33 agents described herein to TSPAN33 in a competition or blocking assay by about 55%, 60%, 65%, 70%, 75%, 80%, 85%, 90%, 95%, or 100%, and conversely, one or more anti-TSPAN33 agents described herein may block binding of the competitor agent to TSPAN33 in a competition or blocking assay by about 55%, 60%, 65%, 70%, 75%, 80%, 85%, 90%, 95%, or 100%.

In certain instances, an agent (i.e., competitor agent) may be considered to compete for binding to TSPAN33 when the competitor blocks the binding of one or more anti-TSPAN33 agents described herein to TSPAN33 expressed on a particular cell type (e.g., TSPAN33-positive cell, B cell, activated B cell). In certain instances, an agent (i.e., competitor agent) may be considered capable of competing for binding to TSPAN33 when the competitor blocks the binding of one or more anti-TSPAN33 agents described herein to TSPAN33 expressed on a particular cell type (e.g., TSPAN33-positive cell, B cell, activated B cell) under suitable assay conditions. For example, a competitor agent may block binding of one or more anti-TSPAN33 agents described herein to TSPAN33 on activated B cells in a competition or blocking assay by 50% or more, and conversely, one or more anti-TSPAN33 agents described herein may block binding of the competitor agent to TSPAN33 on activated B cells in a competition or blocking assay by about 50% or more. For example, an agent (i.e., competitor agent) may block binding of one or more anti-TSPAN33 agents described herein to TSPAN33 on activated B cells in a competition or blocking assay by about 55%, 60%, 65%, 70%, 75%, 80%, 85%, 90%, 95%, or 100%, and conversely, one or more anti-TSPAN33 agents described herein may block binding of the competitor agent to TSPAN33 in a competition or blocking assay by about 55%, 60%, 65%, 70%, 75%, 80%, 85%, 90%, 95%, or 100%. In some embodiments, an agent (i.e., competitor agent) blocks binding of one or more anti-TSPAN33 agents described herein to TSPAN33 on activated B cells in a competition or blocking assay by about 60% to about 90%, and conversely, in some embodiments, one or more anti-TSPAN33 agents described herein blocks binding of the competitor agent to TSPAN33 in a competition or blocking assay by about 60% to about 90%. For example, an agent (i.e., competitor agent) may block binding of one or more anti-TSPAN33 agents described herein to TSPAN33 on activated B cells in a competition or blocking assay by about 60%, 65%, 70%, 75%, 80%, 85%, or 90%, and conversely, one or more anti-TSPAN33 agents described herein may block binding of the competitor agent to TSPAN33 in a competition or blocking assay by about 60%, 65%, 70%, 75%, 80%, 85%, or 90%.

In certain instances, an agent (i.e., competitor agent) may be considered to compete for binding to TSPAN33 when the competitor binds to TSPAN33 with a similar affinity as one or more anti-TSPAN33 agents described herein. In certain instances, an agent (i.e., competitor agent) may be considered capable of competing for binding to TSPAN33 when the competitor binds to TSPAN33 with a similar affinity as one or more anti-TSPAN33 agents described herein under suitable assay conditions. In some embodiments, an agent (i.e., competitor agent) is considered to compete for binding to TSPAN33 when the competitor binds to TSPAN33 with an affinity that is at least about 50% of the affinity of one or more anti-TSPAN33 agents described herein. For example, an agent (i.e., competitor agent) may be considered to compete for binding to TSPAN33 when the competitor binds to TSPAN33 with an affinity that is at least about 55%, 60%, 65%, 70%, 75%, 80%, 85%, 90%, 95%, or 100% of the affinity of one or more anti-TSPAN33 agents described herein. A competitor agent may comprise any feature described herein for anti-TSPAN33 agents.

Also provided herein are anti-TSPAN33 agents that bind to, or are capable of binding to, the same epitope as one or more anti-TSPAN33 agents described herein. In particular, provided herein are anti-TSPAN33 agents that compete with one or more anti-TSPAN33 agents described herein for binding to the same epitope on TSPAN33. Such agents that bind the same epitope may be referred to as epitope competitors. In certain instances, an epitope competitor may bind to the exact same region of TSPAN33 as an anti-TSPAN33 agent described herein (e.g., exact same peptide (linear epitope) or exact same surface amino acids (conformational epitope)). In certain instances, epitope competitor blocks the binding of one or more anti-TSPAN33 agents described herein to TSPAN33. An epitope competitor may block binding of one or more anti-TSPAN33 agents described herein to TSPAN33 in a competition assay by about 50% or more, and conversely, one or more anti-TSPAN33 agents described herein may block binding of the epitope competitor to TSPAN33 in a competition assay by 50% or more. In certain instances, an epitope competitor binds to TSPAN33 with a similar affinity as one or more anti-TSPAN33 agents described herein. In some embodiments, an epitope competitor binds to TSPAN33 with an affinity that is at least about 50% of the affinity of one or more anti-TSPAN33 agents described herein. For example, an epitope competitor may bind to TSPAN33 with an affinity that is at least about 55%, 60%, 65%, 70%, 75%, 80%, 85%, 90%, 95%, or 100% of the affinity of one or more anti-TSPAN33 agents described herein. An epitope competitor may comprise any feature described herein for anti-TSPAN33 agents.

Antibody Preparation

In some embodiments, an anti-TSPAN33 agent is an antibody. Methods for generating anti-TSPAN33 antibodies and variants of anti-TSPAN33 antibodies are described in the Examples below. In some embodiments, an anti-TSPAN33 agent is a humanized antibody, or a derivative thereof that binds TSPAN33. Humanized anti-TSPAN33 antibodies may be prepared, based on a nonhuman anti-TSPAN33 antibody. Fully human antibodies may also be prepared, e.g., in a genetically engineered (i.e., transgenic) mouse (e.g. from Medarex) that, when presented with an immunogen, can produce a human antibody that does not necessarily require CDR grafting. These antibodies are fully human (100% human protein sequences) from animals such as mice in which the non-human antibody genes are suppressed and replaced with human antibody gene expression. Antibodies may be generated against TSPAN33 when presented to these genetically engineered mice or other animals that might be able to produce human frameworks for the relevant CDRs.

Where a variant is generated, the parent antibody is prepared. Example techniques for generating such nonhuman antibody and parent antibodies will be described in the following sections.

Antigen Preparation

The antigen used for production of antibodies may be, e.g., intact TSPAN33, particularly expressed in cells, or a portion of TSPAN33 (e.g. a TSPAN33 fragment comprising the epitope). Other forms of antigens useful for generating antibodies will be apparent to those skilled in the art.

Polyclonal Antibodies

Polyclonal antibodies are preferably raised in animals (vertebrate or invertebrates, including mammals, birds and fish, including cartilaginous fish) by multiple subcutaneous (sc) or intraperitoneal (ip) injections of the relevant antigen and an adjuvant. It may be useful to conjugate the relevant antigen to a protein or other carrier that is immunogenic in the immunized species, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Non-protein carriers (e.g., colloidal gold) are also known in the art for antibody production.

Animals are immunized against the antigen, immunogenic conjugates, or derivatives by combining, e.g., 100 μg or 5 μg of the protein or conjugate (for rabbits or mice, respectively) with three volumes of Freund's complete adjuvant and injecting the solution intradermally at multiple sites. One month later the animals are boosted with one-fifth to one-tenth of the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by other methods such as recombinant DNA methods (U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation, by an in vitro binding assay, such as radioimmunoassay (RIA) or enzyme-linked immunoabsorbant assay (ELISA), or by flow cytometric analysis of cells expressing the membrane antigen.

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). Alternatively, cDNA may be prepared from mRNA and the cDNA then subjected to DNA sequencing. The hybridoma cells serve as a preferred source of such genomic DNA or RNA for cDNA preparation. Once isolated, the DNA may be placed into expression vectors, which are well known in the art, and which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

Humanization and Amino Acid Sequence Variants

General methods for humanization of antibodies are described in update U.S. Pat. No. 5,861,155, US19960652558 19960606, U.S. Pat. No. 6,479,284, US20000660169 20000912, U.S. Pat. No. 6,407,213, US19930146206 19931117, U.S. Pat. No. 6,639,055, US20000705686 20001102, U.S. Pat. No. 6,500,931, US19950435516 19950504, U.S. Pat. Nos. 5,530,101, 5,585,089, US19950477728 19950607, U.S. Pat. No. 5,693,761, US19950474040 19950607, U.S. Pat. No. 5,693,762, US19950487200 19950607, U.S. Pat. No. 6,180,370, US19950484537 19950607, US2003229208, US20030389155 20030313, U.S. Pat. No. 5,714,350, US19950372262 19950113, U.S. Pat. No. 6,350,861, US19970862871 19970523, U.S. Pat. No. 5,777,085, US19950458516 19950517, U.S. Pat. No. 5,834,597, US19960656586 19960531, U.S. Pat. No. 5,882,644, US19960621751 19960322, U.S. Pat. No. 5,932,448, US19910801798 19911129, U.S. Pat. No. 6,013,256, US19970934841 19970922, U.S. Pat. No. 6,129,914, US19950397411 19950301, U.S. Pat. Nos. 6,210,671, 6,329,511, US19990450520 19991129, US2003166871, US20020078757 20020219, U.S. Pat. No. 5,225,539, US19910782717 19911025, U.S. Pat. No. 6,548,640, US19950452462 19950526, U.S. Pat. No. 5,624,821, and US19950479752 19950607. In certain embodiments, it may be desirable to generate amino acid sequence variants of these humanized antibodies, particularly where these improve the binding affinity or other biological properties of the antibody.

Amino acid sequence variants of the anti-TSPAN33 antibody are prepared by introducing appropriate nucleotide changes into the anti-TSPAN33 antibody DNA, or by peptide synthesis. Such variants include, for example, deletions from, and/or insertions into and/or substitutions of, residues within the amino acid sequences of the anti-TSPAN33 antibodies of the examples herein. Any combination of deletion, insertion, and substitution is made to arrive at the final construct, provided that the final construct possesses the desired characteristics. The amino acid changes also may alter post-translational processes of the humanized or variant anti-TSPAN33 antibody, such as changing the number or position of glycosylation sites.

A useful method for identification of certain residues or regions of the anti-TSPAN33 antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with TSPAN33 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-TSPAN33 antibody variants are screened for the desired activity. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or the antibody fused to an epitope tag. Other insertional variants include the fusion of an enzyme or a polypeptide which increases the serum half-life of the antibody to the N- or C-terminus of the antibody.

Another type of variant is an amino acid substitution variant. These variants have at least one amino acid residue removed from the antibody molecule and a different residue inserted in its place. The sites of greatest interest for substitutional mutagenesis include the hypervariable regions, but FR alterations are also contemplated. Conservative substitutions are preferred, but more substantial changes may be introduced and the products may be screened. Examples of substitutions are listed below:

Example Amino Acid Residue Substitutions

Ala (A) val; leu; ile val
Arg (R) lys; gln; asn lys
Asn (N) gln; his; asp, lys; gln arg
Asp (D) glu; asn glu
Cys (C) ser; ala ser
Gln (Q) asn; glu asn
Glu (E) asp; gln asp
Gly (G) ala ala
His (H) asn; gln; lys; arg arg
Ile (I) leu; val; met; ala; leu phe; norleucine
Leu (L) norleucine; ile; val; ile met; ala; phe
Lys (K) arg; gln; asn arg
Met (M) leu; phe; ile leu
Phe (F) leu; val; ile; ala; tyr tyr
Pro (P) ala ala
Ser (S) thr thr
Thr (T) ser ser
Trp (W) tyr; phe tyr
Tyr (Y) trp; phe; thr; ser phe
Val (V) ile; leu; met; phe; leu ala; norleucine Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked and/or or O-linked. N-linked refers to the attachment of the carbohydrate moiety to the side chain of an asparagine residue. The tripeptide sequences asparagine-X-serine and asparagine-X-threonine, where X is any amino acid except proline, are the most common recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-TSPAN33 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TSPAN33 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807. Human antibodies can also be derived from phage-display libraries (Hoogenboom et al., J. Mol. Biol., 227:381 (1991); Marks et al., J. Mol. Biol., 222:581-597 (1991); and U.S. Pat. Nos. 5,565,332 and 5,573,905). Human antibodies may also be generated by in vitro activated B cells (see U.S. Pat. Nos. 5,567,610 and 5,229,275).

Antigen-Binding Antibody Fragments

In certain embodiments, the anti-TSPAN33 agent is an antibody fragment which retains at least one desired activity, including antigen binding. Various techniques have been developed for the production of antibody fragments. Traditionally, these fragments were derived via proteolytic digestion of intact antibodies (see, e.g., Morimoto et al., Journal of Biochemical and Biophysical Methods 24:107-117(1992) and Brennan et al., Science 229:81 (1985)). However, these fragments can now be produced directly by recombinant host cells. For example, Fab'-SH fragments can be directly recovered from *E. coli* and chemically coupled to form F(ab')$_2$ fragments (Carter et al., Bio/Technology 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

Multispecific Antibodies and Other Agents

In some embodiments, the anti-TSPAN33 agent will comprise a first binding moiety and a second binding moiety, where the first binding moiety is specifically reactive with a first molecule that is TSPAN33 and the second binding moiety is specifically reactive with a second molecule that is a molecular species different from the first molecule. Such agents may comprise a plurality of first binding moieties, a plurality of second binding moieties, or a plurality of first binding moieties and a plurality of second binding moieties. Preferably, the ratio of first binding moieties to second binding moieties is about 1:1, although it may range from about 1000:1 to about 1:1000, where the ratio is preferably measured in terms of valency.

In those embodiments where the first moiety is an antibody, the binding moiety may also be an antibody. In preferred embodiments, the first and second moieties are linked via a linker moiety, which may have two to many 100's or even thousands of valencies for attachment of first and second binding moieties by one or different chemistries. Examples of bispecific antibodies include those which are reactive against two different epitopes; in some embodiment one epitope is a TSPAN33 epitope and the second epitope is on an unrelated soluble molecule. In other embodiments the bispecific antibody is reactive against an epitope on TSPAN33 and against an epitope on a different molecule found on the surface of the same cell. In other embodiments the bispecific antibody is reactive against an epitope on TSPAN33 and against an epitope on a different molecule found on the surface of a different cell.

The compositions of the invention may also comprise a first agent and a second agent, where the first agent comprises a first binding moiety specifically reactive with a first molecule selected from the group consisting of TSPAN33 and the second agent comprises a second binding moiety specifically reactive with a second molecule that is a molecular species different than the first molecule. The first and/or second agent may be an antibody. The ratio of first agent to second agent may range from about 1,000:1 to 1:1,000, although the preferred ratio is about 1:1. In some embodiments, it may be desirable to generate multispecific (e.g. bispecific) anti-TSPAN33 antibodies having binding specificities for at least two different epitopes. Example bispecific antibodies may bind to two different epitopes of TSPAN33. Bispecific antibodies can be prepared as full length antibodies or antibody fragments (e.g., F(ab')$_2$ bispecific antibodies).

According to another approach for making bispecific antibodies, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure where intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. In yet a further embodiment, Fab'-SH fragments directly recovered from E. coli can be chemically coupled in vitro to form bispecific antibodies. Shalaby et al., J. Exp. Med. 175:217-225 (1992).

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol. 152:5368 (1994). Alternatively, the bispecific antibody may be a "linear antibody" produced as described in Zapata et al. Protein Eng. 8(10):1057-1062 (1995).

Antibodies with more than two valencies are contemplated. For example, trispecific antibodies can be prepared. Tutt et al., J. Immunol. 147:60 (1991).

The antibody (or polymer or polypeptide) of the invention comprising one or more binding sites per arm or fragment thereof will be referred to herein as "multivalent" antibody. For example a "bivalent" antibody of the invention comprises two binding sites per Fab or fragment thereof whereas a "trivalent" polypeptide of the invention comprises three binding sites per Fab or fragment thereof. In a multivalent polymer of the invention, the two or more binding sites per Fab may be binding to the same or different antigens. For example, the two or more binding sites in a multivalent polypeptide of the invention may be directed against the same antigen, for example against the same parts or epitopes of said antigen or against two or more same or different parts or epitopes of said antigen; and/or may be directed against different antigens; or a combination thereof. Thus, a bivalent polypeptide of the invention for example may comprise two identical binding sites, may comprise a first binding sites directed against a first part or epitope of an antigen and a second binding site directed against the same part or epitope of said antigen or against another part or epitope of said antigen; or may comprise a first binding sites directed against a first part or epitope of an antigen and a second binding site directed against the a different antigen. However, as will be clear from the description hereinabove, the invention is not limited thereto, in the sense that a multivalent polypeptide of the invention may comprise any number of binding sites directed against the same or different antigens. In one embodiment the multivalent polypeptide comprises at least two ligand binding elements, one of which contains one or more CDR peptide sequences shown herein. In another embodiment the multivalent polypeptide comprises three ligand binding sites, each independently selected from the CDR sequences disclosed herein.

At least one of the ligand binding elements binds TSPAN33. In one embodiment at least one of the ligand binding elements binds another target. In one embodiment there are up to 10,000 binding elements in a multivalent binding molecule, and the ligand binding elements may be linked to a scaffold.

The antibody (or polymer or polypeptide) of the invention that contains at least two binding sites per Fab or fragment thereof, in which at least one binding site is directed against a first antigen and a second binding site directed against a second antigen different from the first antigen, will also be referred to as "multispecific". Thus, a "bispecific" polymer comprises at least one site directed against a first antigen and at least one a second site directed against a second antigen, whereas a "trispecific" is a polymer that comprises at least one binding site directed against a first antigen, at least one further binding site directed against a second antigen, and at least one further binding site directed against a third antigen; etc. Accordingly, in their simplest form, a bispecific polypeptide of the invention is a bivalent polypeptide (per Fab) of the invention. However, as will be clear from the description hereinabove, the invention is not limited thereto, in the sense that a multispecific polypeptide of the invention may comprise any number of binding sites directed against two or more different antigens.

Other Modifications

Other modifications of the anti-TSPAN33 antibody are contemplated. For example, the invention also pertains to immunoconjugates comprising the antibody described herein conjugated to a cytotoxic agent such as a toxin (e.g., an enzymatically active toxin of bacterial, fungal, plant or animal origin, or fragments thereof), or a radioactive isotope (for example, a radioconjugate), or a cytotoxic drug. Such conjugates are sometimes referred to as "agent-drug conjugates" or "ADC". Conjugates are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The anti-TSPAN33 antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. For example, liposomes can be generated by the reverse phase evaporation method with a lipid composition comprising phosphatidyl choline, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286-288 (1982) via a disulfide interchange reaction. Another active ingredient is optionally contained within the liposome.

Enzymes or other polypeptides can be covalently bound to the anti-TSPAN33 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature 312:604-608 (1984)).

In certain embodiments of the invention, it may be desirable to use an antibody fragment, rather than an intact antibody, to increase penetration of target tissues and cells, for example. In this case, it may be desirable to modify the antibody fragment in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

Covalent modifications of the anti-TSPAN33 antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Example covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Nucleic Acids, Vectors, Host Cells and Recombinant Methods

The invention also provides isolated nucleic acid encoding the anti-TSPAN33 antibody, vectors and host cells comprising the nucleic acid, and recombinant techniques for the production of the antibody.

Provided herein are nucleic acids (e.g., isolated nucleic acids) comprising a nucleotide sequence that encodes an anti-TSPAN33 agent or antibody, or fragment thereof. In some embodiments, a nucleic acid encodes an immunoglobulin heavy chain variable domain of an anti-TSPAN33 agent provided herein. In some embodiments, a nucleic acid encodes an immunoglobulin light chain variable domain of an anti-TSPAN33 agent provided herein. In some embodiments, a nucleic acid encodes an immunoglobulin heavy chain variable domain and an immunoglobulin light chain variable domain of an anti-TSPAN33 agent provided herein. In some embodiments, a nucleic acid comprises a nucleotide sequence that encodes an amino acid sequence of any one of SEQ ID NOs. 1-46. For example, a nucleic acid may comprise a nucleotide sequence that encodes a CDR amino acid sequence of any one of SEQ ID NOs. 1-3, 5-7, 9-11, 13-15, 17-19, 21-23, 25-27, 29-31, 33-35, 37-39, and 41-46. A nucleic acid may comprise a nucleotide sequence that encodes an immunoglobulin heavy chain variable domain amino acid sequence of any one of SEQ ID NOs. 4, 12, 20, 28, and 36. A nucleic acid may comprise a nucleotide sequence that encodes an immunoglobulin light chain variable domain amino acid sequence of any one of SEQ ID NOs. 8, 16, 24, 32, and 40.

For recombinant production of the antibody, the nucleic acid encoding it may be isolated and inserted into a replicable vector for further cloning (amplification of the DNA) or for expression. In another embodiment, the antibody may be produced by homologous recombination, e.g. as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-TSPAN33 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated anti-TSPAN33 antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* (silk moth) have been identified. A variety of viral strains for transfection are publicly available, e.g., the L-1 variant of *Autographa*

*californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification, such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations, Dosing, and Routes of Administration

The present invention provides anti-TSPAN33 antibodies and related compositions and methods cause elimination of TSPAN33 expressing cells from the body, and to identify and quantify the number of TSPAN33 expressing cells in tissue samples.

The therapeutic methods and compositions of the invention are considered "TSPAN33-based" in order to indicate that these therapies can change the relative or absolute numbers of undesirable or toxic TSPAN33 expressing cells such as lymphomas or autoimmune B lymphocytes.

One way to control the amount of undesirable TSPAN33 expressing cells in a patient is by providing a composition that comprises one or more anti-TSPAN33 antibodies to cause cytotoxic activity towards the TSPAN33-expressing cells.

Anti-TSPAN33 antibodies may be formulated in a pharmaceutical composition that is useful for a variety of purposes, including the treatment of diseases, disorders or physical trauma. Pharmaceutical compositions comprising one or more anti-TSPAN33 antibodies of the invention may be incorporated into kits and medical devices for such treatment. Medical devices may be used to administer the pharmaceutical compositions of the invention to a patient in need thereof, and according to one embodiment of the invention, kits are provided that include such devices. Such devices and kits may be designed for routine administration, including self-administration, of the pharmaceutical compositions of the invention.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations for in vivo administration must be sterile. This is readily accomplished for instance by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered as intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For therapeutic applications, the anti-TSPAN33 agents, e.g., antibodies, of the invention are administered to a mammal, preferably a human, in a pharmaceutically acceptable dosage form such as those discussed above, including those that may be administered to a human intravenously as a bolus or by continuous infusion over a period of time, or by intramuscular, intraperitoneal, intra-cerebrospinal, subcutaneous, intra-articular, intrasynovial, intrathecal, oral, topical, or inhalation routes.

For the prevention or treatment of disease, the appropriate dosage of antibody will depend on the type of disease treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 □g/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging. Detection methods using the antibody to determine TSPAN33 levels in bodily fluids or tissues may be used in order to optimize patient exposure to the therapeutic antibody.

According to another embodiment of the invention, the composition comprising an agent, e.g., a mAb, that interferes with TSPAN33 activity is administered as a monotherapy, while in other preferred embodiments, the composition comprising the agent that interferes with TSPAN33 activity is administered as part of a combination therapy. In some cases the effectiveness of the antibody in preventing or treating disease may be improved by administering the antibody serially or in combination with another agent that is effective for those purposes, such as a chemotherapeutic drug for treatment of cancer. In other cases, the anti-TSPAN33 agent may serve to enhance or sensitize cells to chemotherapeutic treatment, thus permitting efficacy at lower doses and with lower toxicity. Preferred combination therapies include, in addition to administration of the composition comprising an agent that reduces the number of TSPAN33 expressing cells, delivering a second therapeutic regimen selected from the group consisting of administration of a chemotherapeutic agent, radiation therapy, surgery, and a combination of any of the foregoing.

Such other agents may be present in the composition being administered or may be administered separately. Also, the antibody is suitably administered serially or in combination with the other agent or modality, e.g., chemotherapeutic drug or radiation for treatment of cancer or an immunosuppressive drug.

Research and Diagnostic, Including Clinical Diagnostic, Uses for the Anti-TSPAN33 Agents of the Invention The anti-TSPAN33 agents, e.g., antibodies, of the invention may be used to detect and/or purify TSPAN33, e.g., from bodily fluid(s) or expressed on cells in bodily fluids or tissues. In certain instances, an anti-TSPAN33 agent provided herein may be used as a biomarker of B cell activation for the diagnosis of allergies, autoimmune diseases, and/or lymphomas where TSPAN33 is present.

Provided herein are diagnostic reagents comprising an anti-TSPAN33 agent described herein. For example, anti-TSPAN33 agents, e.g., antibodies, provided herein may be used to detect and/or purify TSPAN33, e.g., from bodily fluid(s) or expressed on cells in bodily fluids or tissues. Also provided herein are methods for detecting TSPAN33. For example, a method may comprise contacting a sample (e.g., a biological sample known or suspected of to contain TSPAN33) with an anti-TSPAN33 agent provided herein, and, if the sample contains TSPAN33, detecting TSPAN33:anti-TSPAN33 complexes. Also provided herein are reagents comprising an anti-TSPAN33 agent described herein and methods for detecting TSPAN33 for research purposes.

Anti-TSPAN33 antibodies may be useful in diagnostic assays for TSPAN33, e.g., detecting its presence in specific cells, tissues, or bodily fluids. Such diagnostic methods may be useful in diagnosis, e.g., of a hyperproliferative disease or disorder. Thus clinical diagnostic uses as well as research uses are comprehended by the invention.

In some embodiments, an anti-TSPAN33 agent/antibody comprises a detectable marker or label. In some embodiments, an anti-TSPAN33 agent/antibody is conjugated to a detectable marker or label. For research and diagnostic applications, the antibody may be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin, Texas Red and Brilliant Violet™ are available. The fluorescent labels can be conjugated to the antibody using the techniques disclosed in Current Protocols in Immunology, supra, for example. Fluorescence can be quantified using a flow cytometer, imaging microscope or fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:
  (i) Horseradish peroxidase (HRPO) with hydrogen peroxidase as a substrate, where the hydrogen peroxidase oxidizes a dye precursor (e.g., orthophenylene diamine (OPD) or 3,3',5,5'-tetramethyl benzidine hydrochloride (TMB));
  (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-TSPAN33 antibody need not be labeled, and the presence thereof can be detected, e.g., using a labeled antibody which binds to the anti-TSPAN33 antibody.

In some embodiments, an anti-TSPAN33 agent/antibody herein is immobilized on a solid support or substrate. In some embodiments, an anti-TSPAN33 agent/antibody herein is non-diffusively immobilized on a solid support (e.g., the anti-TSPAN33 agent/antibody does not detach from the solid support). A solid support or substrate can be any physically separable solid to which an anti-TSPAN33 agent/antibody can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, a solid support or substrate can be a collection of particles. In some embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of Fe2+ and Fe3+). An anti-TSPAN33 agent/antibody may be linked to a solid support by covalent bonds or by non-covalent interactions and may be linked to a solid support directly or indirectly (e.g., via an intermediary agent such as a spacer molecule or biotin).

The antibodies of the present invention may be employed in any known assay method, such as flow cytometry, immunohistochemistry, immunofluorescence, mass cytometry (e.g., Cytof instrument), competitive binding assays, direct and indirect sandwich assays, and immunoprecipitation assays. Zola, Monoclonal Antibodies: A Manual of Techniques, pp. 147-158 (CRC Press, Inc. 1987).

Flow cytometry and mass cytometry assays involve the use of a single primary antibody to specifically identify the presence of the target molecule expressed on the surface of a dispersed suspension of individual cells. The dispersed cells are typically obtained from a biological fluid sample, e.g., blood, but may also be obtained from a dispersion of single cells prepared from a solid tissue sample such as spleen or tumor biopsy. The primary antibody may be directly conjugated with a detectable moiety, e.g., a fluorophore such as phycoerythrin for flow cytometry or a heavy metal chelate for mass cytometry. Alternatively, the primary antibody may be unlabeled or labeled with an undetectable tag such as biotin, and the primary antibody is then detected by a detectably labeled secondary antibody that specifically recognizes the primary antibody itself or the tag on the primary antibody. The labeled cells are then analyzed in an instrument capable of single cell detection, e.g., flow cytometer, mass cytometer, fluorescence microscope or bright field light microscope, to identify those individual cells in the dispersed population or tissue sample that express the target recognized by the primary antibody. Detailed description of the technological basis and practical application of flow cytometry principles may be found in, e.g., Shapiro, Practical Flow Cytometry, 4$^{th}$ Edition, Wiley, 2003.

Sandwich assays involve the use of two antibodies, each capable of binding to a different immunogenic portion, or epitope, of the protein detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. In a cell ELISA, the target cell population may be attached to the solid support using antibodies first attached to the support and that recognize different cell surface proteins. These first antibodies capture the cells to the support. TSPAN33 on the surface of the cells can then be detected by adding anti-TSPAN33 antibody to the captured cells and detecting the amount of TSPAN33 antibody attached to the cells.

For immunohistochemistry, the blood or tissue sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P, or $^{35}$S) so that the bound target molecule can be localized using immunoscintillography.

Detection of TSPAN33 on Cells

Provided herein are agents and methods for detecting TSPAN33 on cells. In some embodiment, provided herein are agents and methods for detecting TSPAN33 on immune cells. Detection of TSPAN33 on immune cells may refer to detection on the surface of immune cells (e.g., by surface staining) and/or inside immune cells (e.g., by intracellular staining). In some embodiments, agents and methods are provided for detecting TSPAN33 in a heterogeneous population of immune cells. A heterogeneous population of immune cells may comprise two or more types of immune cells. For example a heterogeneous population of immune cells may comprise two or more of B cells, plasmacytoid dendritic cells (pDCs), lymphocytes, leukocytes, T cells, monocytes, macrophages, neutrophils, myeloid dendritic cells (mDCs), innate lymphoid cells, mast cells, eosinophils, basophils, natural killer cells, and the like. In some embodiments, a heterogeneous population of immune cells comprises peripheral blood mononuclear cells (PBMCs) which may include, for example, T cells, B cells, natural killer cells, and monocytes.

Provided herein, in some embodiments, are agents and methods for detecting TSPAN33 on B cells. Detection of TSPAN33 on B cells may refer to detection on the surface of B cells (e.g., by surface staining) and/or inside B cells (e.g., by intracellular staining). Provided herein, in some embodiments, are agents and methods for detecting TSPAN33 on activated B cells. Detection of TSPAN33 on activated B cells may refer to detection on the surface of activated B cells (e.g., by surface staining) and/or inside activated B cells (e.g., by intracellular staining). B cells may be activated in vitro (e.g., by exposing B cells in culture to certain stimulatory factors (e.g., CD40 ligand (also referred to as CD40L, CD154, TNFSF5, CD40LG, HIGM1, IGM, IMD3, T-BAM, TRAP, and gp39) and IL-4). In certain instances, B cells are activated in vivo. For example, B cells may be activated in vivo as part of an allergic reaction and/or immune response to an infectious agent; and may be activated in certain diseases or disorders (e.g., leukemia, lymphomas (e.g., Hodgkin's disease, non-Hodgkin's lymphoma, diffuse large B cell lymphoma, Burkitt's lymphoma), and autoimmune diseases (rheumatoid arthritis)).

Provided herein, in some embodiments, are agents and methods for detecting TSPAN33 on monocytes. Provided herein, in some embodiments, are agents and methods for detecting TSPAN33 on monocytes in the presence of activated B cells, and/or in a population of PBMCs activated with stimulatory factors (e.g., CD40L and/or IL-4). Detection of TSPAN33 on monocytes may refer to detection on the surface of monocytes (e.g., by surface staining) and/or inside monocytes (e.g., by intracellular staining).

Generally, cells (e.g., PBMCs, B cells, activated B cells, monocytes) are contacted with an anti-TSPAN33 agent described herein (e.g., in a flow cytometry assay as described in Example 5; or any suitable protein or cell detection assay). In some embodiments, TSPAN33 is detected at a significant level in certain immune cells by an anti-TSPAN33 agent described herein. TSPAN33 may be detected at a significant level by an anti-TSPAN33 agent described herein in certain immune cells and not significantly detected in other immune cells. For example, TSPAN33 may be detected at a significant level by an anti-TSPAN33 agent described herein in activated B cells and not significantly detected in resting B cells. In another example, TSPAN33 may be detected at a significant level by an anti-TSPAN33 agent described herein in activated B cells and not significantly detected in T cells. The level of TSPAN33 detection in certain immune cells may vary according to certain factors such as, for example, type of detection assay, type of detection reagent (e.g., type of dye), antibody concentration, donor cell variability, and the like.

Detection of TSPAN33 at a significant level may refer to a particular signal to noise (S:N) ratio (e.g., threshold or range) measured in a flow cytometry assay. In some embodiments, detection of TSPAN33 at a significant level refers to a signal to noise (S:N) ratio of about 2.0 or greater. For example, detection of TSPAN33 at a significant level may refer to a signal to noise (S:N) ratio of about 2 or greater, about 2.5 or greater, about 3 or greater, about 4 or greater, about 5 or greater, about 6 or greater, about 7 or greater, about 8 or greater, about 9 or greater, about 10 or greater, about 11 or greater, about 12 or greater, about 13 or greater, about 14 or greater, about 15 or greater, about 16 or greater, about 17 or greater, about 18 or greater, about 19 or greater, about 20 or greater, about 25 or greater, about 30 or greater, about 35 or greater, about 40 or greater, about 45 or greater, about 50 or greater, about 55 or greater, or about 60 or greater. No significant detection of TSPAN33 may refer to a particular signal to noise (S:N) ratio (e.g., threshold or range) measured in a flow cytometry assay. In some embodiments, no significant detection of TSPAN33 refers to a signal to noise (S:N) ratio of about 1.5 or less. In some embodiments, no significant detection of TSPAN33 refers to a signal to noise (S:N) ratio of about 1 or less.

Provided herein are methods of diagnosing a disease or disorder associated with aberrant levels of TSPAN33. Aberrant levels of TSPAN33 may refer to increased levels of TSPAN33 relative to levels of a control protein, relative to levels of TSPAN33 in a control subject (e.g., a healthy subject), relative to levels of TSPAN33 in the same subject prior to the onset of the disease or disorder, or relative to the expression of TSPAN33 in a control cell. An increased level of TSPAN33 may refer to about a 10% increase, 25% increase, 50% increase, 100% increase, 200% increase, 500% increase, or more. Disease or disorders associated with aberrant levels of TSPAN33 may include leukemia, lymphoma, and autoimmune disease, examples of which are provided below.

Diagnostic Kits Incorporating the Anti-TSPAN33 Agents of the Invention

As a matter of convenience, the antibody of the present invention can be provided in a kit, for example, a packaged combination of reagents in predetermined amounts with instructions for performing the diagnostic assay. Where the antibody is labelled with a fluorophore, the kit will include an identical isotype negative control irrelevant antibody to control for non-specific binding of the anti-TSPAN33 antibody. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic Uses for Anti-TSPAN33 Agents

Provided herein are methods of treating or preventing a disease or disorder associated with aberrant levels of TSPAN33. Aberrant levels of TSPAN33 may refer to increased levels of TSPAN33 relative to levels of a control protein, relative to levels of TSPAN33 in a control subject (e.g., a healthy subject), relative to levels of TSPAN33 in the same subject prior to the onset of the disease or disorder, or relative to the expression of TSPAN33 in a control cell. An increased level of TSPAN33 may refer to about a 10% increase, 25% increase, 50% increase, 100% increase, 200% increase, 500% increase, or more.

Also provided herein are methods of treating or preventing a disease or disorder associated with aberrant levels of activated B cells. Aberrant levels of activated B cells may refer to increased levels of activated B cells relative to levels of activated B cells in a control subject (e.g., a healthy subject), or relative to levels of activated B cells in the same subject prior to the onset of the disease or disorder. An increased level of activated B cells may refer to about a 10% increase, 25% increase, 50% increase, 100% increase, 200% increase, 500% increase, or more.

A method herein may comprise administering to a subject in need of treatment an anti-TSPAN33 agent herein. In some embodiments, provided herein are therapeutic antibodies for treating diseases and disorders, including TSPAN33-positive lymphomas and leukemias, as well as autoimmune diseases involving activated B cells. In some embodiments, an anti-TSPAN33 agent is conjugated to a cytotoxic agent, such as radioactive agent, free radical, or toxin. Conjugating an anti-TSPAN33 agent to a cytotoxic agent may improve the therapeutic use of an anti-TSPAN33 agent, for example by increasing the potency of the antibody through the delivery of a cytotoxic agent to a specific target (e.g., activated B cell, diseased B cell) using the anti-TSPAN33 agent as a targeting agent. In some embodiments, an anti-TSPAN33 agent is not conjugated to a cytotoxic agent.

An anti-TSPAN33 agent herein can target activated and/or diseased B cells expressing TSPAN33 and lead to their depletion via complement mediated cytotoxicity (CMC) or antibody dependent cellular cytotoxicity (ADCC), or by altering cell behavior. In certain instances, an anti-TSPAN33 agent is used as an antibody-drug conjugate to increase the killing ability of the antibody against cells expressing TSPAN33.

Also provided herein are methods of selectively targeting TSPAN33-positive cells in a subject, comprising administering to the subject an anti-TSPAN33 agent described herein. Selectively targeting TSPAN33-positive cells generally refers to binding of an anti-TSPAN33 agent to TSPAN33-positive cells and not binding (or not significantly binding) to other cells or cell types. An anti-TSPAN33 agent is considered to not significantly bind to certain cell types when the anti-TSPAN33 agent binds to a cell type at a level that is about 10% or less relative to binding of the anti-TSPAN33 agent to TSPAN33-positive cells. In some embodiments, the anti-TSPAN33 agent binds to TSPAN33 on TSPAN33-positive cells. In some embodiments, the anti-TSPAN33 agent binds to TSPAN33 on TSPAN33-positive cells and does not bind to, or does not significantly bind to, TSPAN33-negative cells. TSPAN33-positive cells may include, for example, B cells, activated B cells, monocytes, activated monocytes, monocytes in the presence of activated B cells, monocytes in the presence of activated PBMCs, T cells, activated T cells, endothelial cells, epithelial cells, lymphoid cells, cells of the central nervous system, and the like. In some embodiments, TSPAN33-positive cells comprise activated B cells. In some embodiments, TSPAN33-positive cells comprise diseased cells. In some embodiments, TSPAN33-positive cells comprise diseased B cells. In some embodiments, TSPAN33-positive cells comprise cancerous cells. In some embodiments, TSPAN33-positive cells comprise cancerous B cells.

Also provided herein are methods of selectively targeting activated B cells in a subject, comprising administering to the subject an anti-TSPAN33 agent described herein. Selectively targeting activated B cells generally refers to binding of an anti-TSPAN33 agent to activated B cells and not binding (or not significantly binding) to other cells or cell types. An anti-TSPAN33 agent is considered to not significantly bind to certain cell types when the anti-TSPAN33 agent binds to a cell type at a level that is about 10% or less relative to binding of the anti-TSPAN33 agent to activated B cells and/or diseased B cells. In some embodiments, the anti-TSPAN33 agent binds to TSPAN33 on activated B cells. In some embodiments, the anti-TSPAN33 agent binds to TSPAN33 on diseased B cells. In some embodiments, the anti-TSPAN33 agent binds to TSPAN33 on activated B cells and does not bind to, or does not significantly bind to, other types of immune cells (e.g., T cells). In some embodiments, the anti-TSPAN33 agent binds to TSPAN33 on activated B cells and does not bind to, or does not significantly bind to, resting B cells. In some embodiments, the anti-TSPAN33 agent binds to TSPAN33 on diseased B cells and does not bind to, or does not significantly bind to, healthy B cells.

An anti-TSPAN33 agent described herein, or component thereof (e.g., one or more CDRs, one or more variable light chains, one or more variable heavy chains) may be expressed by a therapeutic cell. For example, an anti-TSPAN33 agent described herein, or component thereof (e.g., one or more CDRs, one or more variable light chains, one or more variable heavy chains) may be expressed by chimeric antigen receptor modified T (CAR-T) cells. CAR T-cells are modified T cells useful for immunotherapy for certain diseases (e.g., cancer). Typically, a sample of a patient's T cells are collected from the blood, then modified to produce chimeric antigen receptors (CARs) on their surface. In certain instances, a CAR may comprise an anti-TSPAN33 agent described herein, or component thereof (e.g., one or more CDRs, one or more variable light chains, one or more variable heavy chains). In certain instances, a CAR may comprise an anti-TSPAN33 component described herein, in combination with any anti-TSPAN33 component (e.g., one or more CDRs provided herein combined with any other anti-TSPAN33 CDR or CDRs; one or more variable light chains provided herein combined with any other anti-TSPAN33 heavy chain or heavy chains; one or more variable heavy chains provided herein combined with any other anti-TSPAN33 light chain or light chains).

In some embodiments, provided herein are methods of treating certain types of lymphoma or leukemia (e.g., types of lymphoma or leukemia that are TSPAN33-positive). Lymphoma types may include, for example, Hodgkin's disease, non-Hodgkin's lymphoma, diffuse large B cell lymphoma, Burkitt's lymphoma, precursor T-cell leukemia/lymphoma, follicular lymphoma, mantle cell lymphoma, B-cell chronic lymphocytic leukemia/lymphoma, MALT lymphoma, peripheral T-cell lymphoma, nodular sclerosis form of Hodgkin's lymphoma, and mixed-cellularity subtype of Hodgkin's lymphoma. Leukemia types may include, for example, acute lymphocytic leukemia, acute myeloid leukemia, chronic lymphocytic leukemia, chronic myeloid leukemia, hairy cell leukemia, and myelodysplastic syndromes.

In some embodiments, provided herein are methods of treating certain types of allergies or autoimmune diseases (e.g., allergies and autoimmune diseases that are TSPAN33-positive). For example, hypersensitive allergic B lymphocytes can be depleted using TSPAN33 as a target for therapeutic antibodies. Likewise, autoreactive B lymphocytes could similarly be depleted, using TSPAN33 as a target for therapeutic antibodies. Autoimmune diseases may include, for example, rheumatoid arthritis, psoriasis, atopic dermatitis, Sjogren's syndrome, autoimmune hepatitis, primary biliary cirrhosis, ulcerative colitis, Crohn's disease, scleroderma, hypersensitivity pneumonitis, autoimmune thyroditis, hashimoto thyroiditis, Graves' disease, ankylosing spondylitis, Celiac disease, idiopathic thrombocytopenic purpura, mixed connective tissue disease, multiple sclerosis, multiple myeloma, pemphigus vulgaris, temporal arteritis, vitiligo, and systemic lupus erythematosus.

Articles of Manufacture

In another aspect of the invention, an article of manufacture containing materials useful for the treatment, or diagnosis, of the disorders described above is provided. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the anti-TSPAN33 antibody. The label on, or associated with, the container indicates that the composition is used for treating, or diagnosing, the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be better understood by reference to the following Examples, which are intended to merely illustrate the best mode now known for practicing the invention. The scope of the invention should not be considered limited thereto.

EXAMPLES

The examples set forth below illustrate certain embodiments and do not limit the technology. The invention will be further described by reference to the following detailed examples. These Examples are in no way should be considered to limit the scope of the invention in any manner.

Example 1: Creation and Characterization of Anti-TSPAN33 Hybridomas

Hybridomas that secrete monoclonal antibody that reacts with TSPAN33 as expressed in vivo on activated B cells and lymphomas can be prepared as described in this Example. The resulting anti-TSPAN33 antibodies can be used to identify activated B cells in human tissue samples and human lymphoma cells.

Common strains of laboratory mice, e.g., BALB/c or C57/Bl6, or rats, e.g., Sprague Dawley, are suitable hosts for immunization with a TSPAN33 immunogen, e.g., an extracellular region of human TSPAN33 or cells that have been engineered to express human TSPAN33 on their cell membranes. Following successful immunization of mice, hybridomas are formed using standard protocols to fuse myeloma cells with spleen and draining lymph node cells harvested from the animals. Following selection of successful fusions in HAT medium and cloning to approximately one cell/well in microtiter plates, the culture supernatants can be tested against TSPAN33-expressing cell transfectants, e.g., HEK 293 or RBL, by flow cytometry. Wells with successful staining profiles are then subcultured into larger vessels until sufficient cells are present to allow subcloning. Further characterization of the hybridoma subclone candidates can again be performed by flow cytometry using TSPAN33-transfected cells. Clones selected as the best candidates are then further screened, for example, by flow cytometry against human blood cells divided into distinct subsets (e.g., lymphocytes, monocytes, granulocytes, etc.) as well as against one or more cell lines generated from diseased human cells, e.g., lymphoma cells, known to have up-regulated TSPAN33 expression. As compared to an isotype control, the percentage of positive cells in each blood cell subset can be quantified. The ideal candidate clone will have strong reactivity against diseased human cells that express TSPAN33 but no appreciable reactivity against other blood cell populations.

Example 2: Detection of Cells Expressing TSPAN33

This example describes flow cytometry-based detection of human peripheral blood mononuclear cells (PBMCs) using a preferred murine anti-TSPAN33 monoclonal antibody.
Materials and Methods Human peripheral blood mononuclear cells (PBMCs) were isolated in aseptic conditions through a gradient of Ficoll-Paque PLUS (GE Healthcare) according manufacturer instructions. The PBMCs were counted and adjusted in complete RPMI-1640 (10% fetal bovine serum, 1000 U/ml Penicillin, and 1 mg/ml Streptomycin) to a cell density of $1 \times 10^6$ cells/mL. Cells were activated by adding CD40L (TNFSF5; 1 µg/mL) and recombinant human IL-4 (100 U/mL) to the culture. The cells were incubated overnight at 37° C. with 5% $CO_2$.

The next day the cells were washed with Biolegend's Cell Staining Buffer, and $1 \times 10^6$ cells were stained for 15 minutes in the dark with anti-human CD20-APC and purified anti-human TSPAN33 or purified mouse IgG2b, k isotype control, in a volume of 100 µL. Cells were washed twice with 3 mL of Cell Staining Buffer and then stained for 15 minutes in the dark with anti-mouse IgG PE, in a volume of 100 µL. Then the cells were washed twice with 3 mL of Cell Staining Buffer and analyzed on a flow cytometer. 7-AAD Viability Staining Solution was used to exclude dead cells from analysis.

All the reagents used are from BioLegend unless otherwise indicated.
Results

Figure 1:
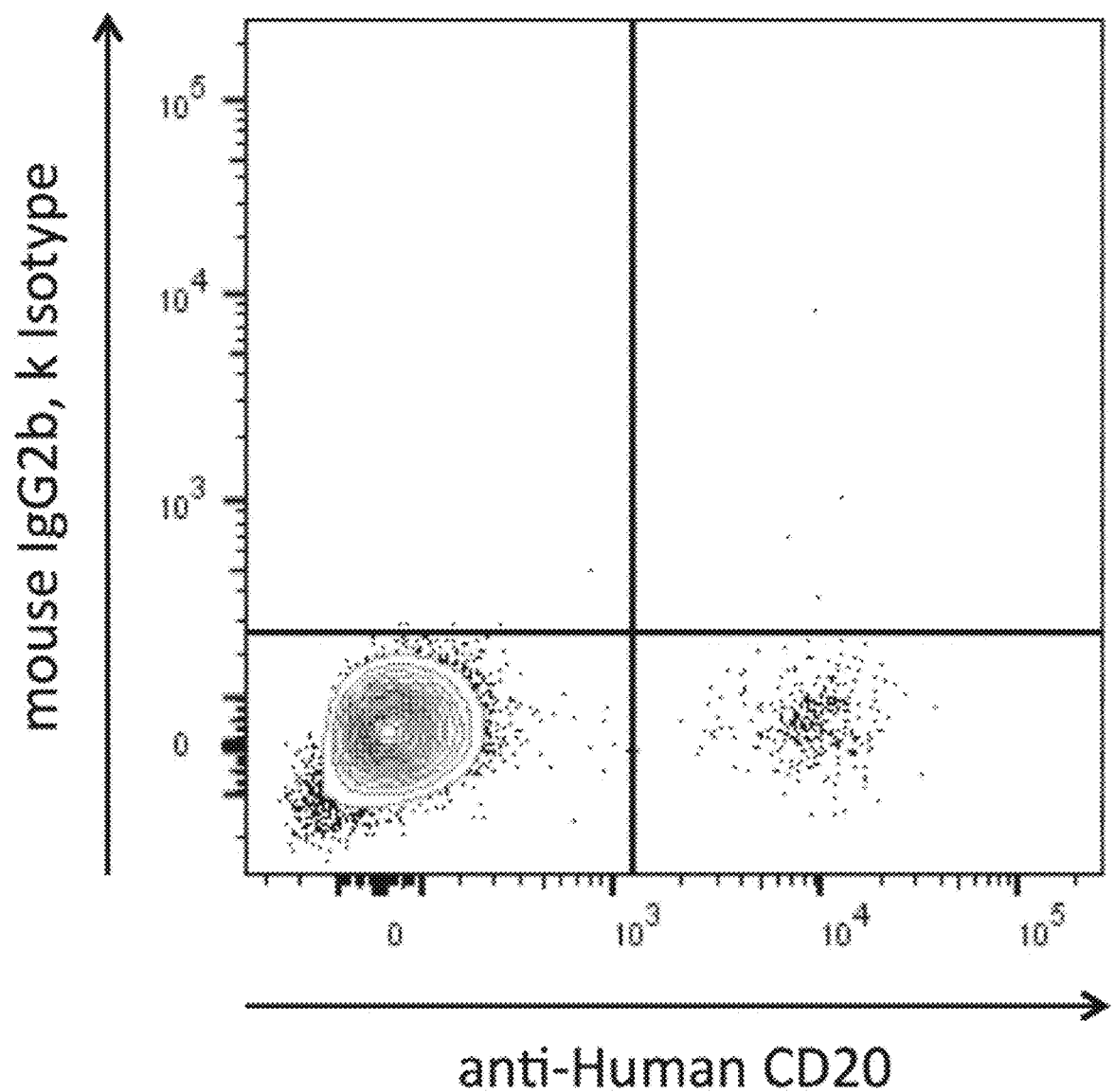
FIG. 1 and FIG. 2 show cytograms of experiments described in Example 2, below. Briefly, human peripheral blood lymphocytes were stimulated overnight with recombinant human CD40L plus IL-4, and stained with CD20 APC and purified mouse IgG2b, k isotype control (FIG. 1) or a purified murine monoclonal anti-TSPAN33 antibody according to the invention (FIG. 2) and then stained with anti-mouse IgG PE.
Figure 2:
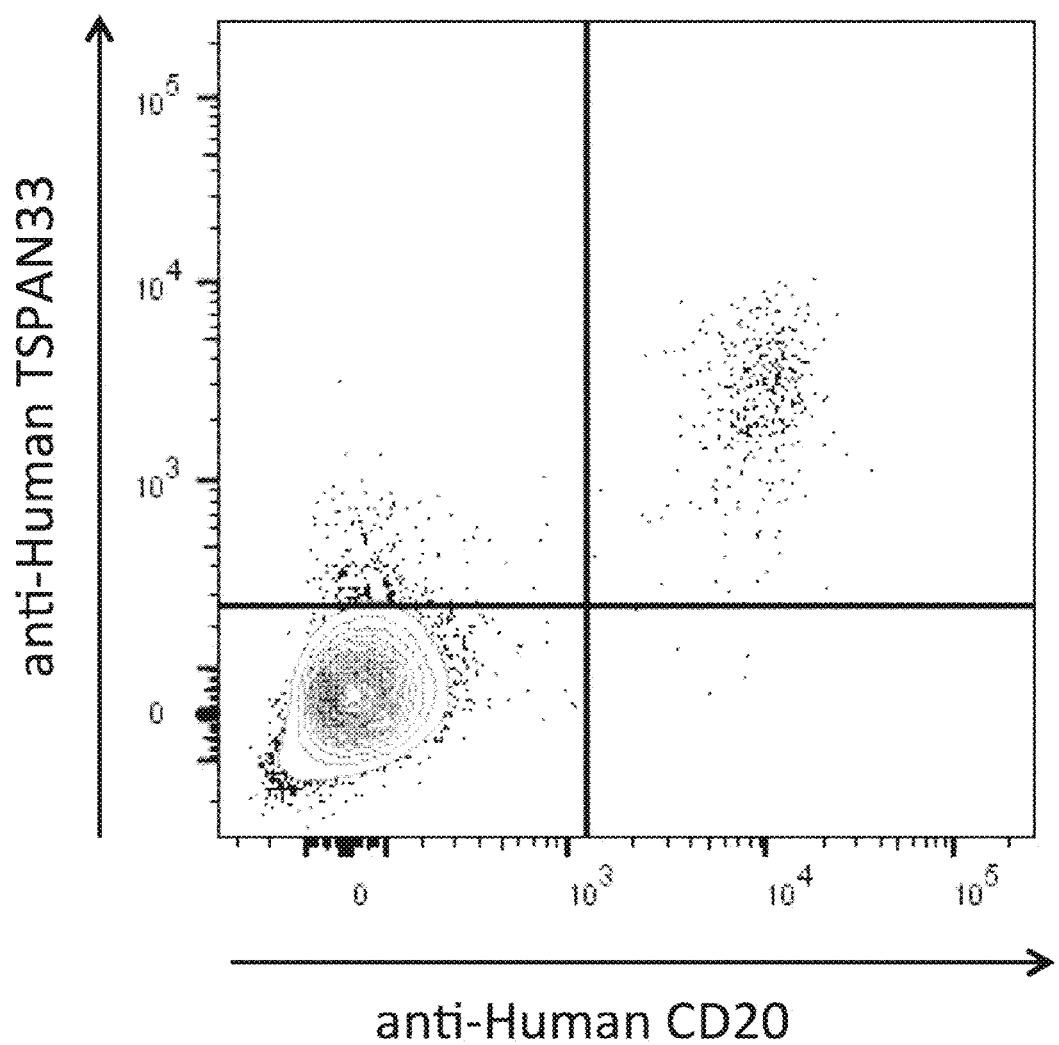

Human B cells stimulated with CD40L and IL-4 exhibit enhanced TSPAN33 expression. The majority of the B cells (CD20+) and a small fraction of the CD20– cells experienced upregulated TSPAN33 expression and were stained with anti-human TSPAN33. In contrast, the isotype control antibody did not stain either population. See FIGS. 1 and 2.

Example 3: Sequencing of the Anti-TSPAN33 Antibody Variable Regions

Cells from a well-performing anti-TSPAN33 hybridoma cell line (described in Example 2, above) were grown in standard mammalian tissue culture media. Total RNA was isolated from hybridoma cells using a procedure based on the RNeasy Mini kit (Qiagen). The RNA was used to generate first strand cDNA. Both light chain and heavy chain variable domain cDNAs were amplified by a 5'-RACE technique. Positive clones were prepared by PCR and then subject to DNA sequencing of multiple clones.

Amino acid sequences of the individual variable domains (CDR1, CDR2, CDR3) for both the heavy and light chains are shown in Table 1, below.

TABLE 1

Mouse TSPAN33 CDR amino acid sequences of the mouse VH and VL domains for a mouse anti-TSPAN33 monoclonal antibody of the invention

|  | CDR | SEQ ID NO: |
|---|---|---|
| $V_H$ CDR Sequence | | |
| DYYMT | CDRH1 | 1 |
| FIRNKANGYTTEYSASVKG | CDRH2 | 2 |
| YLQTGNFDY | CDRH3 | 3 |
| $V_L$ CDR Sequence | | |
| RASQDISNFLN | CDRL1 | 5 |
| FTSRLHS | CDRL2 | 6 |
| QQGYTVPPT | CDRL3 | 7 |

Amino acid sequences of the entire variable region (leader, CDRs and Framework regions) for both heavy and light chains of clone 24 are shown in Table 2, below.

TABLE 2

Mouse TSPAN33 heavy chain and light chain variable region amino acid sequences

| Sequence | SEQ ID NO: |
|---|---|
| Heavy Chain Variable Region | |
| EVKLVESGGGLVQPGGSLSLSCAASGFTFTDYYMTVVVRQPPGKA LEWLVFIRNKANGYTTEYSASVKGRFTISRDNSQSILYLQMNALR AEDSATYYCARYLQTGNFDYWGQGTTLTVSS | 4 |
| Light Chain Variable Region | |
| EIQMIQTTSSLTASLGDRVTISCRASQDISNFLNWYQQKPDGTIK LLIYFTSRLHSGVPSRFSGSGSGTDYSLTISNLEQEDIATYFCQQ GYTVPPTFGGGTKLEIK | 8 |

Example 4: Anti-TSPAN33 Antibody Sequences

TABLE 3

CDR Sequences and Sequence ID Numbers of VH and VL domains for representative mouse anti-TSPAN33 monoclonal antibodies

| SEQ ID NO | CDR Type | AB (clone) Number | Amino Acid Sequence |
|---|---|---|---|
| 1 | CDRH1 | 1 | DYYMT |
| 9 | CDRH1 | 2 | SYWMH |
| 17 | CDRH1 | 3 | NYYMN |
| 25 | CDRH1 | 4 | NYYMN |
| 33 | CDRH1 | 5 | SYWMH |
| 2 | CDRH2 | 1 | FIRNKANGYTTEYSASVKG |
| 10 | CDRH2 | 2 | RIDPNSGGTKYNEKFKS |
| 18 | CDRH2 | 3 | DIIPNNGGTIYNQKFKG |
| 26 | CDRH2 | 4 | DIIPNNGGTIYNQKFKG |
| 34 | CDRH2 | 5 | EINPNNGGSNYNEKFKN |
| 3 | CDRH3 | 1 | YLQTGNFDY |
| 11 | CDRH3 | 2 | FIITGYFDY |
| 19 | CDRH3 | 3 | RLWSWYFDV |
| 27 | CDRH3 | 4 | RLWSWYFDV |
| 35 | CDRH3 | 5 | SYYSYWYFDY |
| 5 | CDRL1 | 1 | RASQDISNFLN |
| 13 | CDRL1 | 2 | KASQDVGAAVA |
| 21 | CDRL1 | 3 | SASSSVSYMY |
| 29 | CDRL1 | 4 | SASSSVSYMY |
| 37 | CDRL1 | 5 | SASSSVNYMH |
| 6 | CDRL2 | 1 | FTSRLHS |
| 14 | CDRL2 | 2 | WASTRHT |
| 22 | CDRL2 | 3 | LTSNLAS |
| 30 | CDRL2 | 4 | LTSNLAS |
| 38 | CDRL2 | 5 | DTSKLAP |
| 7 | CDRL3 | 1 | QQGYTVPPT |
| 15 | CDRL3 | 2 | HQYRTYPFT |
| 23 | CDRL3 | 3 | QQWSSNPYT |
| 31 | CDRL3 | 4 | QQWSSNPYT |
| 39 | CDRL3 | 5 | HQWNNYPYT |

TABLE 4

Mouse TSPAN33 heavy chain and light chain variable region amino acid sequences

| Sequence | SEQ ID NO: |
|---|---|
| Heavy Chain Variable Regions | |
| EVKLVESGGGLVQPGGSLSLSCAASGFTFTDYYMTVVVRQPPGKALEVVLVFIRNKANGY TTEYSASVKGRFTISRDNSQSILYLQMNALRAEDSATYYCARYLQTGNFDYWGQGTTLT VSS | 4 |
| QVQLQQPGAELLKPGASVKLSCKASGYTFTSYVVMHVVVKQRPGRGLEWIGRIDPNSGG TKYNEKFKSKATLTVDKPSSTAYIHLSSLTSEDSAVYYCARFIITGYFDYWGQGTTLIVSS | 12 |
| EAQLQQSGPELVKPGASVKISCKASGYTFTNYYMNVVMKQSHGKSLEWIGDIIPNNGGT IYNQKFKGKATLTVDRSSSTAYMELRSLTSEDSAVYYCARRLWSVVYFDVWGTGTTVTV SS | 20 |
| EVQLQQSGPELVKPGASVKISCKASGYTFTNYYMNVVMKQSHGKSLEWIGDIIPNNGGT IYNQKFKGKATLTVDRSSSTAYMELRSLTSEDSAVYYCARRLWSVVYFDVWGTGTTVTV SS | 28 |

TABLE 4-continued

Mouse TSPAN33 heavy chain and light chain variable region amino acid sequences

| Sequence | SEQ ID NO: |
|---|---|
| QVQLQQPGAEFVKPGASVKLSCKASGYTFTSYVVMHVVVKQRPGQGLEWIGEINPNNG GSNYNEKFKNKATLTVDKSSSTAYMQLSGLTSEDSAVYYCTRSYYSYVVYFDYWGQGT TLTVSS | 36 |
| Light Chain Variable Regions | |
| EIQMIQTTSSLTASLGDRVTISCRASQDISNFLNVVYQQKPDGTIKLLIYFTSRLHSGVP SRFSGSGSGTDYSLTISNLEQEDIATYFCQQGYTVPPTFGGGTKLEIK | 8 |
| DIVMTQSHKFMSTSVGDRVSITCKASQDVGAAVAVVYQQKPGQSPKWYWASTRHTGV PDRFTGSGSGTDFTLTISTVQSEDLADYFCHQYRTYPFTFGSGTKLGIK | 16 |
| QIVLTQSPALMSASPGEKVTMTCSASSSVSYMYVVYQQKPRSSPKPWIYLTSNLASGVP ARFSGSGSGTSYSLTISSMEAEDAATYYCQQWSSNPYTFGGGTKLEIK | 24 |
| QIVLTQSPALMSASPGEKVTMTCSASSSVSYMYVVYQQKPRSSPKPWIYLTSNLASGVP ARFSGSGSGTSYSLTISSMEAEDAATYYCQQWSSNPYTFGGGTKLEIK | 32 |
| QIVLTQSPAIMSASPGQKVTITCSASSSVN-YMHVVYQQKLGSSPKLWIYDTSKLAPGVPA RFSGSGSGTSYSLTISNMEAEDAASYFCHQVVNNYPYTFGSGTKLEIK | 40 |

Example 5: Detection of Cells Expressing TSPAN33 and a Blocking Assay

This example describes flow cytometry-based detection of activated B cells and monocytes using murine anti-TSPAN33 monoclonal antibodies provided herein. This example also describes a blocking assay performed using the anti-TSPAN33 antibodies described herein.

B Cell Activation

Human peripheral blood mononuclear cells (PBMCs) were isolated in aseptic conditions through a gradient of Ficoll-Paque PLUS (GE Healthcare) according manufacturer instructions; then the cells were counted and adjusted at a cell density of 1×10$^6$ cells/mL with RPMI 1640 (Gibco Laboratories), supplemented with 10% FBS and antibiotics, plus CD40L (TNFSFS) (BioLegend, cat. #591704) 1 μg/mL and IL-4 (BioLegend, cat. #574002) 100 U/mL, and were incubated overnight at 37° C., 5% CO2.

Surface and Staining

The PBMCs were counted and adjusted in Cell Staining Buffer (BioLegend, cat. #420201) to a cell density of 1×10$^7$ cells/mL. A 100 μl cell suspension (1×10$^6$ total cells) was stained with CD20 APC (BioLegend, cat. #150412) and the indicated anti-TSPAN33 antibody for 15 minutes in the dark. Cells were washed twice with 2 mL of Cell Staining Buffer. For cell acquisition by flow cytometry the cells were resuspended in 300 μL Cell Staining Buffer plus 20 μL of DAPI (BioLegend, cat. #422801). The samples were acquired on a BD FACSCanto II, and analyzed using FlowJo software (Tree Star Inc).

Flow Cytometry/Gating Hierarchy

Figure 4:
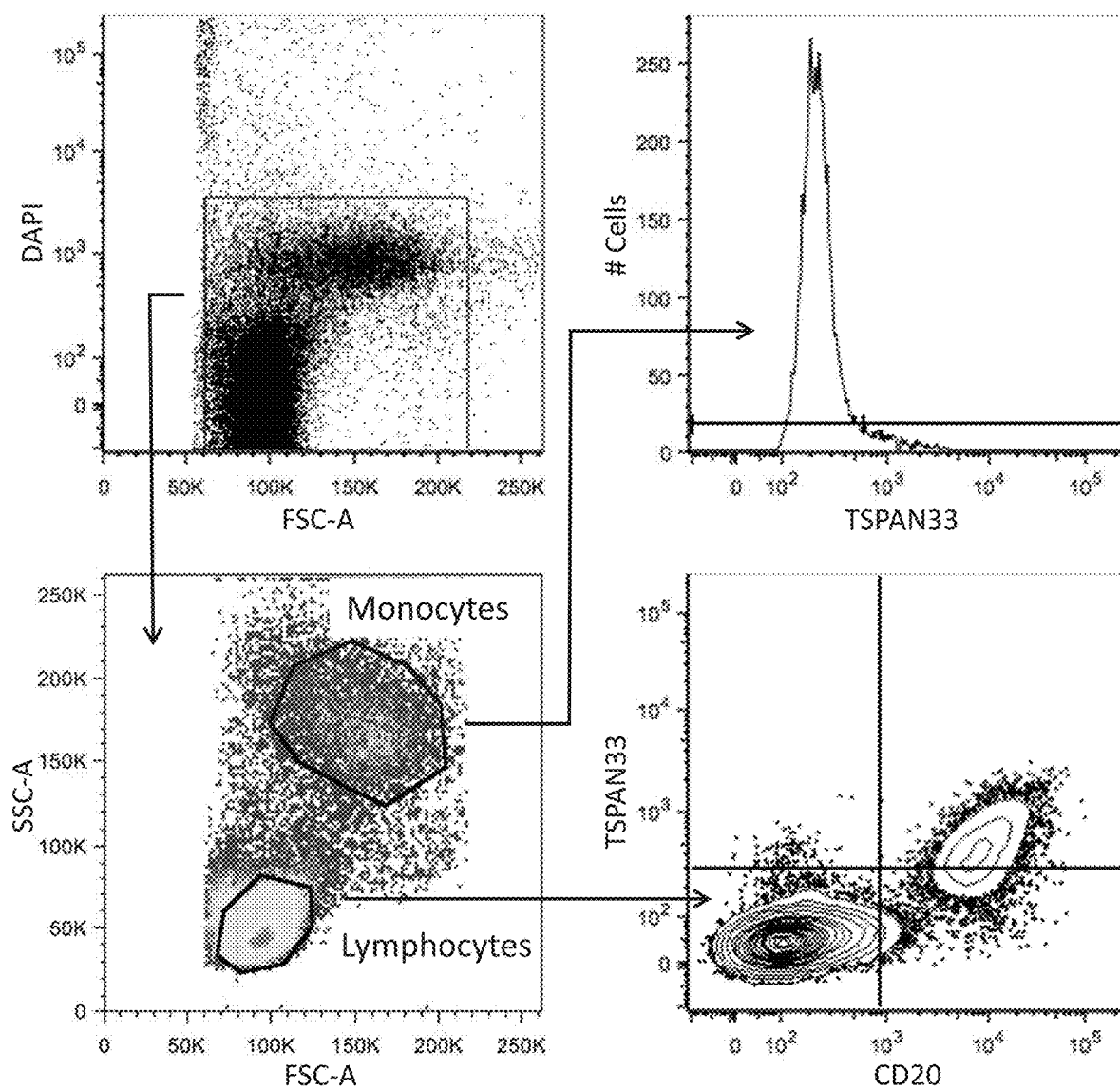
FIG. 4 shows scatter plots showing the gating strategy used to detect TSPAN33 by flow cytometry in the experiments described in Example 5, below.
Figure 5A:
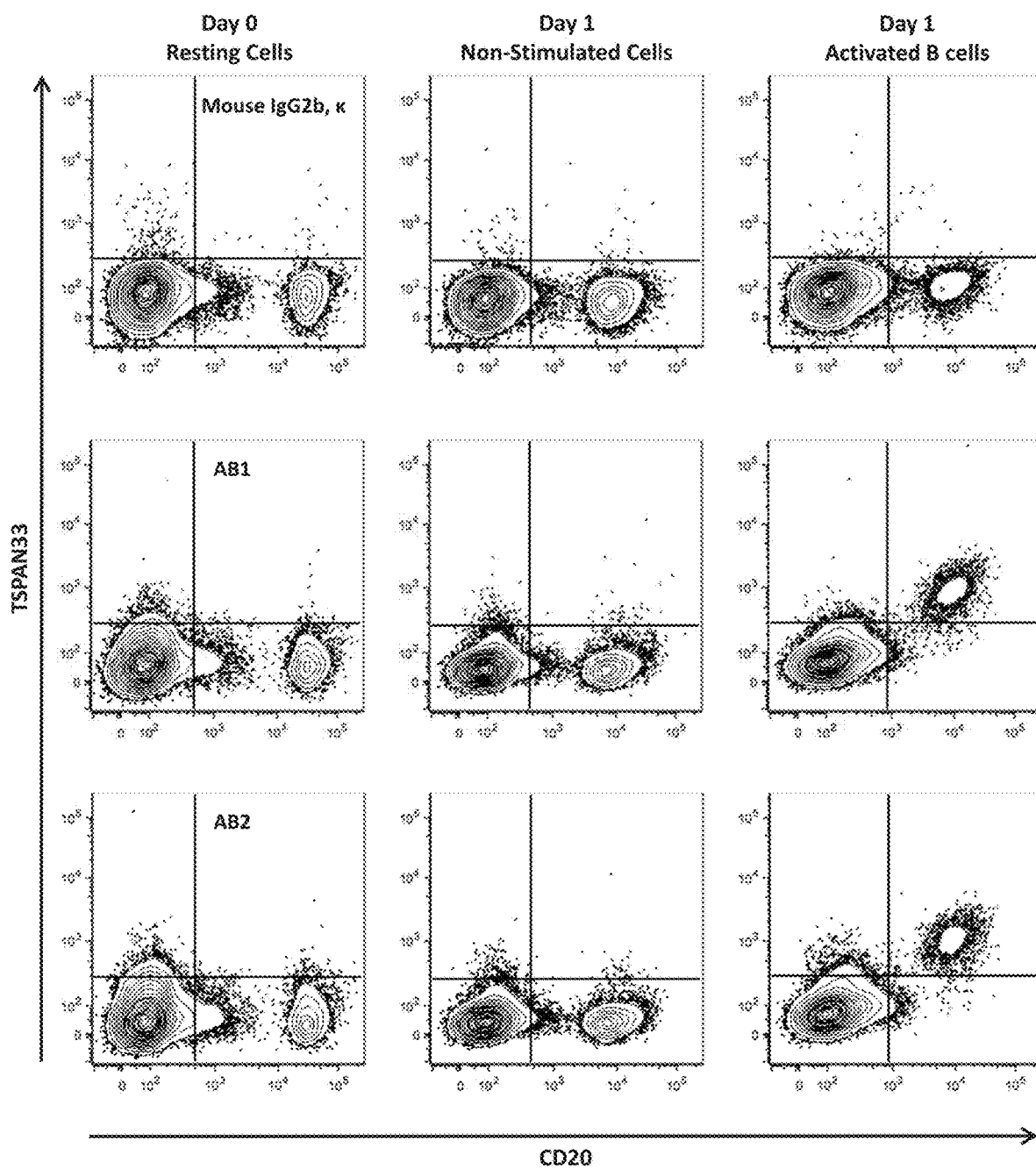
FIG. 5A and FIG. 5B show expression of TSPAN33 on resting PBMCs from peripheral blood (left), PBMCs cultured overnight without stimulation (middle), or PBMCs activated overnight with CD40L (TNFSF5) plus IL-4 (right). Data is gated on lymphocytes ($FSC^{lo}SSC^{lo}$). B cells were identified by co-staining with an anti-human CD20 monoclonal antibody. Quadrant gates are based on isotype staining (Mouse IgG2b, κ).
Figure 5B:
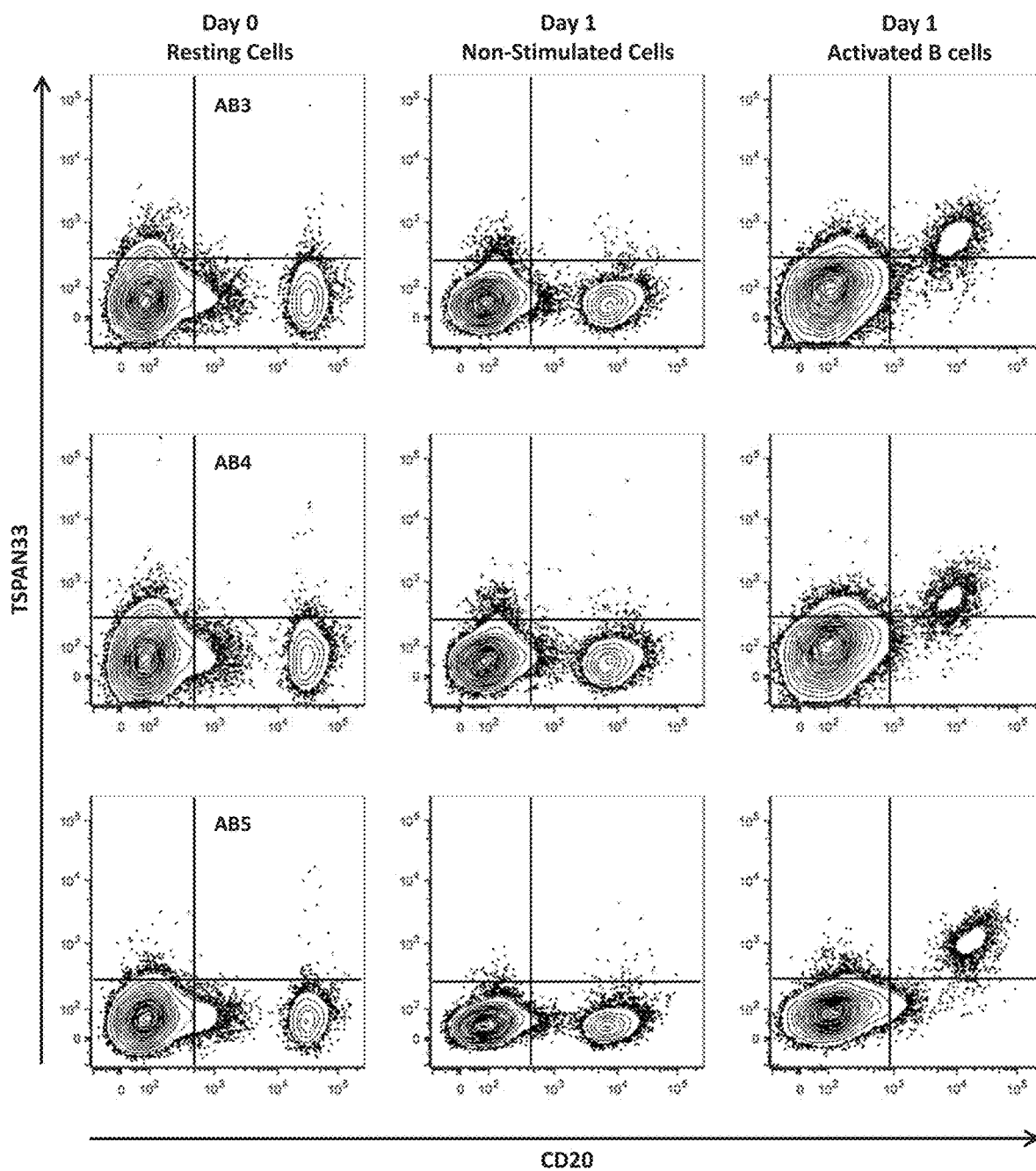
Figure 6A:
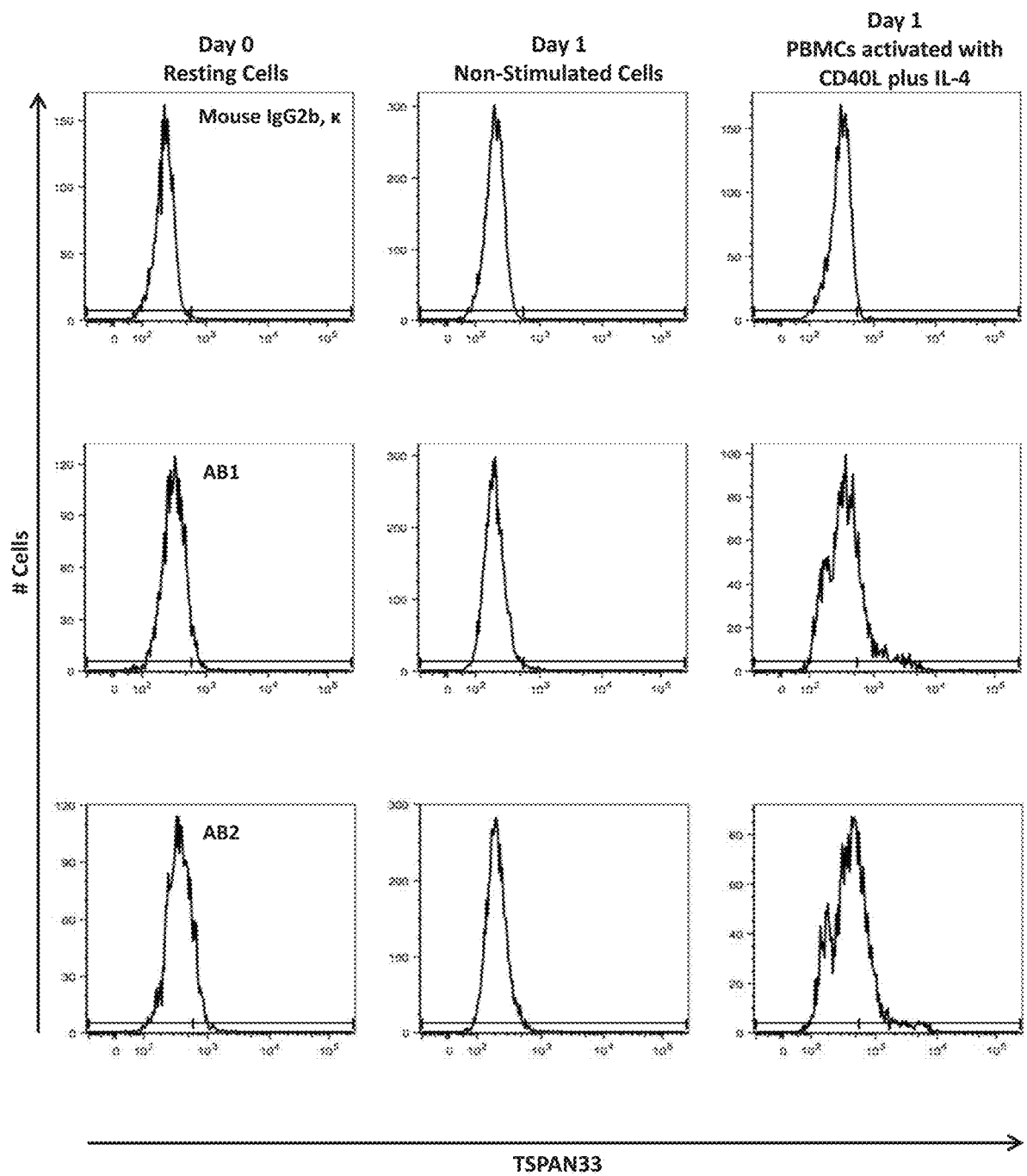
FIG. 6A and FIG. 6B show expression of TSPAN33 on resting PBMCs from peripheral blood (left), PBMCs cultured overnight without stimulation (middle), or PBMCs activated overnight with CD40L (TNFSF5) plus IL-4 (right).
Figure 6B:
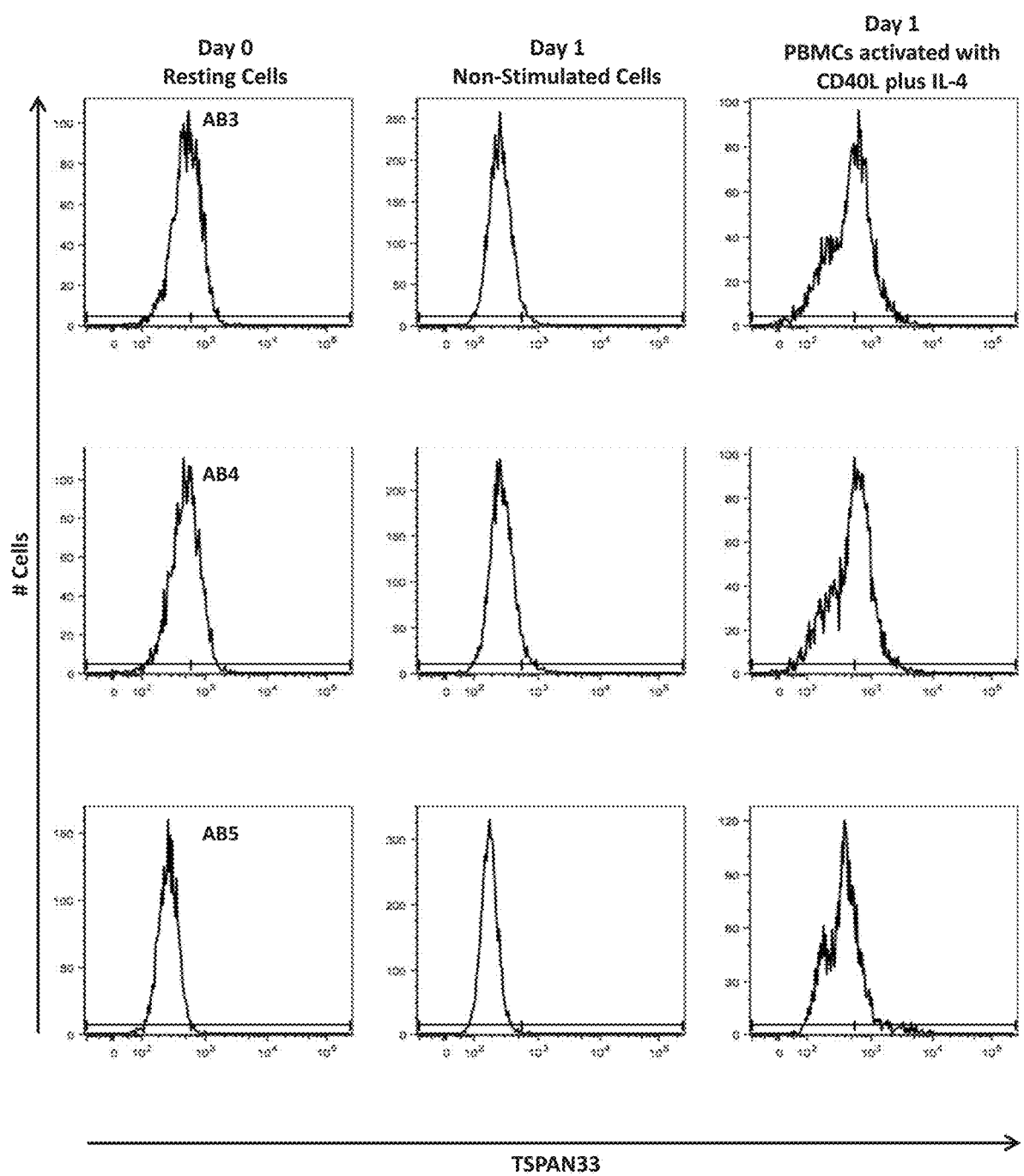

Dead cells were excluded of the analysis based on the staining DAPI; lymphocytes and monocytes were gated based on their forward (FSC) and side scatter (SSC) profiles (FIG. 4). Lymphocytes were FSC$^{lo}$SSC$^{lo}$ and monocytes were FSC$^{int}$SSC$^{int}$. From the lymphocyte gate, B cells were identified as CD20$^+$. A dot plot was generated for the lymphocyte population (FIG. 5A and FIG. 5B) and a histogram was generated for the monocyte population (FIG. 6A and FIG. 6B).

Blocking Assay

For blocking studies, resting or activated PBMCs were incubated with 10 μg purified antibody anti-TSPAN33 (AB1, AB2, AB3, AB4, and AB5) or mouse IgG2b, κ isotype control for 15 minutes and then stained with CD20 APC, and mouse IgG2b, κ, PE (BioLegend, cat. #400312) or the indicated anti-TSPAN33 antibody (AB1, AB2, AB3, AB4, and AB5).

Calculations for % Blocking

Percentage original Median Fluorochrome Intensity (MFI) was calculated by dividing the MFI of samples blocked with isotype controls or AB1, AB2, AB3, AB4, AB5 by the MFI without blocking. This value was subtracted from 100 to get a blocking percentage. The formula is shown below:

$$100 - \left(\frac{[MFI\ blocking]}{[MFI\ noblocking]}\right) * 100$$

Blocking Assay Results

Staining results for isotype control (no blocking; top histogram in each panel of FIGS. 7A, 7B, 8A, 8B) and each of anti-TSPAN33 antibodies AB1, AB2, AB3, AB4, AB5 (no blocking; second histogram from the top in each panel of FIGS. 7A, 7B, 8A, 8B; each panel numbered according to the respective staining antibody #) are presented in FIGS. 7A, 7B, 8A, 8B. In most instances, Mouse IgG2b did not significantly alter the MFI (median fluorescent intensity) of TSPAN expressed by activated B cells or monocytes (third histogram (from the top) in each panel of FIGS. 7A, 7B, 8A, 8B). AB1, AB2, AB3, AB4, and AB5 used in the blocking assay reduced the MFI of TSPAN33 expression by a percentage ranging from about 61% to about 90% on activated B cells and from about 12% to about 40% on monocytes. Overall, AB1, AB2, AB3, AB4, and AB5 used in the blocking assay reduced the MFI of TSPAN33 expression by an average 80.3% on activated B cells and 28.7% on monocytes (bottom five histograms in each panel of FIGS. 7A, 7B, 8A, 8B). FIG. 9 and FIG. 10 show summaries of TSPAN33 blocking on activated B cells and monocytes, respectively. The tables in FIG. 11 present MFI and % blocking results for activated B cells (left table) and monocytes (right table).

Example 6: Examples of Embodiments

The examples set forth below illustrate certain embodiments and do not limit the technology.

A1. An anti-TSPAN33 agent, optionally, an isolated, non-naturally occurring antibody, or antigen-binding fragment or derivative thereof, that binds Tetraspanin 33 (TSPAN33) under physiological conditions, wherein the agent comprises at least one immunoglobulin heavy chain variable domain and one immunoglobulin light chain variable domain, wherein:
  (a) each immunoglobulin heavy chain variable domain of the anti-TSPAN33 agent comprises first, second, and third heavy chain complementarity determining regions (CDRs), wherein the first heavy chain CDR comprises an amino acid sequence that has a sequence identity of at least 65 percent, optionally a sequence identity of at least 80 percent, at least 90 percent, at least 95 percent, and 100 percent identity with the amino acid sequence DYYMT (SEQ ID NO:1), the second heavy chain CDR comprises an amino acid sequence that has a sequence identity of at least 65 percent, optionally a sequence identity of at least 80 percent, at least 90 percent, at least 95 percent, and 100 percent identity with the amino acid sequence FIRNKANGYTTEYSASVKG (SEQ ID NO:2), and the third heavy chain CDR comprises an amino acid sequence that has a sequence identity of at least 65 percent, optionally a sequence identity of at least 80 percent, at least 90 percent, at least 95 percent, and 100 percent identity with the amino acid sequence YLQTGNFDY (SEQ ID NO:3); and,
  (b) each immunoglobulin light chain variable domain of the anti-TSPAN33 agent comprises first, second, and third light chain CDRs, wherein the first light chain CDR comprises an amino acid sequence that has a sequence identity of at least 65 percent, optionally a sequence identity of at least 80 percent, at least 90 percent, at least 95 percent, and 100 percent identity with the amino acid sequence RASQDISNFLN (SEQ ID NO:5), the second light chain CDR comprises an amino acid sequence that has a sequence identity of at least 65 percent, optionally a sequence identity of 100 percent identity with the amino acid sequence FTSRLHS (SEQ ID NO:6), and the third light chain CDR comprises an amino acid sequence that has a sequence identity of at least 65 percent, optionally a sequence identity of at least 80 percent, at least 90 percent, at least 95 percent, and 100 percent identity with the amino acid sequence QQGYTVPPT (SEQ ID NO:7).

A2. An anti-TSPAN33 agent according to embodiment A1 that comprises a non-naturally occurring anti-TSPAN33 antibody, or TSPAN33-binding fragment or derivative thereof, wherein the first heavy chain CDR comprises the amino acid sequence DYYMT (SEQ ID NO:1), the second heavy chain CDR comprises the amino acid sequence FIRNKANGYTTEYSASVKG (SEQ ID NO:2), the third heavy chain CDR comprises the amino acid sequence YLQTGNFDY (SEQ ID NO:3), the first light chain CDR comprises the amino acid sequence RASQDISNFLN (SEQ ID NO:5), the second light chain CDR comprises the amino acid sequence FTSRLHS (SEQ ID NO:6), and the third light chain CDR comprises the amino acid sequence QQGYTVPPT (SEQ ID NO:7).

A3. An anti-TSPAN33 agent according to embodiment A1 is a humanized antibody or an antigen-binding fragment or derivative of a humanized antibody that binds TSPAN33.

A4. A composition comprising a carrier, optionally a pharmaceutically acceptable carrier, and an anti-TSPAN33 agent according to embodiment A1.

A5. A composition according to embodiment A4, wherein the anti-TSPAN33 agent according to embodiment A1 is a humanized antibody or an antigen-binding fragment or derivative of a humanized antibody that binds TSPAN33.

A6. An anti-TSPAN33 agent according to embodiment A1 that comprises an anti-TSPAN33 antibody, or TSPAN33-binding fragment or derivative thereof wherein each immunoglobulin heavy chain variable domain comprises an amino acid sequence that has a sequence identity of at least 65 percent, optionally a sequence identity of at least 80 percent, at least 90 percent, at least 95 percent, and 100 percent identity with the amino acid sequence (SEQ ID NO: 4)
EVKLVESGGGLVQPGGSLSLSCAASGFTFTDYYMTWVRQPPGKALEWLVF

IRNKANGYTTEYSASVKGRFTISRDNSQSILYLQMNALRAEDSATYYCAR

YLQTGNFDYWGQGTTLTVSS, and each immunoglobulin light chain variable domain comprises an amino acid sequence that has a sequence identity of at least 65 percent, optionally a sequence identity of at least 80 percent, at least 90 percent, at least 95 percent, and 100 percent identity with the amino acid sequence (SEQ ID NO: 8)
EIQMIQTTSSLTASLGDRVTISCRASQDISNFLNWYQQKPDGTIKLLIYF

TSRLHSGVPSRFSGSGSGTDYSLTISNLEQEDIATYFCQQGYTVPPTFGG

GTKLEIK.

A7. An anti-TSPAN33 agent according to embodiment A1 that comprises a non-naturally occurring anti-TSPAN33 antibody, or TSPAN33-binding fragment or derivative thereof, wherein each immunoglobulin heavy chain variable domain comprises the amino acid sequence (SEQ ID NO: 4)
EVKLVESGGGLVQPGGSLSLSCAASGFTFTDYYMTWVRQPPGKALEWLVF

IRNKANGYTTEYSASVKGRFTISRDNSQSILYLQMNALRAEDSATYYCAR

YLQTGNFDYWGQGTTLTVSS, and each immunoglobulin light chain variable domain comprises the amino acid sequence (SEQ ID NO: 8)
EIQMIQTTSSLTASLGDRVTISCRASQDISNFLNWYQQKPDGTIKLLIYF

TSRLHSGVPSRFSGSGSGTDYSLTISNLEQEDIATYFCQQGYTVPPTFGG

GTKLEIK.

A8. An anti-TSPAN33 agent according to embodiment A1 that is a humanized antibody or an antigen-binding fragment or derivative of a humanized antibody that binds TSPAN33.

A9. A composition comprising a carrier, optionally a pharmaceutically acceptable carrier, and an anti-TSPAN33 agent according to embodiment A7.

A10. A composition according to embodiment A9, wherein the anti-TSPAN33 agent is a humanized antibody or an antigen-binding fragment or derivative of a humanized antibody that binds TSPAN33.

A11. A diagnostic kit configured to detect Tetraspanin 33 (TSPAN33) in a biological sample, the kit comprising an anti-TSPAN33 agent according to embodiment A1 conjugated with a detectable marker or non-diffusively immobilized on a solid support.

A12. An anti-TSPAN33 agent according to embodiment A1 that further comprises a detectable label.

A13. A labeled anti-TSPAN33 agent according to embodiment A12 wherein the anti-TSPAN33 agent is a humanized antibody or an antigen-binding fragment or derivative of a humanized antibody that binds TSPAN33.

A14. A composition comprising a carrier, optionally a pharmaceutically acceptable carrier, and a labeled anti-TSPAN33 agent according to embodiment A12.

A15. An agent-drug conjugate comprising an anti-TSPAN33 agent according to embodiment A1 and a drug moiety, wherein the drug moiety optionally comprises a nucleic acid, a peptide, a polypeptide, a small molecule, or an aptamer.

A16. An agent-drug conjugate according to embodiment A15 wherein the anti-TSPAN33 agent is a humanized antibody or an antigen-binding fragment or derivative of a humanized antibody that binds TSPAN33.

A17. A composition comprising a carrier, optionally a pharmaceutically acceptable carrier, and an agent-drug conjugate according to embodiment A15.

A18. An isolated nucleic acid molecule selected from the group consisting of (i) a nucleic acid molecule that encodes an immunoglobulin heavy chain variable domain of an antibody, or antigen-binding fragment or derivative thereof, that binds Tetraspanin 33 (TSPAN33) under physiological conditions, wherein the nucleic acid molecule encodes first, second, and third heavy chain complementarity determining regions (CDRs), wherein the first heavy chain CDR comprises an amino acid sequence that has a sequence identity of at least 65 percent, optionally a sequence identity of at least 80 percent, at least 90 percent, at least 95 percent, and 100 percent identity with the amino acid sequence DYYMT (SEQ ID NO:1), the second heavy chain CDR comprises an amino acid sequence that has a sequence identity of at least 65 percent, optionally a sequence identity of at least 80 percent, at least 90 percent, at least 95 percent, and 100 percent identity with the amino acid sequence FIRNK-ANGYTTEYSASVKG (SEQ ID NO:2), and the third heavy chain CDR comprises an amino acid sequence that has a sequence identity of at least 65 percent, optionally a sequence identity of at least 80 percent, at least 90 percent, at least 95 percent, and 100 percent identity with the amino acid sequence YLQTGNFDY (SEQ ID NO:3), and (ii) a nucleic acid molecule that encodes an immunoglobulin light chain variable domain of an antibody, or antigen-binding fragment or derivative thereof, that binds TSPAN33 under physiological conditions, wherein the nucleic acid molecule encodes first, second, and third light chain CDRs, wherein the first light chain CDR comprises an amino acid sequence that has a sequence identity of at least 65 percent, optionally a sequence identity of at least 80 percent, at least 90 percent, at least 95 percent, and 100 percent identity with the amino acid sequence RASQDISNFLN (SEQ ID NO:5), the second light chain CDR comprises an amino acid sequence that has a sequence identity of at least 65 percent, optionally a sequence identity of 100 percent identity with the amino acid sequence FTSRLHS (SEQ ID NO:6), and the third light chain CDR comprises an amino acid sequence that has a sequence identity of at least 65 percent, optionally a sequence identity of at least 80 percent, at least 90 percent, at least 95 percent, and 100 percent identity with the amino acid sequence QQGYTVPPT (SEQ ID NO:7).

A19. An isolated nucleic acid molecule according to embodiment A18 selected from the group consisting of (i) a nucleic acid molecule that encodes an immunoglobulin heavy chain variable domain of an antibody, or antigen-binding fragment or derivative thereof, that binds TSPAN33, wherein the first heavy chain CDR comprises the amino acid sequence DYYMT (SEQ ID NO:1), the second heavy chain CDR comprises the amino acid sequence FIRNK-ANGYTTEYSASVKG (SEQ ID NO:2), and the third heavy chain CDR comprises the amino acid sequence YLQTGNFDY (SEQ ID NO:3), and (ii) a nucleic acid molecule that encodes an immunoglobulin light chain variable domain of an antibody, or antigen-binding fragment or derivative thereof, that binds TSPAN33 under physiological conditions, wherein the first light chain CDR comprises the amino acid sequence RASQDISNFLN (SEQ ID NO:5), the second light chain CDR comprises the amino acid sequence FTSRLHS (SEQ ID NO:6), and the third light chain CDR comprises the amino acid sequence QQGYTVPPT (SEQ ID NO:7).

A20. An isolated nucleic acid molecule according to embodiment A18 selected from the group consisting of (i) a nucleic acid molecule that encodes an immunoglobulin heavy chain variable domain that comprises an amino acid sequence that has a sequence identity of at least 65 percent, optionally a sequence identity of at least 80 percent, at least 90 percent, at least 95 percent, and 100 percent identity with the amino acid sequence

```
                                              (SEQ ID NO: 4)
EVKLVESGGGLVQPGGSLSLSCAASGFTFTDYYMTWVRQPPGKALEWLVF

IRNKANGYTTEYSASVKGRFTISRDNSQSILYLQMNALRAEDSATYYCAR

YLQTGNFDYWGQGTTLTVSS
``` of an antibody, or antigen-binding fragment or derivative thereof, that binds TSPAN33 under physiological conditions, and (ii) a nucleic acid molecule that encodes an immunoglobulin light chain variable domain that comprises an amino acid sequence that has a sequence identity of at least 65 percent, optionally a sequence identity of at least 80 percent, at least 90 percent, at least 95 percent, and 100 percent identity with the amino acid sequence

```
                                              (SEQ ID NO: 8)
EIQMIQTTSSLTASLGDRVTISCRASQDISNFLNWYQQKPDGTIKLLIYF

TSRLHSGVPSRFSGSGSGTDYSLTISNLEQEDIATYFCQQGYTVPPTFGG

GTKLEIK
``` of an antibody, or antigen-binding fragment or derivative thereof, that binds TSPAN33 under physiological conditions.

A21. A recombinant expression vector that comprises first and second expression cassettes, the first expression cassette comprising a promoter and a nucleic acid molecule that encodes an immunoglobulin heavy chain variable domain of an antibody, or antigen-binding fragment or derivative thereof, that binds TSPAN33, wherein the first heavy chain CDR comprises an amino acid sequence that has a sequence identity of at least 65 percent, optionally a sequence identity of at least 80 percent, at least 90 percent, at least 95 percent, and 100 percent identity with the amino acid sequence DYYMT (SEQ ID NO:1), the second heavy chain CDR comprises an amino acid sequence that has a sequence identity of at least 65 percent, optionally a sequence identity of at least 80 percent, at least 90 percent, at least 95 percent, and 100 percent identity with the amino acid sequence FIRNKANGYTTEYSASVKG (SEQ ID NO:2), and the third heavy chain CDR comprises an amino acid sequence that has a sequence identity of at least 65 percent, optionally a sequence identity of at least 80 percent, at least 90 percent, at least 95 percent, and 100 percent identity with the amino acid sequence YLQTGNFDY (SEQ ID NO:3), and a second expression cassette comprising a promoter and a nucleic acid molecule that encodes an immunoglobulin light chain variable domain of an antibody, or antigen-binding fragment or derivative thereof, that binds TSPAN33, wherein the first light chain CDR comprises an amino acid sequence that has a sequence identity of at least 65 percent, optionally a sequence identity of at least 80 percent, at least 90 percent, at least 95 percent, and 100 percent identity with the amino acid sequence RASQDISNFLN (SEQ ID NO:5), the second light chain CDR comprises an amino acid sequence that has a sequence identity of at least 65 percent, optionally a sequence identity of 100 percent identity with the amino acid sequence FTSRLHS (SEQ ID NO:6), and the third light chain CDR comprises an amino acid sequence that has a sequence identity of at least 65 percent, optionally a sequence identity of at least 80 percent, at least 90 percent, at least 95 percent, and 100 percent identity with the amino acid sequence QQGYTVPPT (SEQ ID NO:7).

A22. A recombinant host cell transfected with a recombinant expression vector according to embodiment A21.

A23. A method of treating or preventing a disease or disorder associated with aberrant levels of TSPAN33, comprising administering to a subject in need of such treatment an anti-TSPAN33 agent according to embodiment A1 in an amount sufficient to effect treatment, thereby treating or preventing the disease or disorder.

A24. A method according to embodiment A23 selected from the group consisting of leukemia; lymphoma; optionally, Hodgkin's disease, non-Hodgkin's lymphoma, diffuse large B cell lymphoma, and Burkitt's lymphoma; and an autoimmune disease, optionally rheumatoid arthritis.

B1. An anti-TSPAN33 agent that binds Tetraspanin 33 (TSPAN33) under laboratory or physiological conditions, wherein the agent comprises at least one immunoglobulin heavy chain variable domain and/or at least one immunoglobulin light chain variable domain, wherein:
  a) each immunoglobulin heavy chain variable domain of the anti-TSPAN33 agent comprises first, second, and third heavy chain complementarity determining regions (CDRs), wherein
  the first heavy chain CDR (CDRH1) comprises a polypeptide that is at least 75 percent identical to the amino acid sequence $X_1YX_2MX_3$ (SEQ ID NO: 41), wherein
    $X_1$ is D, S or N,
    $X_2$ is Y or W, and
    $X_3$ is N, H or T;
  the second heavy chain CDR (CDRH2) comprises a polypeptide that is at least 75 percent identical to the amino acid sequence $X_1IX_2X_3X_4X_5X_6GX_7X_8X_9X_{10}YX_{11}X_{12}X_{13}X_{14}KX_{15}$ (SEQ ID NO: 42), wherein
    $X_1$ is F, R, D or E,
    $X_2$ is R, D, I or N,
    $X_3$ is N or P,
    $X_4$ is N or K,
    $X_5$ is A, S or N,
    $X_6$ is N or G,
    $X_7$ is Y or no amino acid,
    $X_8$ is T or no amino acid,
    $X_9$ is T or S,
    $X_{10}$ is E, K, I or N,
    $X_{11}$ is S or N,
    $X_{12}$ is A, E or Q,
    $X_{13}$ is S or K,
    $X_{14}$ is V or F, and
    $X_{15}$ is G, S or N; and
  the third heavy chain CDR (CDRH3) comprises a polypeptide that is at least 75 percent identical to the amino acid sequence $X_1X_2X_3X_4X_5X_6X_7FDX_8$ (SEQ ID NO: 43), wherein
    $X_1$ is no amino acid or S,
    $X_2$ is Y, F or R,
    $X_3$ is L, I or Y,
    $X_4$ is Q, I, W or S,
    $X_5$ is T, S or Y,
    $X_6$ is G or W,
    $X_7$ is N or Y, and
    $X_8$ is Y or V; and/or
  b) each immunoglobulin light chain variable domain of the anti-TSPAN33 agent comprises first, second, and third light chain CDRs, wherein
  the first light chain CDR (CDRL1) comprises a polypeptide that is at least 75 percent identical to the amino acid sequence $X_1ASX_2X_3X_4X_5X_6X_7X_8X_9$ (SEQ ID NO: 44), wherein
    $X_1$ is R, K or S,
    $X_2$ is Q or S,
    $X_3$ is D or S,
    $X_4$ is I or V,
    $X_5$ is S, G or N,
    $X_6$ is N, A or no amino acid,
    $X_7$ is F, A or Y,
    $X_8$ is L, V or M, and
    $X_9$ is N, A, Y or H;
  the second light chain CDR (CDRL2) comprises a polypeptide that is at least 75 percent identical to the amino acid sequence $X_1X_2SX_3X_4X_5X_6$ (SEQ ID NO: 45), wherein
    $X_1$ is F, W, L or D,
    $X_2$ is T or A,
    $X_3$ is R, T, N or K,
    $X_4$ is L or R,
    $X_5$ is H or A, and
    $X_6$ is S, T or P; and
  the third light chain CDR (CDRL3) comprises a polypeptide that is at least 75 percent identical to the amino acid sequence $X_1QX_2X_3X_4X_5PX_6T$ (SEQ ID NO: 46), wherein
    $X_1$ is Q or H,
    $X_2$ is G, Y or W,
    $X_3$ is Y, R, S or N,
    $X_4$ is T, S or N,
    $X_5$ is V, Y or N, and
    $X_6$ is P, F or Y.

B1.1 An anti-TSPAN33 agent that binds Tetraspanin 33 (TSPAN33) under laboratory or physiological conditions, wherein the agent comprises at least one immunoglobulin heavy chain variable domain and at least one immunoglobulin light chain variable domain, wherein:

a) each immunoglobulin heavy chain variable domain of the anti-TSPAN33 agent comprises first, second, and third heavy chain complementarity determining regions (CDRs), wherein the first heavy chain CDR (CDRH1) comprises a polypeptide that is at least 75 percent identical to the amino acid sequence $X_1YX_2MX_3$ (SEQ ID NO: 41), wherein
$X_1$ is D, S or N,
$X_2$ is Y or W, and
$X_3$ is N, H or T;

the second heavy chain CDR (CDRH2) comprises a polypeptide that is at least 75 percent identical to the amino acid sequence $X_1IX_2X_3X_4X_5X_6GX_7X_8X_9X_{10}YX_{11}X_{12}X_{13}X_{14}KX_{15}$ (SEQ ID NO: 42), wherein
$X_1$ is F, R, D or E,
$X_2$ is R, D, I or N,
$X_3$ is N or P,
$X_4$ is N or K,
$X_5$ is A, S or N,
$X_6$ is N or G,
$X_7$ is Y or no amino acid,
$X_8$ is T or no amino acid,
$X_9$ is T or S,
$X_{10}$ is E, K, I or N,
$X_{11}$ is S or N,
$X_{12}$ is A, E or Q,
$X_{13}$ is S or K,
$X_{14}$ is V or F, and
$X_{15}$ is G, S or N; and the third heavy chain CDR (CDRH3) comprises a polypeptide that is at least 75 percent identical to the amino acid sequence $X_1X_2X_3X_4X_5X_6X_7FDX_8$ (SEQ ID NO: 43), wherein
$X_1$ is no amino acid or S,
$X_2$ is Y, F or R,
$X_3$ is L, I or Y,
$X_4$ is Q, I, W or S,
$X_5$ is T, S or Y,
$X_6$ is G or W,
$X_7$ is N or Y, and
$X_8$ is Y or V; and b) each immunoglobulin light chain variable domain of the anti-TSPAN33 agent comprises first, second, and third light chain CDRs, wherein the first light chain CDR (CDRL1) comprises a polypeptide that is at least 75 percent identical to the amino acid sequence $X_1ASX_2X_3X_4X_5X_6X_7X_8X_9$ (SEQ ID NO: 44), wherein
$X_1$ is R, K or S,
$X_2$ is Q or S,
$X_3$ is D or S,
$X_4$ is I or V,
$X_5$ is S, G or N,
$X_6$ is N, A or no amino acid,
$X_7$ is F, A or Y,
$X_8$ is L, V or M, and
$X_9$ is N, A, Y or H;

the second light chain CDR (CDRL2) comprises a polypeptide that is at least 75 percent identical to the amino acid sequence $X_1X_2SX_3X_4X_5X_6$ (SEQ ID NO: 45), wherein
$X_1$ is F, W, L or D,
$X_2$ is T or A,
$X_3$ is R, T, N or K,
$X_4$ is L or R,
$X_5$ is H or A, and
$X_6$ is S, T or P; and the third light chain CDR (CDRL3) comprises a polypeptide that is at least 75 percent identical to the amino acid sequence $X_1QX_2X_3X_4X_5PX_6T$ (SEQ ID NO: 46), wherein
$X_1$ is Q or H,
$X_2$ is G, Y or W,
$X_3$ is Y, R, S or N,
$X_4$ is T, S or N,
$X_5$ is V, Y or N, and
$X_6$ is P, F or Y.

B2. The anti-TSPAN33 agent of embodiment B1 or B1.1, wherein the CDRH1 comprises a polypeptide that is at least 80 percent identical to the amino acid sequence of SEQ ID NO: 41.

B3. The anti-TSPAN33 agent of embodiment B1 or B1.1, wherein the CDRH1 comprises a polypeptide that is at least 85 percent identical to the amino acid sequence of SEQ ID NO: 41.

B4. The anti-TSPAN33 agent of embodiment B1 or B1.1, wherein the CDRH1 comprises a polypeptide that is at least 90 percent identical to the amino acid sequence of SEQ ID NO: 41.

B5. The anti-TSPAN33 agent of embodiment B1 or B1.1, wherein the CDRH1 comprises a polypeptide that is at least 95 percent identical to the amino acid sequence of SEQ ID NO: 41.

B6. The anti-TSPAN33 agent of embodiment B1 or B1.1, wherein the CDRH1 comprises a polypeptide that is 100 percent identical to the amino acid sequence of SEQ ID NO: 41.

B7. The anti-TSPAN33 agent of any one of embodiments B1 to B6, wherein the CDRH2 comprises a polypeptide that is at least 80 percent identical to the amino acid sequence of SEQ ID NO: 42.

B8. The anti-TSPAN33 agent of any one of embodiments B1 to B6, wherein the CDRH2 comprises a polypeptide that is at least 85 percent identical to the amino acid sequence of SEQ ID NO: 42.

B9. The anti-TSPAN33 agent of any one of embodiments B1 to B6, wherein the CDRH2 comprises a polypeptide that is at least 90 percent identical to the amino acid sequence of SEQ ID NO: 42.

B10. The anti-TSPAN33 agent of any one of embodiments B1 to B6, wherein the CDRH2 comprises a polypeptide that is at least 95 percent identical to the amino acid sequence of SEQ ID NO: 42.

B11. The anti-TSPAN33 agent of any one of embodiments B1 to B6, wherein the CDRH2 comprises a polypeptide that is 100 percent identical to the amino acid sequence of SEQ ID NO: 42.

B12. The anti-TSPAN33 agent of any one of embodiments B1 to B11, wherein the CDRH3 comprises a polypeptide that is at least 80 percent identical to the amino acid sequence of SEQ ID NO: 43.

B13. The anti-TSPAN33 agent of any one of embodiments B1 to B11, wherein the CDRH3 comprises a polypeptide that is at least 85 percent identical to the amino acid sequence of SEQ ID NO: 43.

B14. The anti-TSPAN33 agent of any one of embodiments B1 to B11, wherein the CDRH3 comprises a polypeptide that is at least 90 percent identical to the amino acid sequence of SEQ ID NO: 43.

B15. The anti-TSPAN33 agent of any one of embodiments B1 to B11, wherein the CDRH3 comprises a polypeptide that is at least 95 percent identical to the amino acid sequence of SEQ ID NO: 43.

B16. The anti-TSPAN33 agent of any one of embodiments B1 to B11, wherein the CDRH3 comprises a polypeptide that is 100 percent identical to the amino acid sequence of SEQ ID NO: 43.

B17. The anti-TSPAN33 agent of any one of embodiments B1 to B16, wherein the CDRL1 comprises a polypeptide that is at least 80 percent identical to the amino acid sequence of SEQ ID NO: 44.

B18. The anti-TSPAN33 agent of any one of embodiments B1 to B16, wherein the CDRL1 comprises a polypeptide that is at least 85 percent identical to the amino acid sequence of SEQ ID NO: 44.

B19. The anti-TSPAN33 agent of any one of embodiments B1 to B16, wherein the CDRL1 comprises a polypeptide that is at least 90 percent identical to the amino acid sequence of SEQ ID NO: 44.

B20. The anti-TSPAN33 agent of any one of embodiments B1 to B16, wherein the CDRL1 comprises a polypeptide that is at least 95 percent identical to the amino acid sequence of SEQ ID NO: 44.

B21. The anti-TSPAN33 agent of any one of embodiments B1 to B16, wherein the CDRL1 comprises a polypeptide that is 100 percent identical to the amino acid sequence of SEQ ID NO: 44.

B22. The anti-TSPAN33 agent of any one of embodiments B1 to B21, wherein the CDRL2 comprises a polypeptide that is at least 80 percent identical to the amino acid sequence of SEQ ID NO: 45.

B23. The anti-TSPAN33 agent of any one of embodiments B1 to B21, wherein the CDRL2 comprises a polypeptide that is at least 85 percent identical to the amino acid sequence of SEQ ID NO: 45.

B24. The anti-TSPAN33 agent of any one of embodiments B1 to B21, wherein the CDRL2 comprises a polypeptide that is at least 90 percent identical to the amino acid sequence of SEQ ID NO: 45.

B25. The anti-TSPAN33 agent of any one of embodiments B1 to B21, wherein the CDRL2 comprises a polypeptide that is at least 95 percent identical to the amino acid sequence of SEQ ID NO: 45.

B26. The anti-TSPAN33 agent of any one of embodiments B1 to B21, wherein the CDRL2 comprises a polypeptide that is 100 percent identical to the amino acid sequence of SEQ ID NO: 45.

B27. The anti-TSPAN33 agent of any one of embodiments B1 to B26, wherein the CDRL3 comprises a polypeptide that is at least 80 percent identical to the amino acid sequence of SEQ ID NO: 46.

B28. The anti-TSPAN33 agent of any one of embodiments B1 to B26, wherein the CDRL3 comprises a polypeptide that is at least 85 percent identical to the amino acid sequence of SEQ ID NO: 46.

B29. The anti-TSPAN33 agent of any one of embodiments B1 to B26, wherein the CDRL3 comprises a polypeptide that is at least 90 percent identical to the amino acid sequence of SEQ ID NO: 46.

B30. The anti-TSPAN33 agent of any one of embodiments B1 to B26, wherein the CDRL3 comprises a polypeptide that is at least 95 percent identical to the amino acid sequence of SEQ ID NO: 46.

B31. The anti-TSPAN33 agent of any one of embodiments B1 to B26, wherein the CDRL3 comprises a polypeptide that is 100 percent identical to the amino acid sequence of SEQ ID NO: 46.

B32. The anti-TSPAN33 agent of any one of embodiments B1 to B31, wherein the CDRH1 comprises an amino acid sequence chosen from DYYMT (SEQ ID NO: 1), SYWMH (SEQ ID NOs: 9 and 33), and NYYMN (SEQ ID NOs: 17 and 25).

B33. The anti-TSPAN33 agent of any one of embodiments B1 to B32, wherein the CDRH2 comprises an amino acid sequence chosen from FIRNKANGYTTEYSASVKG (SEQ ID NO: 2), RIDPNSGGTKYNEKFKS (SEQ ID NO: 10), DIIPNNGGTIYNQKFKG (SEQ ID NOs: 18 and 26), and EINPNNGGSNYNEKFKN (SEQ ID NO: 34).

B34. The anti-TSPAN33 agent of any one of embodiments B1 to B33, wherein the CDRH3 comprises an amino acid sequence chosen from YLQTGNFDY (SEQ ID NO: 3), FIITGYFDY (SEQ ID NO: 11), RLWSWYFDV (SEQ ID NOs: 19 and 27), and SYYSYWYFDY (SEQ ID NO: 35).

B35. The anti-TSPAN33 agent of any one of embodiments B1 to B34, wherein the CDRL1 comprises an amino acid sequence chosen from RASQDISNFLN (SEQ ID NO: 5), KASQDVGAAVA (SEQ ID NO: 13), SASSSVSYMY (SEQ ID NOs: 21 and 29), and SASSSVNYMH (SEQ ID NO: 37).

B36. The anti-TSPAN33 agent of any one of embodiments B1 to B35, wherein the CDRL2 comprises an amino acid sequence chosen from FTSRLHS (SEQ ID NO: 6), WASTRHT (SEQ ID NO: 14), LTSNLAS (SEQ ID NO: 22 and 30), and DTSKLAP (SEQ ID NO: 38).

B37. The anti-TSPAN33 agent of any one of embodiments B1 to B36, wherein the CDRL3 comprises an amino acid sequence chosen from QQGYTVPPT (SEQ ID NO: 7), HQYRTYPFT (SEQ ID NO: 15), QQWSSNPYT (SEQ ID NO: 23 and 31), and HQWNNYPYT (SEQ ID NO: 39).

B38. The anti-TSPAN33 agent of any one of embodiments B1 to B37, which comprises two immunoglobulin heavy chain variable domains and two immunoglobulin light chain variable domains.

B39. The anti-TSPAN33 agent of embodiment B38, wherein the two immunoglobulin heavy chain variable domains each comprise a set of CDRH1, CDRH2 and CDRH3 amino acid sequences.

B40. The anti-TSPAN33 agent of embodiment B38 or B39, wherein the two immunoglobulin light chain variable domains each comprise a set of CDRL1, CDRL2 and CDRL3 amino acid sequences.

B41. The anti-TSPAN33 agent of any one of embodiments B1 to B40, wherein each immunoglobulin heavy chain variable domain comprises a set of CDRH1, CDRH2 and CDRH3 amino acid sequences and each immunoglobulin light chain variable domain comprises a set of CDRL1, CDRL2 and CDRL3 amino acid sequences chosen from sets 1-4:

| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| 1 | DYYMT (1) | FIRNKANGYTTEYSASVKG (2) | YLQTGNFDY (3) | RASQDISNFLN (5) | FTSRLHS (6) | QQGYTVPPT (7) |

| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| 2 | SYVVMH (9) | RIDPNSGGTKY NEKFKS (10) | F1 ITGYFDY (11) | KASQDVGAA VA (13) | WASTRHT (14) | HQYRTYPFT (15) |
| 3 | NYYMN (17 and 25) | DIIPNNGGTIYN QKFKG (18 and 26) | RLWSVVYFDV (19 and 27) | SASSSVSYM Y (21 and 29) | LTSNLAS (22 and 30) | QQWSSNPY T (23 and 31) |
| 4 | SYVVMH (33) | EINPNNGGSNY NEKFKN (34) | SYYSYVVYFDY (35) | SASSSVNYM H (37) | DTSKLAP (38) | HQWNNYPY T (39) |

B42. The anti-TSPAN33 agent of embodiment B41, wherein all CDR sequences are from the same set.

B43. The anti-TSPAN33 agent of any one of embodiments B1 to B42, wherein the immunoglobulin heavy chain variable domain comprises a polypeptide that is at least 75 percent identical to an amino acid sequence chosen from SEQ ID NO: 4, SEQ ID NO: 12, SEQ ID NO: 20, SEQ ID NO: 28, and SEQ ID NO: 36.

B44. The anti-TSPAN33 agent of any one of embodiments B1 to B42, wherein the immunoglobulin heavy chain variable domain comprises a polypeptide that is at least 80 percent identical to an amino acid sequence chosen from SEQ ID NO: 4, SEQ ID NO: 12, SEQ ID NO: 20, SEQ ID NO: 28, and SEQ ID NO: 36.

B45. The anti-TSPAN33 agent of any one of embodiments B1 to B42, wherein the immunoglobulin heavy chain variable domain comprises a polypeptide that is at least 85 percent identical to an amino acid sequence chosen from SEQ ID NO: 4, SEQ ID NO: 12, SEQ ID NO: 20, SEQ ID NO: 28, and SEQ ID NO: 36.

B46. The anti-TSPAN33 agent of any one of embodiments B1 to B42, wherein the immunoglobulin heavy chain variable domain comprises a polypeptide that is at least 90 percent identical to an amino acid sequence chosen from SEQ ID NO: 4, SEQ ID NO: 12, SEQ ID NO: 20, SEQ ID NO: 28, and SEQ ID NO: 36.

B47. The anti-TSPAN33 agent of any one of embodiments B1 to B42, wherein the immunoglobulin heavy chain variable domain comprises a polypeptide that is at least 95 percent identical to an amino acid sequence chosen from SEQ ID NO: 4, SEQ ID NO: 12, SEQ ID NO: 20, SEQ ID NO: 28, and SEQ ID NO: 36.

B48. The anti-TSPAN33 agent of any one of embodiments B1 to B42, wherein the immunoglobulin heavy chain variable domain comprises an amino acid sequence chosen from SEQ ID NO: 4, SEQ ID NO: 12, SEQ ID NO: 20, SEQ ID NO: 28, and SEQ ID NO: 36.

B48. The anti-TSPAN33 agent of any one of embodiments B1 to B48, wherein the immunoglobulin light chain variable domain comprises a polypeptide that is at least 75 percent identical to an amino acid sequence chosen from SEQ ID NO: 8, SEQ ID NO: 16, SEQ ID NO: 24, SEQ ID NO: 32, and SEQ ID NO: 40.

B49. The anti-TSPAN33 agent of any one of embodiments B1 to B48, wherein the immunoglobulin light chain variable domain comprises a polypeptide that is at least 80 percent identical to an amino acid sequence chosen from SEQ ID NO: 8, SEQ ID NO: 16, SEQ ID NO: 24, SEQ ID NO: 32, and SEQ ID NO: 40.

B50. The anti-TSPAN33 agent of any one of embodiments B1 to B48, wherein the immunoglobulin light chain variable domain comprises a polypeptide that is at least 85 percent identical to an amino acid sequence chosen from SEQ ID NO: 8, SEQ ID NO: 16, SEQ ID NO: 24, SEQ ID NO: 32, and SEQ ID NO: 40.

B51. The anti-TSPAN33 agent of any one of embodiments B1 to B48, wherein the immunoglobulin light chain variable domain comprises a polypeptide that is at least 90 percent identical to an amino acid sequence chosen from SEQ ID NO: 8, SEQ ID NO: 16, SEQ ID NO: 24, SEQ ID NO: 32, and SEQ ID NO: 40.

B52. The anti-TSPAN33 agent of any one of embodiments B1 to B48, wherein the immunoglobulin light chain variable domain comprises a polypeptide that is at least 95 percent identical to an amino acid sequence chosen from SEQ ID NO: 8, SEQ ID NO: 16, SEQ ID NO: 24, SEQ ID NO: 32, and SEQ ID NO: 40.

B53. The anti-TSPAN33 agent of any one of embodiments B1 to B48, wherein the immunoglobulin light chain variable domain comprises an amino acid sequence chosen from SEQ ID NO: 8, SEQ ID NO: 16, SEQ ID NO: 24, SEQ ID NO: 32, and SEQ ID NO: 40.

B54. The anti-TSPAN33 agent of any one of embodiments B1 to B53, wherein the agent is isolated.

B55. The anti-TSPAN33 agent of any one of embodiments B1 to B54, wherein the agent is non-naturally occurring.

B56. The anti-TSPAN33 agent of any one of embodiments B1 to B55, wherein the agent is an antibody, or antigen-binding fragment thereof.

B57. The anti-TSPAN33 agent of any one of embodiments B1 to B55, wherein the agent is an antibody, or derivative thereof.

B58. The anti-TSPAN33 agent of any one of embodiments B1 to B57, wherein the agent is a humanized antibody, or an antigen binding fragment thereof.

B59. The anti-TSPAN33 agent of any one of embodiments B1 to B57, wherein the agent is a derivative of a humanized antibody that binds TSPAN33.

B60. The anti-TSPAN33 agent of any one of embodiments B1 to B59, wherein the agent comprises a detectable marker or label.

B61. The anti-TSPAN33 agent of any one of embodiments B1 to B60, wherein the agent is conjugated to a detectable marker or label.

B62. The anti-TSPAN33 agent of any one of embodiments B1 to B61, wherein the agent is non-diffusively immobilized on a solid support.

B63. A diagnostic reagent comprising the anti-TSPAN33 agent of any one of embodiments B1 to B62.

B64. A kit comprising the anti-TSPAN33 agent of any one of embodiments B1 to B62 or the diagnostic reagent of embodiment B63.

B65. A diagnostic kit configured to detect Tetraspanin 33 (TSPAN33) in a biological sample, wherein the kit comprises the anti-TSPAN33 agent of any one of embodiments B1 to B62 or the diagnostic reagent of embodiment B63.

B66. An isolated nucleic acid molecule comprising a nucleotide sequence that encodes an immunoglobulin heavy chain variable domain of the anti-TSPAN33 agent of any one of embodiments B1 to B62.

B67. An isolated nucleic acid molecule comprising a nucleotide sequence that encodes an immunoglobulin light chain variable domain of the anti-TSPAN33 agent of any one of embodiments B1 to B62.

B68. A recombinant expression vector comprising a first expression cassette and a second expression cassette, wherein the first expression cassette comprises a promoter and a nucleic acid molecule comprising a nucleotide sequence that encodes an immunoglobulin heavy chain variable domain of the anti-TSPAN33 agent of any one of embodiments B1 to B62, and the second expression cassette comprises a promoter and a nucleic acid molecule comprising a nucleotide sequence that encodes an immunoglobulin light chain variable domain of the anti-TSPAN33 agent of any one of embodiments B1 to B62.

B69. A recombinant host cell transfected with the recombinant expression vector of embodiment B68.

B70. A method of detecting TSPAN33, comprising contacting a sample known or suspected to contain TSPAN33 with the anti-TSPAN33 agent of any one of embodiments B1 to B62, and, if the sample contains TSPAN33, detecting TSPAN33:anti-TSPAN33 complexes.

B71. A composition comprising a pharmaceutically acceptable carrier and the anti-TSPAN33 agent of one of embodiments B1 to B62.

B72. An agent-drug conjugate comprising the anti-TSPAN33 agent of any one of embodiments B1 to B62 and a drug moiety.

B73. The agent-drug conjugate of embodiment B72, wherein the drug moiety comprises a nucleic acid, a peptide, a polypeptide, a small molecule, or an aptamer.

B74. A composition comprising a pharmaceutically acceptable carrier and the agent-drug conjugate of embodiment B72 or B73.

B75. A method of diagnosing a disease or disorder associated with aberrant levels of TSPAN33, comprising detecting an aberrant level of TSPAN33 using the anti-TSPAN33 agent of any one of embodiments B1 to B62, thereby diagnosing the disease or disorder.

B76. A method of treating or preventing a disease or disorder associated with aberrant levels of TSPAN33, comprising administering to a subject in need of such treatment the anti-TSPAN33 agent of any one of embodiments B1 to B62 in an amount sufficient to effect treatment, thereby treating or preventing the disease or disorder.

B77. A method of treating or preventing a disease or disorder associated with aberrant levels of TSPAN33, comprising administering to a subject in need of such treatment the agent-drug conjugate of embodiment B72 or B73 in an amount sufficient to effect treatment, thereby treating or preventing the disease or disorder.

B78. The method of embodiment B75, B76, or B77, wherein the disease or disorder is chosen from leukemia, lymphoma, and an autoimmune disease.

B79. The method of embodiment B78, wherein the lymphoma is Hodgkin's disease, non-Hodgkin's lymphoma, diffuse large B cell lymphoma, or Burkitt's lymphoma.

B80. The method of embodiment B78, wherein the autoimmune disease is rheumatoid arthritis.

B81. A method of selectively targeting activated B cells in a subject, comprising administering to the subject the anti-TSPAN33 agent of any one of embodiments B1 to B62, wherein the anti-TSPAN33 agent binds to TSPAN33 on activated B cells.

B82. A method of selectively targeting activated B cells in a subject, comprising administering to the subject the agent-drug conjugate of embodiment B72 or B73, wherein the anti-TSPAN33 agent in the agent-drug conjugate binds to TSPAN33 on activated B cells.

B83. The method of embodiment B81 or B82, wherein the anti-TSPAN33 agent does not bind to T cells.

B84. The method of any one of embodiments B81 to B83, wherein the subject has a disease or disorder chosen from leukemia, lymphoma, and an autoimmune disease.

B85. The method of embodiment B84, wherein the lymphoma is Hodgkin's disease, non-Hodgkin's lymphoma, diffuse large B cell lymphoma, or Burkitt's lymphoma.

B86. The method of embodiment B84, wherein the autoimmune disease is rheumatoid arthritis.

B87. A chimeric antigen receptor modified T (CAR-T) cell comprising the anti-TSPAN33 agent of any one of embodiments B1 to B62, or the isolated nucleic acid molecule of embodiment B66 or B67.

C1. A first anti-TSPAN33 agent that binds Tetraspanin 33 (TSPAN33) under laboratory or physiological conditions, wherein the first agent competitively binds, or is capable of competitively binding, with a second anti-TSPAN33 agent, which second agent is the anti-TSPAN33 agent of any one of embodiments B1 to B62.

C2. A first anti-TSPAN33 agent that binds Tetraspanin 33 (TSPAN33) on a cell under laboratory or physiological conditions, wherein the first agent competitively binds, or is capable of competitively binding, with a second anti-TSPAN33 agent, which second agent is the anti-TSPAN33 agent of any one of embodiments B1 to B62.

C3. A first anti-TSPAN33 agent that binds Tetraspanin 33 (TSPAN33) on activated B cells under laboratory or physiological conditions, wherein the first agent competitively binds, or is capable of competitively binding, with a second anti-TSPAN33 agent, which second agent is the anti-TSPAN33 agent of any one of embodiments B1 to B62.

C4. A first anti-TSPAN33 agent that binds Tetraspanin 33 (TSPAN33) under laboratory or physiological conditions, wherein the first agent binds to, or is capable of binding to, the same epitope as a second anti-TSPAN33 agent, which second agent is the anti-TSPAN33 agent of any one of embodiments B1 to B62.

C5. The first anti-TSPAN33 agent of any one of embodiments C1 to C4, which is isolated.

C6. The first anti-TSPAN33 agent of any one of embodiments C1 to C5, which is non-naturally occurring.

C7. The first anti-TSPAN33 agent of any one of embodiments C1 to C6, which is an antibody, or antigen-binding fragment thereof.

C8. The first anti-TSPAN33 agent of any one of embodiments C1 to C6, which is an antibody, or derivative thereof.

C9. The first anti-TSPAN33 agent of any one of embodiments C1 to C8, which is a humanized antibody, or an antigen binding fragment thereof.

C10. The first anti-TSPAN33 agent of any one of embodiments C1 to C8, which is a derivative of a humanized antibody that binds TSPAN33.

C11. The first anti-TSPAN33 agent of any one of embodiments C1 to C10, which comprises a detectable marker or label.

C12. The first anti-TSPAN33 agent of any one of embodiments C1 to C11, which is conjugated to a detectable marker or label.

C13. The first anti-TSPAN33 agent of any one of embodiments C1 to C12, wherein the agent is non-diffusively immobilized on a solid support.

C14. A diagnostic reagent comprising the first anti-TSPAN33 agent of any one of embodiments C1 to C13.

C15. A kit comprising the first anti-TSPAN33 agent of any one of embodiments C1 to C13 or the diagnostic reagent of embodiment C14.

C16. A diagnostic kit configured to detect Tetraspanin 33 (TSPAN33) in a biological sample, wherein the kit comprises the first anti-TSPAN33 agent of any one of embodiments C1 to C13 or the diagnostic reagent of embodiment C14.

C17. An isolated nucleic acid molecule comprising a nucleotide sequence that encodes an immunoglobulin heavy chain variable domain of the first anti-TSPAN33 agent of any one of embodiments C1 to C13.

C18. An isolated nucleic acid molecule comprising a nucleotide sequence that encodes an immunoglobulin light chain variable domain of the first anti-TSPAN33 agent of any one of embodiments C1 to C13.

C19. A recombinant expression vector comprising a first expression cassette and a second expression cassette, wherein the first expression cassette comprises a promoter and a nucleic acid molecule comprising a nucleotide sequence that encodes an immunoglobulin heavy chain variable domain of the first anti-TSPAN33 agent of any one of embodiments C1 to C13, and the second expression cassette comprises a promoter and a nucleic acid molecule comprising a nucleotide sequence that encodes an immunoglobulin light chain variable domain of the first anti-TSPAN33 agent of any one of embodiments C1 to C13.

C20. A recombinant host cell transfected with the recombinant expression vector of embodiment C19.

C21. A method of detecting TSPAN33, comprising contacting a sample known or suspected to contain TSPAN33 with the first anti-TSPAN33 agent of any one of embodiments C1 to C13, and, if the sample contains TSPAN33, detecting TSPAN33:anti-TSPAN33 complexes.

C22. A composition comprising a pharmaceutically acceptable carrier and the first anti-TSPAN33 agent of one of embodiments C1 to C13.

C23. An agent-drug conjugate comprising the first anti-TSPAN33 agent of any one of embodiments C1 to C13 and a drug moiety.

C24. The agent-drug conjugate of embodiment C23, wherein the drug moiety comprises a nucleic acid, a peptide, a polypeptide, a small molecule, or an aptamer.

C25. A composition comprising a pharmaceutically acceptable carrier and the agent-drug conjugate of embodiment C23 or C24.

C26. A method of diagnosing a disease or disorder associated with aberrant levels of TSPAN33, comprising detecting an aberrant level of TSPAN33 using the first anti-TSPAN33 agent of any one of embodiments C1 to C13, thereby diagnosing the disease or disorder.

C27. A method of treating or preventing a disease or disorder associated with aberrant levels of TSPAN33, comprising administering to a subject in need of such treatment the first anti-TSPAN33 agent of any one of embodiments C1 to C13 in an amount sufficient to effect treatment, thereby treating or preventing the disease or disorder.

C28. A method of treating or preventing a disease or disorder associated with aberrant levels of TSPAN33, comprising administering to a subject in need of such treatment the agent-drug conjugate of embodiment C23 or C24 in an amount sufficient to effect treatment, thereby treating or preventing the disease or disorder.

C29. The method of embodiment C26, C27 or C28, wherein the disease or disorder is chosen from leukemia, lymphoma, and an autoimmune disease.

C30. The method of embodiment C29, wherein the lymphoma is Hodgkin's disease, non-Hodgkin's lymphoma, diffuse large B cell lymphoma, or Burkitt's lymphoma.

C31. The method of embodiment C29, wherein the autoimmune disease is rheumatoid arthritis.

C32. A method of selectively targeting activated B cells in a subject, comprising administering to the subject the first anti-TSPAN33 agent of any one of embodiments C1 to C13, wherein the first anti-TSPAN33 agent binds to TSPAN33 on activated B cells.

C33. A method of selectively targeting activated B cells in a subject, comprising administering to the subject the agent-drug conjugate of embodiment C23 or C24, wherein the first anti-TSPAN33 agent in the agent-drug conjugate binds to TSPAN33 on activated B cells.

C34. The method of embodiment C32 or C33, wherein the first anti-TSPAN33 agent does not bind to T cells.

C35. The method of any one of embodiments C32 to C34, wherein the subject has a disease or disorder chosen from leukemia, lymphoma, and an autoimmune disease.

C36. The method of embodiment C35, wherein the lymphoma is Hodgkin's disease, non-Hodgkin's lymphoma, diffuse large B cell lymphoma, or Burkitt's lymphoma.

C37. The method of embodiment C35, wherein the autoimmune disease is rheumatoid arthritis.

C38. A chimeric antigen receptor modified T (CAR-T) cell comprising the first anti-TSPAN33 agent of any one of embodiments C1 to C13, or the isolated nucleic acid molecule of embodiment C17 or C18.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. An anti-TSPAN33 agent that binds Tetraspanin 33 (TSPAN33) under laboratory or physiological conditions, wherein the agent comprises at least one immunoglobulin heavy chain variable domain and at least one immunoglobulin light chain variable domain, wherein:
   a) each immunoglobulin heavy chain variable domain of the anti-TSPAN33 agent comprises first, second, and third heavy chain complementarity determining regions (CDRs), and b) each immunoglobulin light chain variable domain of the anti-TSPAN33 agent comprises first, second, and third light chain CDRs, wherein each immunoglobulin heavy chain variable domain comprises a set of CDRH1, CDRH2 and CDRH3 amino acid sequences and each immunoglobulin light chain variable domain comprises a set of CDRL1, CDRL2 and CDRL3 amino acid sequences chosen from sets 1-4:

| set | CDRH1 (SEQ ID NO:) | CDRH2 (SEQ ID NO:) | CDRH3 (SEQ ID NO:) |
|---|---|---|---|
| 1 | DYYMT (1) | FIRNKANGYTT EYSASVKG (2) | YLQTGNFDY (3) |
| 2 | SYWMH (9) | RIDPNSGGTKY NEKFKS (10) | FIITGYFDY (11) |
| 3 | NYYMN (17 and 25) | DIIPNNGGTIYN QKFKG (18 and 26) | RLWSWYFDV (19 and 27) |
| 4 | SYWMH (33) | EINPNNGGSNY NEKFKN (34) | SYYSYWYFDY (35) |

| set | CDRL1 (SEQ ID NO:) | CDRL2 (SEQ ID NO:) | CDRL3 (SEQ ID NO:) |
|---|---|---|---|
| 1 | RASQDISNFL N (5) | FTSRLHS (6) | QQGYTVPPT (7) |
| 2 | KASQDVGAA VA (13) | WASTRHT (14) | HQYRTYPFT (15) |
| 3 | SASSSVSYM Y (21 and 29) | LTSNLAS (22 and 30) | QQWSSNPY T (23 and 31) |
| 4 | SASSSVNYM H (37) | DTSKLAP (38) | HQWNNYPY T (39) | and wherein all CDR sequences are from the same set.

2. The anti-TSPAN33 agent of claim 1, wherein the immunoglobulin heavy chain variable domain comprises a polypeptide that is at least 75 percent identical, at least 80 percent identical, at least 85 percent identical, at least 90 percent identical, at least 95 percent identical, or 100 percent identical to an amino acid sequence chosen from SEQ ID NO: 4, SEQ ID NO: 12, SEQ ID NO: 20, SEQ ID NO: 28, and SEQ ID NO: 36.

3. The anti-TSPAN33 agent of claim 1, wherein the immunoglobulin light chain variable domain comprises a polypeptide that is at least 75 percent identical, at least 80 percent identical, at least 85 percent identical, at least 90 percent identical, at least 95 percent identical, or 100 percent identical to an amino acid sequence chosen from SEQ ID NO: 8, SEQ ID NO: 16, SEQ ID NO: 24, SEQ ID NO: 32, and SEQ ID NO: 40.

4. The anti-TSPAN33 agent of claim 1, wherein the agent comprises or is conjugated to a detectable marker or label.

5. The anti-TSPAN33 agent of claim 1, wherein the agent is non-diffusively immobilized on a solid support.

6. An isolated nucleic acid molecule comprising a nucleotide sequence that encodes an immunoglobulin heavy chain variable domain of the anti-TSPAN33 agent of claim 1; or an isolated nucleic acid molecule comprising a nucleotide sequence that encodes an immunoglobulin light chain variable domain of the anti-TSPAN33 agent of claim 1.

7. A recombinant expression vector comprising a first expression cassette and a second expression cassette, wherein the first expression cassette comprises a promoter and a nucleic acid molecule comprising a nucleotide sequence that encodes an immunoglobulin heavy chain variable domain of the anti-TSPAN33 agent of claim 1, and the second expression cassette comprises a promoter and a nucleic acid molecule comprising a nucleotide sequence that encodes an immunoglobulin light chain variable domain of the anti-TSPAN33 agent of claim 1.

8. A method of detecting TSPAN33, comprising contacting a sample known or suspected to contain TSPAN33 with the anti-TSPAN33 agent of claim 1, and, if the sample contains TSPAN33, detecting TSPAN33:anti-TSPAN33 complexes.

9. A method of treating or preventing a disease or disorder associated with aberrant levels of TSPAN33, comprising administering to a subject in need of such treatment the anti-TSPAN33 agent of claim 1 in an amount sufficient to effect treatment, thereby treating or preventing the disease or disorder.

* * * * *

```
SEQUENCE LISTING

<160> NUMBER OF SEQ ID NOS: 60

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Asp Tyr Tyr Met Thr
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic construct

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Tyr Leu Gln Thr Gly Asn Phe Asp Tyr
1               5

<210> SEQ ID NO 4
<211> LENGTH: 120
<212> TYPE: PRT
<213> ORGANISM: Artificial Sequence
<220> FEATURE:
<223> OTHER INFORMATION: Synthetic construct

<400> SEQUENCE: 4

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Thr Trp Val Arg Gln Pro Pro Gly Lys Ala Leu Glu Trp Leu
        35                  40                  45
```

```
Val Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Gln Ser Ile
 65                  70                  75                  80

Leu Tyr Leu Gln Met Asn Ala Leu Arg Ala Glu Asp Ser Ala Thr Tyr
                 85                  90                  95

Tyr Cys Ala Arg Tyr Leu Gln Thr Gly Asn Phe Asp Tyr Trp Gly Gln
                100                 105                 110

Gly Thr Thr Leu Thr Val Ser Ser
            115                 120

<210> SEQ ID NO 5
<211> LENGTH: 11
<212> TYPE: PRT
<213> ORGANISM: Artificial Sequence
<220> FEATURE:
<223> OTHER INFORMATION: Synthetic construct

<400> SEQUENCE: 5

Arg Ala Ser Gln Asp Ile Ser Asn Phe Leu Asn
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic construct

<400> SEQUENCE: 6

Phe Thr Ser Arg Leu His Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Gln Gln Gly Tyr Thr Val Pro Pro Thr
1               5

<210> SEQ ID NO 8
<211> LENGTH: 107
<212> TYPE: PRT
<213> ORGANISM: Artificial Sequence
<220> FEATURE:
<223> OTHER INFORMATION: Synthetic construct

<400> SEQUENCE: 8

Glu Ile Gln Met Ile Gln Thr Thr Ser Ser Leu Thr Ala Ser Leu Gly
1               5                   10                  15

Asp Arg Val Thr Ile Ser Cys Arg Ala Ser Gln Asp Ile Ser Asn Phe
                 20                  25                  30

Leu Asn Trp Tyr Gln Gln Lys Pro Asp Gly Thr Ile Lys Leu Leu Ile
             35                  40                  45

Tyr Phe Thr Ser Arg Leu His Ser Gly Val Pro Ser Arg Phe Ser Gly
         50                  55                  60

Ser Gly Ser Gly Thr Asp Tyr Ser Leu Thr Ile Ser Asn Leu Glu Gln
 65                  70                  75                  80
```

Glu Asp Ile Ala Thr Tyr Phe Cys Gln Gln Gly Tyr Thr Val Pro Pro
                85                  90                  95

Thr Phe Gly Gly Gly Thr Lys Leu Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Ser Tyr Trp Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic construct

<400> SEQUENCE: 10

Arg Ile Asp Pro Asn Ser Gly Gly Thr Lys Tyr Asn Glu Lys Phe Lys
1               5                   10                  15

Ser

<210> SEQ ID NO 11
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

Phe Ile Ile Thr Gly Tyr Phe Asp Tyr
1               5

<210> SEQ ID NO 12
<211> LENGTH: 118
<212> TYPE: PRT
<213> ORGANISM: Artificial Sequence
<220> FEATURE:
<223> OTHER INFORMATION: Synthetic construct

<400> SEQUENCE: 12

Gln Val Gln Leu Gln Gln Pro Gly Ala Glu Leu Leu Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Ile His Leu Ser Ser Leu Thr Ser Glu Asp Ser Ala Val Tyr Tyr Cys
                85                  90                  95

Ala Arg Phe Ile Ile Thr Gly Tyr Phe Asp Tyr Trp Gly Gln Gly Thr
            100                 105                 110

Thr Leu Ile Val Ser Ser

<210> SEQ ID NO 13
<211> LENGTH: 11
<212> TYPE: PRT
<213> ORGANISM: Artificial Sequence
<220> FEATURE:
<223> OTHER INFORMATION: Synthetic construct

<400> SEQUENCE: 13

```
Lys Ala Ser Gln Asp Val Gly Ala Ala Val Ala
1               5                   10
```

<210> SEQ ID NO 14
<211> LENGTH: 7
<212> TYPE: PRT
<213> ORGANISM: Artificial Sequence
<220> FEATURE:
<223> OTHER INFORMATION: Synthetic construct

<400> SEQUENCE: 14

```
Trp Ala Ser Thr Arg His Thr
1               5
```

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

<400> SEQUENCE: 15

```
His Gln Tyr Arg Thr Tyr Pro Phe Thr
1               5
```

<210> SEQ ID NO 16
<211> LENGTH: 107
<212> TYPE: PRT
<213> ORGANISM: Artificial Sequence
<220> FEATURE:
<223> OTHER INFORMATION: Synthetic construct

<400> SEQUENCE: 16

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Thr Val Gln Ser
65                  70                  75                  80

Glu Asp Leu Ala Asp Tyr Phe Cys His Gln Tyr Arg Thr Tyr Pro Phe
                85                  90                  95

Thr Phe Gly Ser Gly Thr Lys Leu Gly Ile Lys
            100                 105
```

<210> SEQ ID NO 17
<211> LENGTH: 5
<212> TYPE: PRT
<213> ORGANISM: Artificial Sequence
<220> FEATURE:
<223> OTHER INFORMATION: Synthetic construct

<400> SEQUENCE: 17

Asn Tyr Tyr Met Asn
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic construct

<400> SEQUENCE: 18

Asp Ile Ile Pro Asn Asn Gly Gly Thr Ile Tyr Asn Gln Lys Phe Lys
1               5                   10                  15

Gly

<210> SEQ ID NO 19
<211> LENGTH: 9
<212> TYPE: PRT
<213> ORGANISM: Artificial Sequence
<220> FEATURE:
<223> OTHER INFORMATION: Synthetic construct

<400> SEQUENCE: 19

Arg Leu Trp Ser Trp Tyr Phe Asp Val
1               5

<210> SEQ ID NO 20
<211> LENGTH: 118
<212> TYPE: PRT
<213> ORGANISM: Artificial Sequence
<220> FEATURE:
<223> OTHER INFORMATION: Synthetic construct

<400> SEQUENCE: 20

Glu Ala Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
                20                  25                  30

Tyr Met Asn Trp Met Lys Gln Ser His Gly Lys Ser Leu Glu Trp Ile
            35                  40                  45

Gly Asp Ile Ile Pro Asn Asn Gly Gly Thr Ile Tyr Asn Gln Lys Phe
        50                  55                  60

Lys Gly Lys Ala Thr Leu Thr Val Asp Arg Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Leu Trp Ser Trp Tyr Phe Asp Val Trp Gly Thr Gly Thr
            100                 105                 110

Thr Val Thr Val Ser Ser
        115

<210> SEQ ID NO 21
<211> LENGTH: 10
<212> TYPE: PRT
<213> ORGANISM: Artificial Sequence
<220> FEATURE:
<223> OTHER INFORMATION: Synthetic construct

<400> SEQUENCE: 21

Ser Ala Ser Ser Ser Val Ser Tyr Met Tyr

```
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic construct

<400> SEQUENCE: 22

Leu Thr Ser Asn Leu Ala Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic construct

<400> SEQUENCE: 23

Gln Gln Trp Ser Ser Asn Pro Tyr Thr
1               5

<210> SEQ ID NO 24
<211> LENGTH: 106
<212> TYPE: PRT
<213> ORGANISM: Artificial Sequence
<220> FEATURE:
<223> OTHER INFORMATION: Synthetic construct

<400> SEQUENCE: 24

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 25
<211> LENGTH: 5
<212> TYPE: PRT
<213> ORGANISM: Artificial Sequence
<220> FEATURE:
<223> OTHER INFORMATION: Synthetic construct

<400> SEQUENCE: 25

Asn Tyr Tyr Met Asn
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic construct
```

<400> SEQUENCE: 26

Asp Ile Ile Pro Asn Asn Gly Gly Thr Ile Tyr Asn Gln Lys Phe Lys
1               5                   10                  15

Gly

<210> SEQ ID NO 27
<211> LENGTH: 9
<212> TYPE: PRT
<213> ORGANISM: Artificial Sequence
<220> FEATURE:
<223> OTHER INFORMATION: Synthetic construct

<400> SEQUENCE: 27

Arg Leu Trp Ser Trp Tyr Phe Asp Val
1               5

<210> SEQ ID NO 28
<211> LENGTH: 118
<212> TYPE: PRT
<213> ORGANISM: Artificial Sequence
<220> FEATURE:
<223> OTHER INFORMATION: Synthetic construct

<400> SEQUENCE: 28

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
                20                  25                  30

Tyr Met Asn Trp Met Lys Gln Ser His Gly Lys Ser Leu Glu Trp Ile
            35                  40                  45

Gly Asp Ile Ile Pro Asn Asn Gly Gly Thr Ile Tyr Asn Gln Lys Phe
        50                  55                  60

Lys Gly Lys Ala Thr Leu Thr Val Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Leu Trp Ser Trp Tyr Phe Asp Val Trp Gly Thr Gly Thr
            100                 105                 110

Thr Val Thr Val Ser Ser
        115

<210> SEQ ID NO 29
<211> LENGTH: 10
<212> TYPE: PRT
<213> ORGANISM: Artificial Sequence
<220> FEATURE:
<223> OTHER INFORMATION: Synthetic construct

<400> SEQUENCE: 29

Ser Ala Ser Ser Ser Val Ser Tyr Met Tyr
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic construct

<400> SEQUENCE: 30

Leu Thr Ser Asn Leu Ala Ser

```
<210> SEQ ID NO 31
<211> LENGTH: 9
<212> TYPE: PRT
<213> ORGANISM: Artificial Sequence
<220> FEATURE:
<223> OTHER INFORMATION: Synthetic construct

<400> SEQUENCE: 31

Gln Gln Trp Ser Ser Asn Pro Tyr Thr
1               5

<210> SEQ ID NO 32
<211> LENGTH: 106
<212> TYPE: PRT
<213> ORGANISM: Artificial Sequence
<220> FEATURE:
<223> OTHER INFORMATION: Synthetic construct

<400> SEQUENCE: 32

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

Ser Tyr Trp Met His
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic construct

<400> SEQUENCE: 34

Glu Ile Asn Pro Asn Asn Gly Gly Ser Asn Tyr Asn Glu Lys Phe Lys
1               5                   10                  15

Asn

<210> SEQ ID NO 35
<211> LENGTH: 10
<212> TYPE: PRT
<213> ORGANISM: Artificial Sequence
```

```
<220> FEATURE:
<223> OTHER INFORMATION: Synthetic construct

<400> SEQUENCE: 35

Ser Tyr Tyr Ser Tyr Trp Tyr Phe Asp Tyr
1               5                   10

<210> SEQ ID NO 36
<211> LENGTH: 119
<212> TYPE: PRT
<213> ORGANISM: Artificial Sequence
<220> FEATURE:
<223> OTHER INFORMATION: Synthetic construct

<400> SEQUENCE: 36

Gln Val Gln Leu Gln Gln Pro Gly Ala Glu Phe Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Asn Asn Gly Gly Ser Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Gly Leu Thr Ser Glu Asp Ser Ala Val Tyr Tyr Cys
                85                  90                  95

Thr Arg Ser Tyr Tyr Ser Tyr Trp Tyr Phe Asp Tyr Trp Gly Gln Gly
            100                 105                 110

Thr Thr Leu Thr Val Ser Ser
        115

<210> SEQ ID NO 37
<211> LENGTH: 10
<212> TYPE: PRT
<213> ORGANISM: Artificial Sequence
<220> FEATURE:
<223> OTHER INFORMATION: Synthetic construct

<400> SEQUENCE: 37

Ser Ala Ser Ser Ser Val Asn Tyr Met His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic construct

<400> SEQUENCE: 38

Asp Thr Ser Lys Leu Ala Pro
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic construct

<400> SEQUENCE: 39

His Gln Trp Asn Asn Tyr Pro Tyr Thr
```

```
1               5

<210> SEQ ID NO 40
<211> LENGTH: 106
<212> TYPE: PRT
<213> ORGANISM: Artificial Sequence
<220> FEATURE:
<223> OTHER INFORMATION: Synthetic construct

<400> SEQUENCE: 40

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Ser Val Asn Tyr Met
            20                  25                  30

His Trp Tyr Gln Gln Lys Leu Gly Ser Ser Pro Lys Leu Trp Ile Tyr
        35                  40                  45

Asp Thr Ser Lys Leu Ala Pro Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Ser Tyr Phe Cys His Gln Trp Asn Asn Tyr Pro Tyr Thr
                85                  90                  95

Phe Gly Ser Gly Thr Lys Leu Glu Ile Lys
            100                 105

<210> SEQ ID NO 41
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: Variant
<222> LOCATION: (1)..(1)
<223> OTHER INFORMATION: X = D, S, or N
<220> FEATURE:
<221> NAME/KEY: Variant
<222> LOCATION: (3)..(3)
<223> OTHER INFORMATION: X = Y or W
<220> FEATURE:
<221> NAME/KEY: Variant
<222> LOCATION: (5)..(5)
<223> OTHER INFORMATION: X = N, H, or T

<400> SEQUENCE: 41

Xaa Tyr Xaa Met Xaa
1               5

<210> SEQ ID NO 42
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: Variant
<222> LOCATION: (1)..(1)
<223> OTHER INFORMATION: X=F, R, D or E
<220> FEATURE:
<221> NAME/KEY: Variant
<222> LOCATION: (3)..(3)
<223> OTHER INFORMATION: X=R, D, I, or N
<220> FEATURE:
<221> NAME/KEY: Variant
<222> LOCATION: (4)..(4)
<223> OTHER INFORMATION: X= N or P
<220> FEATURE:
<221> NAME/KEY: Variant
```

```
<222> LOCATION: (5)..(5)
<223> OTHER INFORMATION: X= N or K
<220> FEATURE:
<221> NAME/KEY: Variant
<222> LOCATION: (6)..(6)
<223> OTHER INFORMATION: X= A, S, or N
<220> FEATURE:
<221> NAME/KEY: Variant
<222> LOCATION: (7)..(7)
<223> OTHER INFORMATION: X= N or G
<220> FEATURE:
<221> NAME/KEY: Variant
<222> LOCATION: (9)..(9)
<223> OTHER INFORMATION: X= Y or no amino acid
<220> FEATURE:
<221> NAME/KEY: Variant
<222> LOCATION: (10)..(10)
<223> OTHER INFORMATION: X= T or no amino acid
<220> FEATURE:
<221> NAME/KEY: Variant
<222> LOCATION: (11)..(11)
<223> OTHER INFORMATION: X= T or S
<220> FEATURE:
<221> NAME/KEY: Variant
<222> LOCATION: (12)..(12)
<223> OTHER INFORMATION: X= E, K, I or N
<220> FEATURE:
<221> NAME/KEY: Variant
<222> LOCATION: (14)..(14)
<223> OTHER INFORMATION: X= S or N
<220> FEATURE:
<221> NAME/KEY: Variant
<222> LOCATION: (15)..(15)
<223> OTHER INFORMATION: X= A, E or Q
<220> FEATURE:
<221> NAME/KEY: Variant
<222> LOCATION: (16)..(16)
<223> OTHER INFORMATION: X= S or K
<220> FEATURE:
<221> NAME/KEY: Variant
<222> LOCATION: (17)..(17)
<223> OTHER INFORMATION: X= V or F
<220> FEATURE:
<221> NAME/KEY: Variant
<222> LOCATION: (19)..(19)
<223> OTHER INFORMATION: X= G, S, or N

<400> SEQUENCE: 42

Xaa Ile Xaa Xaa Xaa Xaa Xaa Gly Xaa Xaa Xaa Xaa Tyr Xaa Xaa Xaa
1               5                   10                  15

Xaa Lys Xaa

<210> SEQ ID NO 43
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: Variant
<222> LOCATION: (1)..(1)
<223> OTHER INFORMATION: X = no amino acid or S
<220> FEATURE:
<221> NAME/KEY: Variant
<222> LOCATION: (2)..(2)
<223> OTHER INFORMATION: X = Y, F, or R
<220> FEATURE:
<221> NAME/KEY: Variant
<222> LOCATION: (3)..(3)
<223> OTHER INFORMATION: X = L, I, or Y
<220> FEATURE:
<221> NAME/KEY: Variant
<222> LOCATION: (4)..(4)
<223> OTHER INFORMATION: X = Q, I, W, or S
<220> FEATURE:
<221> NAME/KEY: Variant
```

```
<222> LOCATION: (5)..(5)
<223> OTHER INFORMATION: X = T, S, or Y
<220> FEATURE:
<221> NAME/KEY: Variant
<222> LOCATION: (6)..(6)
<223> OTHER INFORMATION: X = G or W
<220> FEATURE:
<221> NAME/KEY: Variant
<222> LOCATION: (7)..(7)
<223> OTHER INFORMATION: X = N or Y
<220> FEATURE:
<221> NAME/KEY: Variant
<222> LOCATION: (10)..(10)
<223> OTHER INFORMATION: X = Y or V

<400> SEQUENCE: 43

Xaa Xaa Xaa Xaa Xaa Xaa Xaa Phe Asp Xaa
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: X = R, K, or S
<220> FEATURE:
<221> NAME/KEY: VARIANT
<222> LOCATION: (4)..(4)
<223> OTHER INFORMATION: X = Q or S
<220> FEATURE:
<221> NAME/KEY: VARIANT
<222> LOCATION: (5)..(5)
<223> OTHER INFORMATION: X = D or S
<220> FEATURE:
<221> NAME/KEY: VARIANT
<222> LOCATION: (6)..(6)
<223> OTHER INFORMATION: X = I or V
<220> FEATURE:
<221> NAME/KEY: VARIANT
<222> LOCATION: (7)..(7)
<223> OTHER INFORMATION: X = S, G, or N
<220> FEATURE:
<221> NAME/KEY: VARIANT
<222> LOCATION: (8)..(8)
<223> OTHER INFORMATION: X = N, A, or no amino acid
<220> FEATURE:
<221> NAME/KEY: VARIANT
<222> LOCATION: (9)..(9)
<223> OTHER INFORMATION: X = F, A, or Y
<220> FEATURE:
<221> NAME/KEY: VARIANT
<222> LOCATION: (10)..(10)
<223> OTHER INFORMATION: X = L, V, or M
<220> FEATURE:
<221> NAME/KEY: VARIANT
<222> LOCATION: (11)..(11)
<223> OTHER INFORMATION: X = N, A, Y, or H

<400> SEQUENCE: 44

Xaa Ala Ser Xaa Xaa Xaa Xaa Xaa Xaa Xaa Xaa
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
```

```
<223> OTHER INFORMATION: X = F, W, L or D
<220> FEATURE:
<221> NAME/KEY: VARIANT
<222> LOCATION: (2)..(2)
<223> OTHER INFORMATION: X = T or A
<220> FEATURE:
<221> NAME/KEY: VARIANT
<222> LOCATION: (4)..(4)
<223> OTHER INFORMATION: X = R, T, N, or K
<220> FEATURE:
<221> NAME/KEY: VARIANT
<222> LOCATION: (5)..(5)
<223> OTHER INFORMATION: X = L or R
<220> FEATURE:
<221> NAME/KEY: VARIANT
<222> LOCATION: (6)..(6)
<223> OTHER INFORMATION: X = H or A
<220> FEATURE:
<221> NAME/KEY: VARIANT
<222> LOCATION: (7)..(7)
<223> OTHER INFORMATION: X = S, T, or P

<400> SEQUENCE: 45

Xaa Xaa Ser Xaa Xaa Xaa Xaa
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: X = Q or H
<220> FEATURE:
<221> NAME/KEY: VARIANT
<222> LOCATION: (3)..(3)
<223> OTHER INFORMATION: X = G, Y, or W
<220> FEATURE:
<221> NAME/KEY: VARIANT
<222> LOCATION: (4)..(4)
<223> OTHER INFORMATION: X = Y, R, S or N
<220> FEATURE:
<221> NAME/KEY: VARIANT
<222> LOCATION: (5)..(5)
<223> OTHER INFORMATION: X = T, S, or N
<220> FEATURE:
<221> NAME/KEY: VARIANT
<222> LOCATION: (6)..(6)
<223> OTHER INFORMATION: X = V, Y, or N
<220> FEATURE:
<221> NAME/KEY: VARIANT
<222> LOCATION: (8)..(8)
<223> OTHER INFORMATION: X = P, F, or Y

<400> SEQUENCE: 46

Xaa Gln Xaa Xaa Xaa Xaa Pro Xaa Thr
1               5

<210> SEQ ID NO 47
<211> LENGTH: 283
<212> TYPE: PRT
<213> ORGANISM: Homo sapiens
<220> FEATURE:
<221> NAME/KEY: Variant
<222> LOCATION: (1)..(1)
<223> OTHER INFORMATION: X = F, R, D or E
<220> FEATURE:
<221> NAME/KEY: Variant
<222> LOCATION: (3)..(3)
<223> OTHER INFORMATION: X = R, D, I or N
<220> FEATURE:
<221> NAME/KEY: Variant
```

```
<222> LOCATION: (4)..(4)
<223> OTHER INFORMATION: X = N or P
<220> FEATURE:
<221> NAME/KEY: Variant
<222> LOCATION: (5)..(5)
<223> OTHER INFORMATION: X = N or K
<220> FEATURE:
<221> NAME/KEY: Variant
<222> LOCATION: (6)..(6)
<223> OTHER INFORMATION: X = A, S, or N
<220> FEATURE:
<221> NAME/KEY: Variant
<222> LOCATION: (7)..(7)
<223> OTHER INFORMATION: X = N or G
<220> FEATURE:
<221> NAME/KEY: Variant
<222> LOCATION: (9)..(9)
<223> OTHER INFORMATION: X = Y or no amino acid
<220> FEATURE:
<221> NAME/KEY: Variant
<222> LOCATION: (9)..(9)
<223> OTHER INFORMATION: X = Y or no amino acid
<220> FEATURE:
<221> NAME/KEY: Variant
<222> LOCATION: (10)..(10)
<223> OTHER INFORMATION: X = T or no amino acid

<400> SEQUENCE: 47

Met Ala Arg Arg Pro Arg Ala Pro Ala Ala Ser Gly Glu Glu Phe Ser
1               5                   10                  15

Phe Val Ser Pro Leu Val Lys Tyr Leu Leu Phe Phe Phe Asn Met Leu
            20                  25                  30

Phe Trp Val Ile Ser Met Val Met Val Ala Val Gly Val Tyr Ala Arg
        35                  40                  45

Leu Met Lys His Ala Glu Ala Ala Leu Ala Cys Leu Ala Val Asp Pro
    50                  55                  60

Ala Ile Leu Leu Ile Val Val Gly Val Leu Met Phe Leu Leu Thr Phe
65                  70                  75                  80

Cys Gly Cys Ile Gly Ser Leu Arg Glu Asn Ile Cys Leu Leu Gln Thr
                85                  90                  95

Phe Ser Leu Cys Leu Thr Ala Val Phe Leu Leu Gln Leu Ala Ala Gly
            100                 105                 110

Ile Leu Gly Phe Val Phe Ser Asp Lys Ala Arg Gly Lys Val Ser Glu
        115                 120                 125

Ile Ile Asn Asn Ala Ile Val His Tyr Arg Asp Asp Leu Asp Leu Gln
    130                 135                 140

Asn Leu Ile Asp Phe Gly Gln Lys Lys Phe Ser Cys Cys Gly Gly Ile
145                 150                 155                 160

Ser Tyr Lys Asp Trp Ser Gln Asn Met Tyr Phe Asn Cys Ser Glu Asp
                165                 170                 175

Asn Pro Ser Arg Glu Arg Cys Ser Val Pro Tyr Ser Cys Cys Leu Pro
            180                 185                 190

Thr Pro Asp Gln Ala Val Ile Asn Thr Met Cys Gly Gln Gly Met Gln
        195                 200                 205

Ala Phe Asp Tyr Leu Glu Ala Ser Lys Val Ile Tyr Thr Asn Gly Cys
    210                 215                 220

Ile Asp Lys Leu Val Asn Trp Ile His Ser Asn Leu Phe Leu Leu Gly
225                 230                 235                 240

Gly Val Ala Leu Gly Leu Ala Ile Pro Gln Leu Val Gly Ile Leu Leu
                245                 250                 255

Ser Gln Ile Leu Val Asn Gln Ile Lys Asp Gln Ile Lys Leu Gln Leu
            260                 265                 270
```

Tyr Asn Gln Gln His Arg Ala Asp Pro Trp Tyr
        275                 280

<210> SEQ ID NO 48
<211> LENGTH: 4
<212> TYPE: PRT
<213> ORGANISM: Artificial Sequence
<220> FEATURE:
<223> OTHER INFORMATION: Synthetic construct

<400> SEQUENCE: 48

Asn Glu Gln Lys
1

<210> SEQ ID NO 49
<211> LENGTH: 4
<212> TYPE: PRT
<213> ORGANISM: Artificial Sequence
<220> FEATURE:
<223> OTHER INFORMATION: Synthetic construct

<400> SEQUENCE: 49

Asn His Gln Lys
1

<210> SEQ ID NO 50
<211> LENGTH: 4
<212> TYPE: PRT
<213> ORGANISM: Artificial Sequence
<220> FEATURE:
<223> OTHER INFORMATION: Synthetic construct

<400> SEQUENCE: 50

Asn Asp Glu Gln
1

<210> SEQ ID NO 51
<211> LENGTH: 4
<212> TYPE: PRT
<213> ORGANISM: Artificial Sequence
<220> FEATURE:
<223> OTHER INFORMATION: Synthetic construct

<400> SEQUENCE: 51

Gln His Arg Lys
1

<210> SEQ ID NO 52
<211> LENGTH: 4
<212> TYPE: PRT
<213> ORGANISM: Artificial Sequence
<220> FEATURE:
<223> OTHER INFORMATION: Synthetic construct

<400> SEQUENCE: 52

Met Ile Leu Val
1

<210> SEQ ID NO 53
<211> LENGTH: 4
<212> TYPE: PRT
<213> ORGANISM: Artificial Sequence
<220> FEATURE:
<223> OTHER INFORMATION: Synthetic construct

<400> SEQUENCE: 53

-continued

Met Ile Leu Phe
1

<210> SEQ ID NO 54
<211> LENGTH: 4
<212> TYPE: PRT
<213> ORGANISM: Artificial Sequence
<220> FEATURE:
<223> OTHER INFORMATION: Synthetic construct

<400> SEQUENCE: 54

Ser Thr Asn Lys
1

<210> SEQ ID NO 55
<211> LENGTH: 4
<212> TYPE: PRT
<213> ORGANISM: Artificial Sequence
<220> FEATURE:
<223> OTHER INFORMATION: Synthetic construct

<400> SEQUENCE: 55

Ser Thr Pro Ala
1

<210> SEQ ID NO 56
<211> LENGTH: 4
<212> TYPE: PRT
<213> ORGANISM: Artificial Sequence
<220> FEATURE:
<223> OTHER INFORMATION: Synthetic construct

<400> SEQUENCE: 56

Ser Gly Asn Asp
1

<210> SEQ ID NO 57
<211> LENGTH: 6
<212> TYPE: PRT
<213> ORGANISM: Artificial Sequence
<220> FEATURE:
<223> OTHER INFORMATION: Synthetic construct

<400> SEQUENCE: 57

Ser Asn Asp Glu Gln Lys
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic construct

<400> SEQUENCE: 58

Asn Asp Glu Gln His Lys
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic construct

<400> SEQUENCE: 59

Asn Glu Gln His Arg Lys

```
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic construct

<400> SEQUENCE: 60

Phe Val Leu Ile Met
1               5
```